US006476211B1

(12) United States Patent
Ford et al.

(10) Patent No.: US 6,476,211 B1
(45) Date of Patent: Nov. 5, 2002

(54) METHODS AND MATERIALS RELATING TO CD39-LIKE POLYPEPTIDES

(75) Inventors: John Ford, San Mateo; Julio J. Mulero, Palo Alto; George Yeung, Mountain View, all of CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/557,800

(22) Filed: Apr. 25, 2000

Related U.S. Application Data

(63) Continuation-in-part of application No. 09/481,238, filed on Jan. 11, 2000, now abandoned, which is a continuation-in-part of application No. 09/370,265, filed on Aug. 9, 1999, which is a continuation-in-part of application No. PCT/US99/16180, filed on Jul. 16, 1999, which is a continuation-in-part of application No. 09/350,836, filed on Jul. 9, 1999, which is a continuation-in-part of application No. 09/273,447, filed on Mar. 19, 1999, now abandoned, which is a continuation-in-part of application No. 09/122,449, filed on Jul. 24, 1998, now abandoned, application No. 09/557,800, which is a continuation-in-part of application No. 09/244,444, filed on Feb. 4, 1999, now abandoned, which is a continuation of application No. 09/118,205, filed on Jul. 16, 1998, now abandoned.

(51) Int. Cl.$^7$ .............................................. C07H 21/04
(52) U.S. Cl. ...................... 536/23.5; 435/6; 435/69.1; 435/252.3; 435/320.1
(58) Field of Search ........................... 536/23.5; 435/6, 435/69.1, 320.1, 252.3

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,683,195 A | 7/1987 | Mullis et al. | |
| 4,737,323 A | 4/1988 | Martin et al. | |
| 4,837,028 A | 6/1989 | Allen | |
| 4,840,896 A | * 6/1989 | Reddy et al. | |
| 4,946,778 A | 8/1990 | Ladner et al. | |
| 4,959,314 A | 9/1990 | Mark et al. | |
| 4,965,188 A | 10/1990 | Mullis et al. | |
| 5,202,231 A | 4/1993 | Drmanac et al. | |
| 5,525,464 A | 6/1996 | Drmanac et al. | |

FOREIGN PATENT DOCUMENTS

| | | |
|---|---|---|
| CA | 2148851 | 10/1996 |
| WO | WO 90/03382 | 4/1990 |
| WO | WO 90/14148 | 11/1990 |
| WO | WO 91/09955 | 7/1991 |
| WO | WO 92/20808 | 11/1992 |
| WO | WO 94/12650 | 6/1994 |
| WO | WO 95/09248 | 4/1995 |
| WO | WO 96/30532 | 10/1996 |
| WO | WO 96/32471 | 10/1996 |

OTHER PUBLICATIONS

Chadwick and Frischauf, Genomics 50:357–367, (1998).*
Boukerche, H. et al., "Human melanoma cell lines differ in their capactiy to release ADP and aggregate platelets," *Br. J. Haematol.*, 87(4):763–72 (1994).
Dzhaudzhugazyan, K.N. et al., "Ecto–ATP diphosphohydrolase/CD39 is overexpressed in differentiated human melanomas," *FEBS Lett.*, 430(3):227–30 (1998).
Clifford, E.E. et al., "Stage–specific expression of P2Y receptors ecto–apyrase, and ecto–5'—nucteotidase in myeloid leukocytes," *Am. J. Physiol.*, 273(3 Pt. 1):C973–87 (1997).
Katzur, A.C., et al., Expression and responsiveness of P2Y2 receptors in human endometrial cancer cell lines, *J. Clin. Endocrinol. Metab.*, 84(11):4085–91 (1999).
Correale, P., et al., Extracellular adenosine 5' triphosphate involvement in the death of LAK–engaged human tumor cells via P2X–receptor activation, *Immunol. Lett.*, 55(2): 69–78 (1997).
Barnard. E.A., et al., "Nucleotide receptors in the nervous system. An abundant component using diverse transduction mechanism," *Mol. Neurobiol.* 15(2):103–29 (1997).
Abbracchio, M.P. and Burnstock G., "Purinoreceptors: Are there families of P2X and P2Y Purinoreceptpors?," *Pharmac. Ther.*, 64:445–75 (1994).
Illes, P. et al., "Electrophysiological effects of ATP on brain neurones," *J. Auton. Pharmacol.*, 16(6):407–11 (1996).
Barnard, E.A., et al., "The diverse series of recombinant P2Y purinoreceptors," *Ciba Found. Symp.*, 198: 166–88 (1996).
Williams, M. and Jarvis, M.F., "Purinergic and pyrimidinergic receptors as potential drug targets," *Biochem. Pharmacol.*, 59(10):1173–85 (2000).
King, B.F. et al., "Metabotropic receptors for ATP and UTP: exploring the correspondence between native and recombinant nucleotide receptors," *Trends Pharmacol. Sci.*, 19(12):506–14 (1998).
Nicholas, R.A., et al., "Pharmacological and second messenger signaling selectivities of cloned P2Y receptors," *J. Auton. Pharmacol.*, 16(6):319–23 (1996).

(List continued on next page.)

Primary Examiner—David Saunders
Assistant Examiner—Amy DeCloux
(74) *Attorney, Agent, or Firm*—Marshall, Gerstein & Borun

(57) ABSTRACT

The invention provides polynucleotides isolated from cDNA libraries of human fetal liver-spleen and macrophage as well as polypeptides encoded by these polynucleotides and mutants or variants thereof. The polypeptides correspond to a human CD39-like protein. Other aspects of the invention include vectors containing polynucleotides of the invention and related host cells as well a processes for producing CD39-like polypeptides, and antibodies specific for such polypeptides.

11 Claims, 11 Drawing Sheets

OTHER PUBLICATIONS

Figure 7:
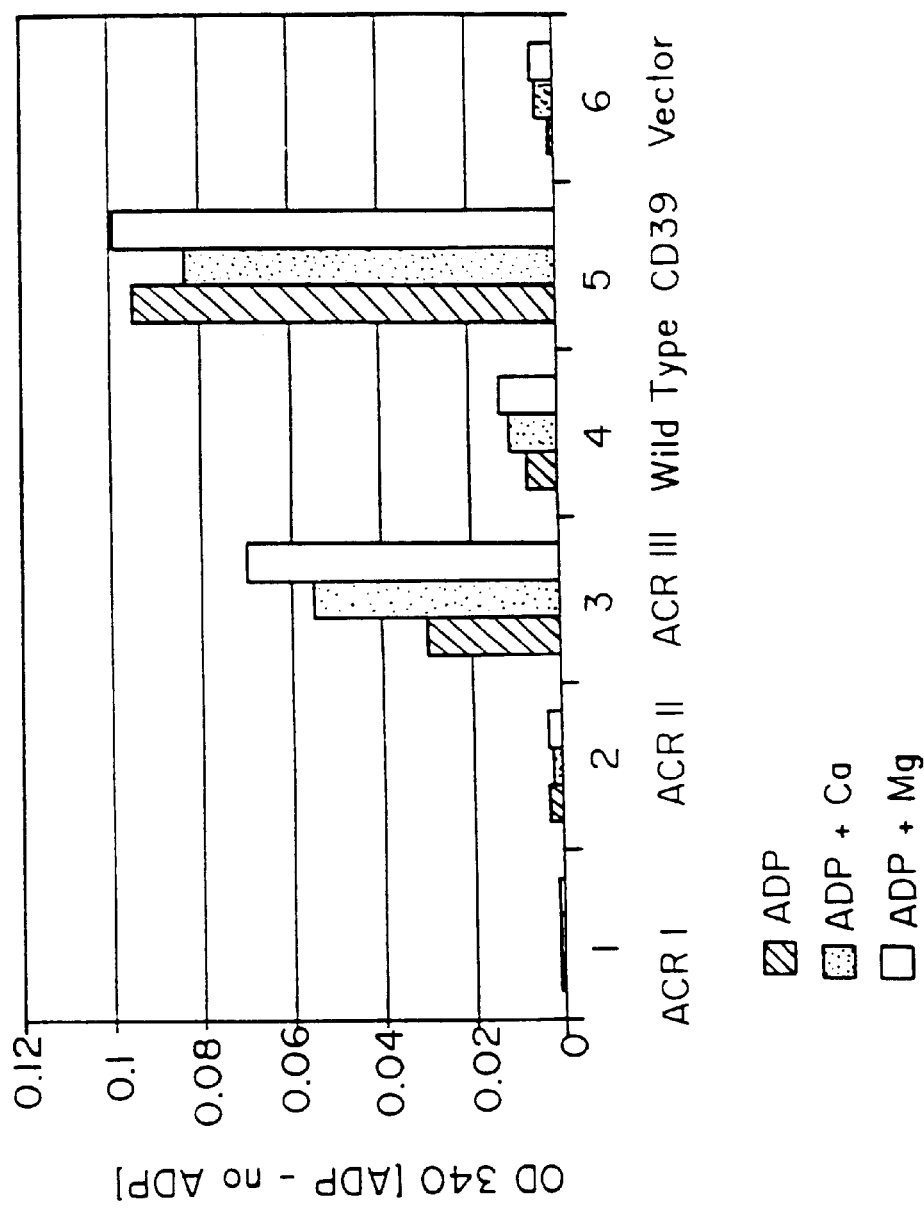

Moore, D., et al. "Regional and cellular distribution of the P2Y(1) purinergic receptor in the human brain: striking neuronal localisation," *J. Comp. Neurol.*, 421(3):374–84 (2000).

Sneddon. D., et al., "Modulation of purinergic neurotransmission." *Prog. Brain. Res.*, 120:11–20 (1999).

Hicks–Berger, C.A., et al., "Expression and Characterization of soluble and Membrane–bound Human Nucleoside Triphosphate Diphosphohydrolase 6 (CD39L2)," *J. Biol. Chem.*, 275(44): 34041–34045 (2000).

Enjyoji, et al., "Targeted disruption of cd39/ATP diphosphohydrolase results in disordered homeostasis and thromboregulation," *Nature Medicine* 5(9): 1010–1017 (1999).

Adelman, J. P. et al., "In Vitro Deletional Mutagenesis for Bacterial Production of the 20,000–Dalton Form of Human Pituitary Growth Hormone," *DNA*, 2(3):183–193 (1983).

Altshcul, S.F. et al., "Basic Local Alignment Search Tool," *J. Mol. Biol.*, 215:403–410 (1990).

Altschul, S.F., "A Protein Alignment Scoring System Sensitive at All Evolutionary Distances," *J. Mol. Evol.*, 36:290–300 (1993).

Anderson, W.F., "Human Gene Therapy," *Nature (Supp.)*, 392:25–30 (1998).

Asseline, U. et al., "Nucleic Acid–Binding Molecules with High Affinity and Base Sequence Specificity: Intercalating Agents Covalently Linked to Oligodeoxynucleotides," *Proc. Natl. Acad. Sci., USA*, 81: 3297–3301 (1984).

Bayer, E.A. et al., "The Avidin–Biotin Complex in Affinity Cytochemistry," *Meth. Enzym.*, 62:308–315 (1979).

Beal, P.A. et al., "Second Structural Motif for Recognition of DNA by Oligonucleotide–Directed Triple–Helix Formation," *Science*, 251:1360–1363 (1991).

Bonaldo, M. et al., "Normalization and Subtraction: Two Approaches to Facilitate Gene Discovery," *Genome Res.*, 6:791–806 (1996).

Boorstein et al., "Primer Extension Analysis of RNA," *Methods Enzymol.*, 180:347–369 (1989).

Breslauer, K.J. et al., "Predicting DNA Duplex Stability from the Base Sequence," *Proc. Natl. Acad. Sci., USA*, 83: 3746–3750 (1986).

Broude, N.E. et al., "Enhanced DNA Sequencing by Hybridization," *Proc. Natl. Acad. Sci., USA*, 91: 3072–3076 (1994).

Brumbaugh, J.A. et al, "Continuous, On–line DNA Sequencing Using Oligonucleotide Primers with Multiple Fluorophores," *Proc. Natl. Acad. Sci., USA*, 85:5610–5614 (1988).

Burnstock, G., "The Past, Present and Future of Purine Nucleotides as Signalling Molecules," *Neuropharmacology*, 36:1127–1139 (1997).

Cate, R.L. et al. "Genomic Southern Analysis with Alkaline–Phosphatase–Conjugated Oligonucleotide Probes and the Chemiluminescent Substrate AMPPD," *Genet. Anal. Tech. Appl.*, 8(3):102–106 (1991).

Chadwick, B. P. et al., "Cloning and Mapping of a Human and Mouse Gene with Homology to Ecto–ATPase Genes," *Mammalian Genome*, 8:668–672 (1997).

Chadwick, B.P. et al. "cDNA Cloning and Chromosomal Mapping of a Mouse Gene with Homology to NTPases," *Mammalian Genome*, 9:162–164 (1998).

Chadwick B.P. et al., "The CD39–like Gene Family: Identification of Three New Human Members (CD36L2, CD39L3, and CD39L4), Their Murine Homologues, and a Member of the Gene Family from *Drosophila melanogaster*," *Genomics*, 50:357–367 (1998).

Cole, S.P.C. et al., "The EVB–Hybridoma Technique and It's Application to Human Lung Cancer," *Monoclonal Antibodies and Cancer Therapy*, Alan R. Liss, Inc., pp. 77–96 (1985).

Communi, D. et al., "Cloning, Functional Expression and Tissue Distribution of the Human $P2Y_6$ Receptor," *Biochem. Biophys. Res. Com.*, 222:.303–308 (1996).

Cooney, M. et al., "Site–Specific Oligonucleotide Binding Represses Transcription of the Human c–myc Gene in Vitro," *Science*, 15241:456–459 (1988).

Craig, M.E. et al., "Relaxation Kinetics of Dimer Formation by Self Complementary Oligonucleotides," *J. Mol. Biol.*, 62:383–401 (1971).

Dahlén et al., "Sensitive Detection of Genes by Sandwich Hybridization and Time–Resolved Fluorometry," *Mol. Cell. Probes (England)*, 1:159–168 (1987).

Daly, J. et al., "Direct Method for Determining Inorganic Phosphate in Serum with the CentrifiChem", *Clin. Chem.*, 18:263–265 (1972).

Dolinnaya, N.G. et al., "Site–directed Modification of DNA Duplexes by Chemical Ligation," *Nucleic Acids Research, (England)*, 16(9):3721–3738 (1988).

Dolinnaya, N.G. et al., "The use of BrCN for assembling modified DNA duplexes and DNA–RNA hybrids; comparison with water–soluble carbodiimide," *Nucleic Acids Res. (England)*, 19(11):3067–72 (1991).

Drmanac, R. et al., "A calculation of fragment lengths from human DNA with 78 restriction enzymes: an aid for cloning and mapping," *Nucleic Acids Research*, 14(11): 4691–4692 (1986).

Drmanac, R et al., Sequencing of Megabase Plus DNA by Hybridization: Theory of the Method, *Genomics*, 4:114–128 (1989).

Drmanac, R. et al., "Reliable Hybridization of Oligonucleotides as Short as Six Nucleotides," *DNA Cell Biol.*, 9:527–534 (1990).

Drmanac, R. et al., "An Algorithm for the DNA Sequence Generation from k–Tuple Word Contents of the Minimal Number of Random Fragments," *J. Biomol. Struct. Syn.*, 8(5):1085–1102 (1991).

Drmanac, R. et al., "Sequencing By Oligonucleotide Hybridization: A Promising Framework in Decoding of the Genome Program?" *Proceedings of the First International Conference Electrophoresis Supercomputing Human Genome*, Cantor et al., (Eds.), World Scientific Publishing Co., Singapore, pp. 47–59 (1991).

Drmanac, R. et al., "W (A or T) Sequences as Probes and Primers Suitable for Genomic Mapping and Fingerprinting," *Nucleic Acids Research*, 19(21):5839–5842 (1991).

Drmanac, R. et al., "DNA Sequence Determination by Hybridization: A Strategy for Efficient Large–Scale Sequencing," *Science*, 260(5114):1649–1652 (1993).

Drmanac, S. et al., "Processing of cDNA and Genomic Kilobase–Size Clones for Massive Screening, Mapping and Sequencing by Hybridization," *Biotechniques*, 17:328–329, 332–336 (1994).

Dubyak, G. R. et al., "Signal Transduction via $P_2$–Purinergic Receptors for Extrecellular ATP and Other Nucleotides," *Am. J. Physiol.* 34:C577–C606 (1993).

Duncan, C.H. et al., "Affinity Chromatography of a Sequence–Specific DNA Binding Protein using Teflon–linked Oligonucleotides," *Anal. Biochem.*, 169:104–108 (1988).

Engval, E. et al., Enzyme–Linked Immunosorbent Assay, ELISA III. Quantitation of Specific Antibodies by Enzyme–Labeled Anti–Immunoglobulin in Antigen–Coated Tubes, *Immunol.*, 109:129–135 (1972).

Fischer Y. et al., "Purinergic Inhibition of Glucose Transport in Cardiomyocytes," *J. Biol. Chem.*, 274:755–761 (1999).

Friedmann, T., "Progress Toward Human Gene Therapy," *Science*, 244: 1275–1281 (1989).

Gayle III, R.B. et al., "Inhibition of Platelet Function by Recombinant Soluble Ecto–ADPase/CD39," *J. Clinical Investigation*, 101(9):1851–1859 (1998).

Gluzman, Y., "SV40–Transformed Simian Cells Support the Replication of Early SV40 Mutants," *Cell*, 23:175–182 (1981).

Goding, J.W., "Conjugation of Antibodies with Fluorochromes: Modifications to the Standard Methods," *J. Immunol. Meth.*, 13: 215–226 (1976).

Gouttefangeas, C. et al., "The CD39 Molecule Defines Distinct Cytotoxic Subsets within Alloactivated Human CD8–Positive Cells," *Eur. J. Immunol.*, 22:2681–2685 (1992).

Hillenkamp, F. et al., "Matrix Assisted UV–Laser Desorption/Ionization: A New Approach to Mass Spectrometry of Large Biomolecules," in: *Biological Mass Spectrometry*, Burlingame et al., (eds.), Elsvier Science Pub., Amsterdam, p. 49–60 (1990).

Hoheisel et al., "Quantitative Measurements on the Duplex Stability of 2,6–Diaminopurine and 5–Chloro–Uracil Nucleotides using Enzymatically Synthesized Oligomers," *FEBS Lett*, 274:103–106 (1990).

Hurby et al., "Application of Synthetic Peptides: Antisense Peptides," In *Synthetic Peptides, A User's Guide*, W.H. Freeman, NY, pp. 289–307 (1992).

Huth–Fehre, T. et al., "Matrix Assisted Laser Desorption Mass Spectrometry of Oligodeoxythymidylic Acids," *Rapid Comm. Mass Spect.*, 6:209–213 (1992).

Ikuta, S. et al., "Dissociation Kinetics of 19 Base Paired Oligonucleotide–DNA Duplexes Containing Different Single Mismatched Base Pairs," *Nucleic Acids Research*, 15:797–811 (1987).

Inouye, S. et al., "Microplate Hybridization of Amplified Viral DNA Segment," *J. Clin. Microbiol.*, 28:1469–1472 (1990).

Kaczmarek, E. et al., "Identification and Characterization of CD39/Vascular ATP Diphosphohydrolase," *J. Biol. Chem.*, 271:33116–33122 (1996).

Kansas, G. S. et al., "Expression, Distribution, and Biochemistry of Human CD39 Role in Activation–Associated Homotypic Adhesion of Lymphocytes," *J. Immunol.*, 146:2235–2244 (1991).

Kasprzak, A. et al., "Location of a Contact Site between Actin and Myosin in the Three–Dimensional Structure of the Acto–S1 Complex," *Biochemistry*, 28:9230–9238 (1989).

Kirley, T.L., "Complementary DNA Cloning and Sequencing of the Chicken Muscle Ecto–ATPase," *J. Biol. Chem.*, 272:1076–1081 (1997).

Kohler, G. et al., "Continuous Cultures of Fused Cells Secreting Antibody of Predefined Specificity," *Nature*, 256:495–497 (1975).

Kozbor, D. et al., "The Production of Monoclonal Antibodies from Human Lymphocytes," *Immunology Today*, 4:72–79 (1983).

Lamture, J., "Direct Detection of Nucleic Acid Hybridization on the Surface of a Charge Coupled Device," *Nucleic Acids Research*, 22:2121–2125 (1994).

Landegren, U. et al., "A Ligase–Mediated Gene Detection Technique," *Science*, 241:1077–1080 (1988).

Lee, J.S. et al., "Complexes formed by (pyrimidine)$_n$ (purine)$_n$ DNAs on lowering the pH are three–stranded," *Nucl. Acids Res.*, 6:3073–3091 (1979).

Lehrach, H. et al., "Hybridization Fingerprinting in Genome Mapping and Sequencing," in: *Genome Analysis vol. 1: Genetic and Physical Mapping*, Cold Spring Harbor Laboratory Press, pp. 39–81 (1990).

Lutz, Y. et al., "The Distribution of Two hnRNP–Associated Proteins Defined by a Monoclonal Antibody Is Altered in Heat–Shocked HeLa Cells," *Exp. Cell Research.*, 175:109–124 (1988).

Makita, K. et al., "Placental ecto–ATP diphosphohydrolase: its structural feature distinct from CD39, localization and inhibitin on shear–induced platelet aggregation," *International J. Hematology*, 68:297–310 (1998).

Maliszewski, C. R. et al., "The CD39 Lymphoid Cell Activation Antigen," *J. Immunology*, 153:3574–3583 (1994).

Marcus, A.J. et al., "The Endothelial Cell Ecto–ADPase Responsible for Inhibition of Platelet Function is CD39," *J. Clinical Investigation*, 99(6): 1351–1360 (1997).

Miller, A.D., "Human Gene Therapy Comes of Age," *Nature*, 357:455–460 (1992).

Morrisey, D. et al., "Nucleic Acid Hybridization Assays Employing dA–Tailed Capture Probes. I. Single Capture Methods," *Mol. Cell. Probes*, 2:189–207 (1989).

Mulero, J.J. et al., "CD39–L4 Is a Secreted Human Apyrase, Specific for the Hydrolysis of Nucleoside Diphosphates," *J. Biol. Chem.*, 274(29):20064–20067 (1999).

Murakami, A. et al., "Fluorescent–Labeled Oligonucleotide Probes : Detection of Hybrid Formation in Solution by Fluorescence Polarization Spectroscopy," *Nucleic Acids Res.*, (England), 19:4097–102 (1991).

Nagata, Y. et al., "Quantification of Picogram Levels of Specific DNA Immobilized in Microtiter Wells," *FEBS Lett* (*NETHERLANDS*), 183: 379–382 (1985).

Neumann, P.E. et al., "Mapping of Tow Genes that Influence Susceptibility to Audiogenic Seizures in Crosses of C57BL/6J and DBA/2J Mice," *Behavior Genetics*, 20:307–323 (1990).

Nichols, R. et al. "A Universal Nucleoside for Use at Ambiguous Sites in DNA Primers," *Nature*, 369:492–493 (1994).

Nizetic, D. et al., "An Improved Bacterial Colony Lysis Procedure Enables Direct DNA Hybridisation Using Short (10, 11 bases) Oligonucleotides to Cosmids," *Nucleic Acids Research*, 19:182 (1991).

Okano, H. et al., "Myelin Basic Protein Gene and the Function of Antisense RNA in Its Repression in Myelin–Deficient Mutant Mouse," *J. Neurochem.*, 56:560–567 (1991).

Ottman, R. et al., "Localization of a Gene for Partial Epilepsy to Chromosome 10q," *Nature Genet.*, 10:56–60 (1995).

Paterson, B.M. et al., "Structural Gene Identification and Mapping by DNA–mRNA Hybrid–Arrested Cell–Free Translation," *Proc. Natl. Acad. Sci.*, 74:4370–4374 (1977).

Paunesku, T. et al., "Origin of Rat β–Globin Haplotypes Containing Three and Five Genes," *Mol. Biol. Evol.*, 7:407–422 (1990).

Pease, A.C. et al., "Light–generated Oligonucleotide Arrays for Rapid DNA Sequence Analysis," *Proc. Natl. Acad. Sci., USA*, 91:5022–5026 (1994).

Pevzner, P.A., "1–Tuple DNA Sequencing: Computer Analysis," *J. Biomol. Sruct. & Dyn.*, 7(1):63–73 (1989).

Pontius, B.W. et al., "Rapid Renaturation of Complementary DNA Strands Mediated by Cationic Detergents: A Role for High–Probability Bindiong Domains in Enhancing the Kinetics of Molecular Assembly Processes,"*Proc. Natl. Acad. Sci.,USA*, 88:8237–8241 (1991).

Pörshke, D. et al., "Co–operative Non–enzymic Base Recognition," *J. Mol. Biol.*, 62:361–381 (1971).

Rasmussen, S.R. et al., "Covalent Immobilization of DNA onto Polystyrene Microwells: The Molecules Are Only Bound at the 5' End," *Anal. Biochem.*, 198:138–142 (1991).

Rowe, M. et al., "Monoclonal Antibodies to Epstein–Barr Virus–Induced, Transformation–Associated Cell Surface Antigens: Binding Patterns and Effect Upon Virus–Specific T–Cell Cytotoxicity," *Int. J. Cancer*, 29:373–381 (1982).

Sambrook, J. et al., In: *Molecular Cloning A Laboratory Manual*, 2nd Ed., Cold Springs Harbor Press, pp. 9.14–9.28 (1989).

Schoenborn, M.A. et al., "Gene Structure and Chromosome Location of Mouse Cd39 Coding for an Ecto–Apyrase," *Cytogenetics & Cell Genetics*, 81:287–289 (1998).

Schriefer, L.A. et al., "Low Pressure DNA Shearing: A Method for Random DNA Sequence Analysis," *Nucleic Acids Res.* (*ENGLAND*), 18 (24):7455–6 (1990).

Schubert, F. et al., "One–step Labelling of Oligonucleotides with Fluoresceine During Automated Synthesis," *Nucleic Acids Res.* (*ENGLAND*), 18:3427 (1990).

Schulman E. S. et al., "ATP Modulates Anti–IgE–Induced Release of Histamine from Human Lung Mast Cells," *Am. J. Respir. Cell Mol. Biol.*, 20:530–537 (1999).

Seyfried, T.N. et al., "Genetic Linkage Between the AH Locus and a Major Gene that Inhibits Susceptibility to Audiogenic Seizures in Mice," *Genetics*, 99:117–126 (1981).

Skobel, E. et al., "Relation Between Enzyme Release and Irreversible Cell Injury of the Heart under the Influence of Cytoskeleton Modulating Agents," *Biochim. Biophys. Acta*, 1362:128–134 (1997).

Smith, R.D. et al., "New Developments in Biochemical Mass Spectrometry: Electrospray Ionization," *Anal. Chem.*, 62:882–899 (1990).

Smith, T.M. et al., "Cloning, Sequencing, and Expression of a Human Brain Ecto–Apyrase Related to Both the Ecto–ATPase and CD39 Ecto–Apyrases," *Biochim. Biophys Acta*, 1386:65–78 (1998).

Somers, G.R. et al., "Expression of the P2Y6 Purinergic Receptor in Human T Cells Infiltrating Inflammatory Bowel Disease," *Lab. Invest.*, 78:1375–1383 (1988).

Sternberger, L.A. et al., "The Unlabeled Antibody Enzyme Method of immunohistochemistry—Preparation and Properties of Soluble Antigen–Antibody Complex (Horseradish Peroxidase–Antihoreseradish Peroxidase) and Its Use in Identification of Spriochetes," *J. Histochem. Cytochem.*, 18: 315–333 (1970).

Stevanovicć, M. et al., Variant chromosomal arrangement of adult β–globin genes in rat *Gene*, 79:139–150 (1989).

Strezoska, Z. et al., "DNA Sequencing by Hybridization: 100 Bases Read by a Non–Gel–Based Method," *Proc. Natl. Acad. Sci., USA*, 88:10089–10093 (1991).

Van Ness, J. et al., "A Versatile Solid Support System for Oligodeoxynucleotide Probe–Based Hybridization Assays," *Nucleic Acids Res.*, (ENGLAND)19:3345–3350 (1991).

Verma, I.M., "Gene Therapy—Treatment of Disease by Introducing Healthy Genes into the Body is Becoming Feasible. But the Therapy will not Reach its Full Potential until the Genes Can Be Coaxed to Work throughout Life," *Scientific American*, pp. 68–72, 81–84 (1990).

Vollrath, D. et al., "The Human Y Chromosome: A 43–Interval Map Based on Naturally Occurring Deletions," *Science*, 258:52–59 (1992).

Wallace, R.B. et al., "Hybridization of Synthetic Oligodeoxyribonucleotides to $\Phi\chi 174$ DNA: The Effect of Single Base Pair Mismatch," *Nucleic Acids Research*, 6:3543–3557 (1979).

Walsh P.S. et al., "Preferential PCR Amplification of Alleles: Mechanisms and Solutions," *PCR Methods Appl*, 1:241–250 (1992).

Wang, T–F. et al., "CD39 Is an Ecto–($Ca^{2+}$, $Mg^{2+}$)–apyrase," *J. Biol. Chem.*, 271(17):9898–9901 (1996).

Wang T–F. et al., "Characterization of Brain Ecto–Apyrase: Evidence for Only One Ecto–Apyrase (CD39) Gene," *Molecular Brain Research*, 47:295–302 (1997).

Wang, T–F. et al., "Widespread Expression of Ecto–Apyrase (CD39) in the Central Nervous System," *Brain Research*, 790:318–322 (1988).

Wang T–F et al., "The Transmembrane Domains of Ectoapyrase (CD39) Affect Its Enzymatic Activity and Quarternary Structure," *J. Biol. Chem.*, 273:24818–24821 (1998).

Wells, J.A. et al., "Cassette Mutagenesis: An Efficient Method for Generation of Multiple Mutations at Defined Sites," Gene, 34:315–323 (1985).

Wolter, A. et al., "Negative Ion FAB Mass Spectrometric Analysis of Non–Charged Key Intermediates in Oligonucleotide Synthesis: Rapid Identification of Partially Protected Dinulceoside Monophates," *Biomedical Environ. Mass Spec.*, 14:111–116 (1987).

Xu, L. et al., "Ketone Electrophores and an Olefin–Release Group Electrophore–Labeled DNA Oligomer Detection via Electron Capture," *Chromatography*, 764:95–102 (1997).

Yamashita, M. et al., "Electrospray Ion Source. Another Variation on the Free–Jet Theme," *J. Phys. Chem.*, 88:4451–4459 (1984).

Zoller, M.J. et al., Oligonucleotide–Directed Mutagenesis Using M13–Derived Vectors: An Efficient and General Procedure for the Production of Point Mutations in any Fragment of DNA, *Nucleic Acids Res.*, 10:6487–6500 (1982).

Fingl et al., "General Principles," In: *The Pharmacological Basis of Therapeutics*, Chapter 1, pp. 1–46 (1975).

Geiger et al., "Ligand specificity and ticlopidine effects distinguish three human platelet ADP receptors," *European Journal Pharmacology*, 351:235–246 (1998).

Hechler et al., "ATP Derivatives Are Antagonists of the P2Y1 Receptor: Similarities to the Platelet ADP Receptor," *American Pharmacology*, 53:727–733 (1998).

Ingall et al., "Antagonists of the Platelet $P_{2T}$ Receptor: A Novel Approach to Antithrombotic Therapy," *J. Med. Chem.*, 42:213–220 (1999).

Jantzen et al., "Evidence for Two Distinct G–protein–coupled ADP Receptors Mediating Platelet Activation," *Thromb. Haemost.*, 81:111–117 (1999).

Myers et al., "Automated Double–Label: In Situ Hybridization and Immunohistochemistry," *J. Surg Path.*, 1:191–203 (1995).

Vigne et al., "Benzoyl ATP Is an Antagonist of Rat and Human P2Y1 Receptors and of Platelet Aggregation," *Biochem. Biophys. Res. Commun.*, 156:94–97 (1999).

* cited by examiner

SEQ ID NO: 1:
GGCATATTAGCTTGGGTTACTGTGAATTTTCTGACAGGTCAGCTGCATGGCCACAGA
CAGGAGACTGTGGGGACCTTGGACCTAGGGGAGCCTCCACCCAAATCACGTTCCTG
CCCCAGTTTGAGAAAACTCTGGAACAAACTCCTAGGGGCTACCTCACTTCCTTTGAG
ATGTTTAACAGCACTTATAAGCTCTATACACATAGTTACCTGGGATTTGGATTGAAA
GCTGCAAGACTAGCAACCCTGGGAGCCCTGGAGACAGAAGGGACTGATGGGCACACT
TTCCGGAGTGCCTGT

SEQ ID NO: 2:
GCGGGCTGCCGCGCAAGGGTGGCGCGCGCGTTTTCCTTGTTCCTGGTCAACAAAG
AAATGTGGAGTGTCTTGGCTGAATCCTCATACAGACAAGATCATTATGGTGCTGTTA
GGTTGAAAAAGTGATATAATAAAGGAACCAAGGAGAAAATTCAGAAGGAAAGAAAAA
ATTGCCTCTGCAGGTGTGCGAGCAGGATTGCTTCTGCAACAAAAGCCTCCACCCAGC
CACATCTTGGGAAAAGAATGGCCACTTCTTGGGGCACAGTCTTTTTCATGCTGGTGG
TATCCTGTGTTTGCAGCGCTGTCTCCCACAGGAACCAGCAGACTTGGTTTGAGGGTA
TCTTCCTGTCTTCCATGTGCCCCATCAATGTCAGCGCCAGCACCTTGTATGGAATTA
TGTTTGATGCAGGGAGCACTGGAACTCGAATTCATGTTTACACCTTTGTGCAGAAAA
TGCCAGGACAGCTTCCAATTCTAGAAGGGGAAGTTTTGATTCTGTGAAGCCAGGA
CTTTCTGCTTTTGTAGATCAACCTAAGCAGGGTGCTGAGACCGTTCAAGGGCTCTTA
GAGGTGGCCAAAGACTCAATCCCCGAAGTCACTGGAAAAGACCCCAGTGGTCCTA
AAGGCAACAGCAGGACTACGCTTACTGCCAGAACACAAAGCCAAGGCTCTGCTCTTT
GAGGTAAAGGAGATCTTCAGGAAGTCACCTTTCCTGGTACCAAAGGGCAGTGTTAGC
ATCATGGATGGATCCGACGAAGGCATATTAGCTTGGGTTACTGTGAATTTTCTGACA
GGTCAGCTGCATGGCCACAGACAGGAGACTGTGGGGACCTTGGACCTAGGGGAGCC
TCCACCCAAATCACGTTCCTGCCCCAGTTTGAGAAAACTCTGGAACAAACTCCT
AGGGGCTACCTCACTTCCTTTGAGATGTTTAACAGCACTTATAAGCTCTATACACAT
AGTTACCTGGGATTTGGATTGAAAGCTGCAAGACTAGCAACCCTGGGAGCCCTGGAG
ACAGAAGGGACTGATGGGCACACTTTCCGGAGTGCCTGTTTACCGAGATGGTTGGAA
GCAGAGTGGATCTTTGGGGGTGTGAAATACCAGTATGGTGGCAACCAAGAAGGGGAG
GTGGGCTTTGAGCCCTGCTATGCCGAAGTGCTGAGGGTGGTACGAGGAAAACTTCAC
CAGCCAGAGGAGGTCCAGAGAGGTTCCTTCTATGCTTTCTCTTACTATTATGACCGA
GCTGTTGACACAGACATGATTGATTATGAAAGGGGGTATTTTAAAAGTTGAAGAT
TTTGAAAGAAAAGCCAGGGAAGTGTGTGATAACTTGGAAAACTTCACCTCAGGCAGT
CCTTTCCTGTGCATGGATCTCAGCTACATCACAGCCCTGTTAAAGGATGGCTTTGGC
TTTGCAGACAGCACAGTCTTACAGCTCACAAAGAAAGTGAACAACATAGAGACGGGC
TGGGCCTTGGGGGCCACCTTTCACCTGTTGCAGTCTCTGGGCATCTCCCATTGAGGC
CACGTACTTCCTTGGAGACCTGCATTTGCCAACACCTTTTTAAGGGGAGGAGAGAGC
ACTTAGTTTCTGAACTAGTCTGGGGACATCCTGGACTTGAGCCTAGAGATTWRGTTA
ATTAASCGGCCGAGCTTATCCTTWATRAGGTAATTTACTTCMTGGCCGCGTTTACAC
GTCGTGATGGNAAACCTGCGTCCAACTAACGCTTGASAMATCCCCTTCGCAGCTGC
GATACCAAAAGCCGACGACGCCTTCCACAGTGCCA

Figure 1

SEQ ID NO: 3:
MATSWGTVFFMLVVSCVCSAVSHRNQQTWFEGIFLSSMCPINVSASTLYGIMFDAGS
TGTRIHVYTFVQKMPGQLPILEGEVFDSVKPGLSAFVDQPKQGAETVQGLLEVAKDS
IPRSHWKKTPVVLKATAGLRLLPEHKAKALLFEVKEIFRKSPFLVPKGSVSIMDGSD
EGILAWVTVNFLTGQLHGHRQETVGTLDLGGASTQITFLPQFEKTLEQTPRGYLTSF
EMFNSTYKLYTHSYLGFGLKAARLATLGALETEGTDGHTFRSACLPRWLEAEWIFGG
VKYQYGGNQEGEVGFEPCYAEVLRVVRGKLHQPEEVQRGSFYAFSYYYDRAVDTDMI
DYEKGGILKVEDFERKAREVCDNLENFTSGSPFLCMDLSYITALLKDGFGFADSTVL
QLTKKVNNIETGWALGATFHLLQSLGISH

Figure 2

```
CD39Human.seq   MEDTKESNVKTFCSKNILAILGESSIIAVIALLA--VGLT    38
246 prot        MATSWGTVF---------FMLVVSCVCSAVSHRNQQTWFEGIF   34

CD39Human.seq   QNK---ALPENVKYGIVLDAGSSHTSLYIYKWPAEKEND      74
246 prot        LSMCPINVSASTLYGIMFDAGSTGTRIHVYTFVQKMPGQ      74

CD39Human.seq   TGVVHQVEECRVKGPGISKFVQKVNEIGIYLTDCMERARE    114
246 prot        LPILEGEVFDSVK-PGLSAFVDQPKQGAETVQGLLEVAKD    113

CD39Human.seq   VIPRSQHQETPVYLGATAGMRLLRMESEELADRVLDVVER    154
246 prot        SIPRSHWKKTPVVLKATAGLRLL---PEHKAKALLFEVKE    150

CD39Human.seq   SLSNYPFDFQ--GARIITGQEEGAYGWITINYLLGKFSQK    192
246 prot        IFRKSPFLVPKGSVSIMDGSDEGILAWTVNFLTGQL---    187

CD39Human.seq   TRWFSIVPYETNNQETFGALDLGGASTQVTFVPQ-NQTIE    231
246 prot        ------HGHRQETVGTLDLGGASTQITFLPQFEKTLE    218

CD39Human.seq   SPDNA--LQFRLYGKDYNVYTHSFLCYGKDQALWQKLAKD    269
246 prot        QTPRGYLTSFEMFNSTYKLYTHSYLGFGLKAA--RLATL    255

CD39Human.seq   IQVASNEILRDPCFHPGYKKVVNSDLYKTPCTKR-FEMT    308
246 prot        GALETEG-----------TDGHTFRSACLPRWLEAE    280
```

FIG. 3A

| | | |
|---|---|---|
| CD39Human.seq | LPFQQF-----EIQGIGNYQQCHQSILELFNTSYCPYSQ | 342 |
| 246 prot | WIFGGVKYQYGGNQEGEVGFEPCYAEVLRVVRGK----- | 314 |
| CD39Human.seq | CAFNGIFLPPLQGDFGAFSAF--YFVMKELNLTSEKVSQE | 380 |
| 246 prot | ----LHQPEEVQRGSFYAEFSYYYDR---AVDTDMIDYE | 345 |
| CD39Human.seq | KVTEM-MKKFCAQPWE--EIKTSYAGVKEKYLSEYCFSGT | 417 |
| 246 prot | KGGILKVEDFERKAREVCDNLENFTSGSP-FL---CMDLS | 381 |
| CD39Human.seq | YILSLLQGYHFTADSWEHIHFIGKIQGSDAGWTLGYMLN | 457 |
| 246 prot | YITALLKDGFGFADST--VLQLTKKVNNIETGWALGATFH | 419 |
| CD39Human.seq | LTNMIPAEQPLSTPLSHSTYVFLMVLFSLVLFTVAIIGLL | 497 |
| 246 prot | LLQSLGISH | 428 |
| CD39Human.seq | IFHKPSYFWKDMV | 510 |
| 246 prot | | 428 |

FIG. 3B

```
  1  M A T S W G T V F F M L V V S C V C S A V S H R N Q Q T W F E G I F L S S M C P   246 prot
  1  M A T S W G A V F - M L I I A C V G S T V F Y R E Q Q T W F E G V F L S S M C P   mur ntpase 41  I N V S A S T L Y G I M F D A G S T G T R I H V Y T F V Q K M P G Q L P I L E G   246 prot
 40  I N V S A G T F Y G I M F D A G S T G T R I H V Y T F V Q K T A G Q L P F L E G   mur ntpase 81  E V F D S V K P G L S A F V D Q P K Q G A E T V Q G L L E V A K D S I P R S H W   246 prot
 80  E I F D S V K P G L S A F V D Q P K Q G A E T V Q E L L E V A K D S I P R S H W   mur ntpase 121  K K T P V V L K A T A G L R L L P E H K A K A L L E V K E I F R K S P F L V P     246 prot
120  E R T P V V L K A T A G L R L L P E Q K A Q A L L E V E E I F K N S P F L V P     mur ntpase 161  K G S V S I M D G S D E G I L A W V T V N F L T G Q L H G H R Q E T V G T L D L   246 prot
160  D G S V S I M D G S Y E G I L A W V T V N F L T G Q L H G R G Q E T V G T L D L   mur ntpase 201  G G A S T Q I T F L P Q F E K T L E Q T P R G Y L T S F E M F N S T Y K L Y T H   246 prot
200  G G A S T Q I T F L P Q F E K T L E Q T P R G Y L T S F E M F N S T F K L Y T H   mur ntpase
```

FIG. 4A

```
241 SYLGFGLKAARLATLGALETEGTDGHTFRSACLPRWLEAE      246 prot
240 SYLGFGLKAARLATLGALEAKGTDGHTFRSACLPRWLEAE      mur ntpase 281 WIFGGVKYQYGGNQEGEVGFEPCYAEVLRVVRGKLHQPEE      246 prot
280 WIFGGVKYQYGGNQEGEMGFEPCYAEVLRVVQGKLHQPEE      mur ntpase 321 VQRGSFYAFSYYYDRAVDTDMIDYEKGGILKVEDFERKAR      246 prot
320 VRGSAFYAFSYYYDRAADTHLIDYEKGGVLKVEDFERKAR      mur ntpase 361 EVCDNLENFTSGSPFLCMDLSYITALLKDGFADSTVLQ         246 prot
360 EVCDNLGSFSSGSPFLCMDLTYITALLKDGLGFAERHPLT       mur ntpase 401 LTKKVNNIETGW-ALGATF------HLLQSLGISH            246 prot
400 -AHKESEQHRDWLGLGGHLSPAPVSGHHQLRPSSTSEACI       mur ntpase 428                                                246 prot
439 SEPVFSQEGVDSETFSDLSGKAWPETR                    mur ntpase
```

FIG. 4B

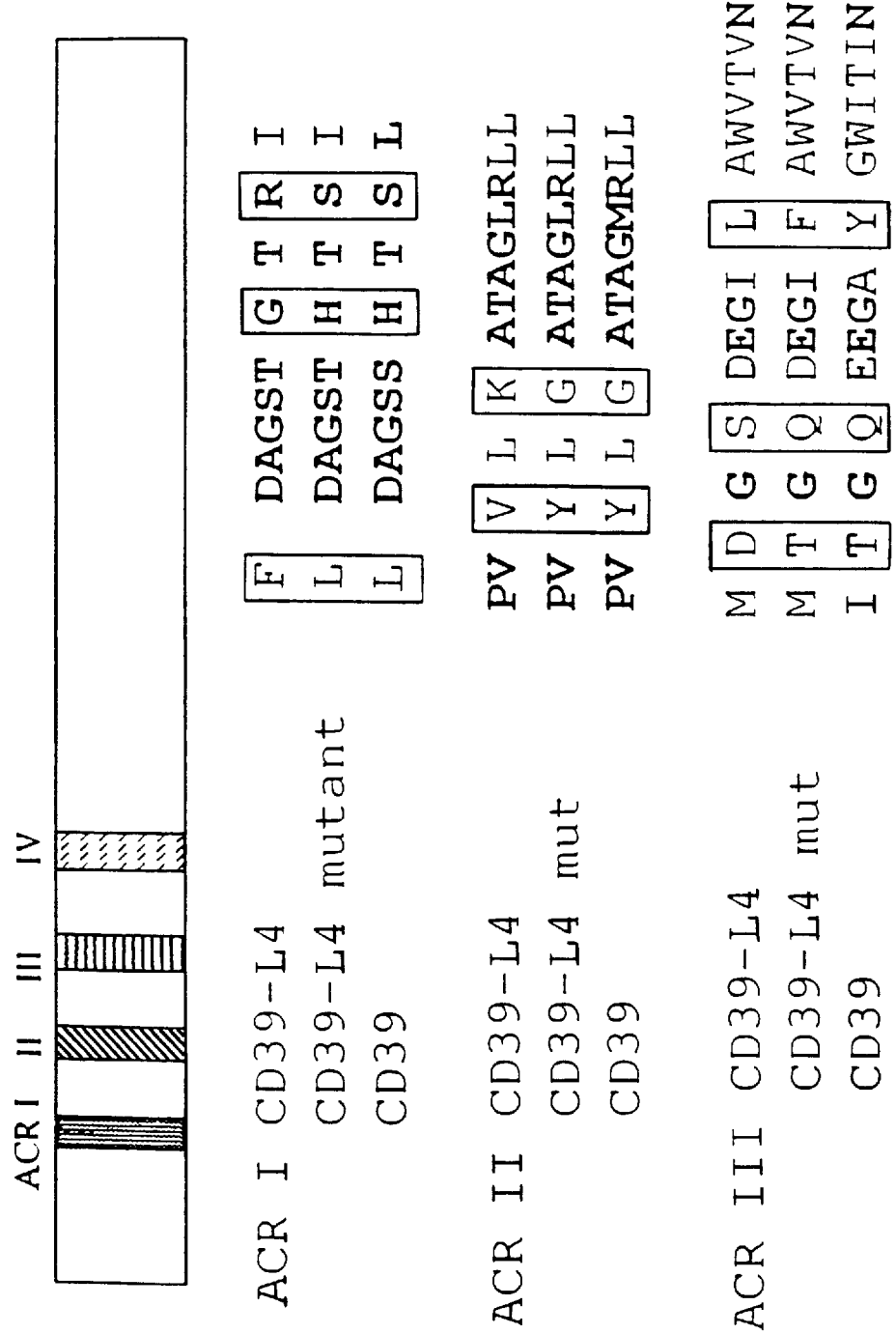

SEQ ID NO: 6:
ATGGCCACTTCTTGGGGCACAGTCTTTTTCATGCTGGTGGTATCCTGTGTTTGCAGCGCTGTCT
CCCACAGGAACCAGCAGACTTGGTTTGAGGGTATCTTCCTGTCTTCCATGTGCCCCATCAATGT
CAGCGCCAGCACCTTGTATGGAATTATGTTTGATGCAGGGAGCACTGGAACTCGAATTCATGTT
TACACCTTTGTGCAGAAAATGCCAGGACAGCTTCCAATTCTAGAAGGGGAAGTTTTTGATTCTG
TGAAGCCAGGACTTTCTGCTTTTGTAGATCAACCTAAGCAGGGTGCTGAGACCGTTCAAGGGCT
CTTAGAGGTGGCCAAAGACTCAATCCCCCGAAGTCACTGGAAAAAGACCCCAGTGGTCCTAAAG
GCAACAGCAGGACTACGCTTACTGCCAGAACACAAAGCCAAGGCTCTGCTCTTTGAGGTAAAGG
AGATCTTCAGGAAGTCACCTTTCCTGGTACCAAAGGGCAGTGTTAGCATCATGACTGGACAAGA
CGAAGGCATATTCGCTTGGGTTACTGTGAATTTTCTGACAGGTCAGCTGCATGGCCACAGACAG
GAGACTGTGGGGACCTTGGACCTAGGGGGAGCCTCCACCCAAATCACGTTCCTGCCCCAGTTTG
AGAAAACTCTGGAACAAACTCCTAGGGGCTACCTCACTTCCTTTGAGATGTTTAACAGCACTTA
TAAGCTCTATACACATAGTTACCTGGGATTTGGATTGAAAGCTGCAAGACTAGCAACCCTGGGA
GCCCTGGAGACAGAAGGGACTGATGGGCACACTTTCCGGAGTGCCTGTTTACCGAGATGGTTGG
AAGCAGAGTGGATCTTTGGGGGTGTGAAATACCAGTATGGTGGCAACCAAGAAGGGGAGGTGGG
CTTTGAGCCCTGCTATGCCGAAGTGCTGAGGGTGGTACGAGGAAAACTTCACCAGCCAGAGGAG
GTCCAGAGAGGTTCCTTCTATGCTTTCTCTTACTATTATGACCGAGCTGTTGACACAGACATGA
TTGATTATGAAAAGGGGGGTATTTTAAAAGTTGAAGATTTTGAAAGAAAAGCCAGGGAAGTGTG
TGATAACTTGGAAAACTTCACC TCAGGCAGTCCTTTCCTGTGCATGGATCTCAGCTACATCAC
AGCCCTGTTA AAGGATGGCTTTGGCTTTGCAGACAGCACAGTCTTACAGCTCACAAAGAAAGT
GAAC AACATAG AGACGGGCTGGGCCTTGGGGGCCACCTTTCACCTGTTGCAGTCTCTGGGCA
TCTCCCATTGA

SEQ ID NO: 7:
MATSYGTVFFMLVVSCVCSAVSHRNQQTWFEGIFLSSMCPINVSASTLYGIMFDAGSTGT
RIHVYTFVQKMPGQLPILEGEVFDSVKPGLSAFVDQPKQGAETVQGLLEVAKDSIPRSHW
KKTPVVLKATAGLRLLPEHKAKALLFEVKEIFRKSPFLVPKGSVSIMTGQDEGIFAWVTV
NFLTGQLHGHRQETVGTLDLGGASTQITFLPQFEKTLEQTPRGYLTSFEMFNSTYKLYTH
SYLGFGLKAARLATLGALETEGTDGHTFRSACLPRWLEAEWIFGGVKYQYGGNQEGEVGF
EPCYAEVLRVVRGKLHQPEEVQRGSFYAFSYYYDRAVDTDMIDYEKGGILKVEDFERKAR
EVCDNLENFTSGSPFLCMDLSYITALLKDGFGFADSTVLQLTKKVNNIETGWALGATFHL
LQSLGISH

SEQUENCE LISTING

```
<160> NUMBER OF SEQ ID NOS:  54

<210> SEQ ID NO 1
<211> LENGTH: 300
<212> TYPE: DNA
<213> ORGANISM: Homo sapiens

<400> SEQUENCE: 1
ggcatattag cttgggttac tgtgaatttt ctgacaggtc agctgcatgg ccacagacag      60
gagactgtgg ggaccttgga cctagggga gcctccaccc aaatcacgtt cctgccccag     120
tttgagaaaa ctctggaaca aactcctagg ggctacctca cttcctttga gatgtttaac     180
agcacttata agctctatac acatagttac ctgggatttg gattgaaagc tgcaagacta     240
gcaaccctgg gagccctgga gacagaaggg actgatgggc acactttccg gagtgcctgt     300

<210> SEQ ID NO 2
<211> LENGTH: 1799
<212> TYPE: DNA
<213> ORGANISM: Homo sapiens
<220> FEATURE:
<221> NAME/KEY: CDS
<222> LOCATION: (246)..(1529)
<221> NAME/KEY: misc_feature
<222> LOCATION: (1718)
<223> OTHER INFORMATION: n = adenine or guanine or cytosine or thymidine

<400> SEQUENCE: 2
gcgggctgcc gcgcaagggt ggcgcgcgcg cgttttcctt gttcctggtc aacaaagaaa      60
tgtggagtgt cttggctgaa tcctcataca gacaagatca ttatggtgct gttaggttga     120
aaaagtgata taataaagga accaaggaga aaattcagaa ggaaagaaaa aattgcctct     180
gcaggtgtgc gagcaggatt gcttctgcaa caaaagcctc cacccagcca catcttggga     240 aaaga atg gcc act tct tgg ggc aca gtc ttt ttc atg ctg gtg gta tcc     290
      Met Ala Thr Ser Trp Gly Thr Val Phe Phe Met Leu Val Val Ser
        1               5                  10                 15 tgt gtt tgc agc gct gtc tcc cac agg aac cag cag act tgg ttt gag       338
Cys Val Cys Ser Ala Val Ser His Arg Asn Gln Gln Thr Trp Phe Glu
                 20                  25                  30 ggt atc ttc ctg tct tcc atg tgc ccc atc aat gtc agc gcc agc acc       386
Gly Ile Phe Leu Ser Ser Met Cys Pro Ile Asn Val Ser Ala Ser Thr
             35                  40                  45 ttg tat gga att atg ttt gat gca ggg agc act gga act cga att cat       434
Leu Tyr Gly Ile Met Phe Asp Ala Gly Ser Thr Gly Thr Arg Ile His
         50                  55                  60 gtt tac acc ttt gtg cag aaa atg cca gga cag ctt cca att cta gaa       482
Val Tyr Thr Phe Val Gln Lys Met Pro Gly Gln Leu Pro Ile Leu Glu
```

-continued

| | | |
|---|---|---|
| ggg gaa gtt ttt gat tct gtg aag cca gga ctt tct gct ttt gta gat<br>Gly Glu Val Phe Asp Ser Val Lys Pro Gly Leu Ser Ala Phe Val Asp<br>80                          85                      90                   95 | 530 |
| caa cct aag cag ggt gct gag acc gtt caa ggg ctc tta gag gtg gcc<br>Gln Pro Lys Gln Gly Ala Glu Thr Val Gln Gly Leu Leu Glu Val Ala<br>                      100                   105                 110 | 578 |
| aaa gac tca atc ccc cga agt cac tgg aaa aag acc cca gtg gtc cta<br>Lys Asp Ser Ile Pro Arg Ser His Trp Lys Lys Thr Pro Val Val Leu<br>          115                   120                 125 | 626 |
| aag gca aca gca gga cta cgc tta ctg cca gaa cac aaa gcc aag gct<br>Lys Ala Thr Ala Gly Leu Arg Leu Leu Pro Glu His Lys Ala Lys Ala<br>          130                   135                 140 | 674 |
| ctg ctc ttt gag gta aag gag atc ttc agg aag tca cct ttc ctg gta<br>Leu Leu Phe Glu Val Lys Glu Ile Phe Arg Lys Ser Pro Phe Leu Val<br>     145                   150                 155 | 722 |
| cca aag ggc agt gtt agc atc atg gat gga tcc gac gaa ggc ata tta<br>Pro Lys Gly Ser Val Ser Ile Met Asp Gly Ser Asp Glu Gly Ile Leu<br>160                        165                 170               175 | 770 |
| gct tgg gtt act gtg aat ttt ctg aca ggt cag ctg cat ggc cac aga<br>Ala Trp Val Thr Val Asn Phe Leu Thr Gly Gln Leu His Gly His Arg<br>                      180                 185                 190 | 818 |
| cag gag act gtg ggg acc ttg gac cta ggg gga gcc tcc acc caa atc<br>Gln Glu Thr Val Gly Thr Leu Asp Leu Gly Gly Ala Ser Thr Gln Ile<br>                195                 200                 205 | 866 |
| acg ttc ctg ccc cag ttt gag aaa act ctg gaa caa act cct agg ggc<br>Thr Phe Leu Pro Gln Phe Glu Lys Thr Leu Glu Gln Thr Pro Arg Gly<br>          210                   215                 220 | 914 |
| tac ctc act tcc ttt gag atg ttt aac agc act tat aag ctc tat aca<br>Tyr Leu Thr Ser Phe Glu Met Phe Asn Ser Thr Tyr Lys Leu Tyr Thr<br>     225                   230                 235 | 962 |
| cat agt tac ctg gga ttt gga ttg aaa gct gca aga cta gca acc ctg<br>His Ser Tyr Leu Gly Phe Gly Leu Lys Ala Ala Arg Leu Ala Thr Leu<br>240                        245                 250               255 | 1010 |
| gga gcc ctg gag aca gaa ggg act gat ggg cac act ttc cgg agt gcc<br>Gly Ala Leu Glu Thr Glu Gly Thr Asp Gly His Thr Phe Arg Ser Ala<br>                      260                 265                 270 | 1058 |
| tgt tta ccg aga tgg ttg gaa gca gag tgg atc ttt ggg ggt gtg aaa<br>Cys Leu Pro Arg Trp Leu Glu Ala Glu Trp Ile Phe Gly Gly Val Lys<br>          275                   280                 285 | 1106 |
| tac cag tat ggt ggc aac caa gaa ggg gag gtg ggc ttt gag ccc tgc<br>Tyr Gln Tyr Gly Gly Asn Gln Glu Gly Glu Val Gly Phe Glu Pro Cys<br>          290                   295                 300 | 1154 |
| tat gcc gaa gtg ctg agg gtg gta cga gga aaa ctt cac cag cca gag<br>Tyr Ala Glu Val Leu Arg Val Val Arg Gly Lys Leu His Gln Pro Glu<br>     305                   310                 315 | 1202 |
| gag gtc cag aga ggt tcc ttc tat gct ttc tct tac tat tat gac cga<br>Glu Val Gln Arg Gly Ser Phe Tyr Ala Phe Ser Tyr Tyr Tyr Asp Arg<br>320                        325                 330               335 | 1250 |
| gct gtt gac aca gac atg att gat tat gaa aag ggg ggt att tta aaa<br>Ala Val Asp Thr Asp Met Ile Asp Tyr Glu Lys Gly Gly Ile Leu Lys<br>                      340                 345                 350 | 1298 |
| gtt gaa gat ttt gaa aga aaa gcc agg gaa gtg tgt gat aac ttg gaa<br>Val Glu Asp Phe Glu Arg Lys Ala Arg Glu Val Cys Asp Asn Leu Glu<br>          355                   360                 365 | 1346 |
| aac ttc acc tca ggc agt cct ttc ctg tgc atg gat ctc agc tac atc<br>Asn Phe Thr Ser Gly Ser Pro Phe Leu Cys Met Asp Leu Ser Tyr Ile<br>          370                   375                 380 | 1394 |
| aca gcc ctg tta aag gat ggc ttt ggc ttt gca gac agc aca gtc tta | 1442 |

```
              Thr Ala Leu Leu Lys Asp Gly Phe Gly Phe Ala Asp Ser Thr Val Leu
              385                 390                 395 cag ctc aca aag aaa gtg aac aac ata gag acg ggc tgg gcc ttg ggg          1490
Gln Leu Thr Lys Lys Val Asn Asn Ile Glu Thr Gly Trp Ala Leu Gly
400                 405                 410                 415 gcc acc ttt cac ctg ttg cag tct ctg ggc atc tcc cat tgaggccacg          1539
Ala Thr Phe His Leu Leu Gln Ser Leu Gly Ile Ser His
                420                 425 tacttccttg agacctgca tttgccaaca ccttttttaag gggaggagag agcacttagt       1599
ttctgaacta gtctggggac atcctggact tgagcctaga gattwrgtta attaascggc       1659
cgagcttatc cttwatragg taatttactt gcmtggccgc gtttacacgt cgtgatggna       1719
aacctgcgtc ccaactaacg cttgasamat ccccttcgca gctgcgatac caaaagccga      1779
cgacgccttc cacagtgcca                                                    1799

<210> SEQ ID NO 3
<211> LENGTH: 428
<212> TYPE: PRT
<213> ORGANISM: Homo sapiens

<400> SEQUENCE: 3

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
                20                  25                  30

Ile Phe Leu Ser Ser Met Cys Pro Ile Asn Val Ser Ala Ser Thr Leu
            35                  40                  45

Tyr Gly Ile Met Phe Asp Ala Gly Ser Thr Gly Thr Arg Ile His Val
        50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270
```

```
Leu Pro Arg Trp Leu Glu Ala Glu Trp Ile Phe Gly Gly Val Lys Tyr
            275                 280                 285

Gln Tyr Gly Gly Asn Gln Glu Gly Val Gly Phe Glu Pro Cys Tyr
        290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Asp Arg Ala
            325                 330                 335

Val Asp Thr Asp Met Ile Asp Tyr Glu Lys Gly Ile Leu Lys Val
            340                 345                 350

Glu Asp Phe Glu Arg Lys Ala Arg Glu Val Cys Asp Asn Leu Glu Asn
            355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400

Leu Thr Lys Lys Val Asn Asn Ile Glu Thr Gly Trp Ala Leu Gly Ala
            405                 410                 415

Thr Phe His Leu Leu Gln Ser Leu Gly Ile Ser His
            420                 425
```

<210> SEQ ID NO 4
<211> LENGTH: 1287
<212> TYPE: DNA
<213> ORGANISM: Homo sapiens
<220> FEATURE:
<221> NAME/KEY: CDS
<222> LOCATION: (1)..(1284)

<400> SEQUENCE: 4

```
atg gcc act tct tgg ggc aca gtc ttt ttc atg ctg gtg gta tcc tgt      48
Met Ala Thr Ser Trp Gly Thr Val Phe Phe Met Leu Val Val Ser Cys
  1               5                  10                  15 gtt tgc agc gct gtc tcc cac agg aac cag cag act tgg ttt gag ggt      96
Val Cys Ser Ala Val Ser His Arg Asn Gln Gln Thr Trp Phe Glu Gly
             20                  25                  30 atc ttc ctg tct tcc atg tgc ccc atc aat gtc agc gcc agc acc ttg     144
Ile Phe Leu Ser Ser Met Cys Pro Ile Asn Val Ser Ala Ser Thr Leu
         35                  40                  45 tat gga att atg ttt gat gca ggg agc act gga act cga att cat gtt     192
Tyr Gly Ile Met Phe Asp Ala Gly Ser Thr Gly Thr Arg Ile His Val
     50                  55                  60 tac acc ttt gtg cag aaa atg cca gga cag ctt cca att cta gaa ggg     240
Tyr Thr Phe Val Gln Lys Met Pro Gly Gln Leu Pro Ile Leu Glu Gly
 65                  70                  75                  80 gaa gtt ttt gat tct gtg aag cca gga ctt tct gct ttt gta gat caa     288
Glu Val Phe Asp Ser Val Lys Pro Gly Leu Ser Ala Phe Val Asp Gln
                 85                  90                  95 cct aag cag ggt gct gag acc gtt caa ggg ctc tta gag gtg gcc aaa     336
Pro Lys Gln Gly Ala Glu Thr Val Gln Gly Leu Leu Glu Val Ala Lys
            100                 105                 110 gac tca atc ccc cga agt cac tgg aaa aag acc cca gtg gtc cta aag     384
Asp Ser Ile Pro Arg Ser His Trp Lys Lys Thr Pro Val Val Leu Lys
        115                 120                 125 gca aca gca gga cta cgc tta ctg cca gaa cac aaa gcc aag gct ctg     432
Ala Thr Ala Gly Leu Arg Leu Leu Pro Glu His Lys Ala Lys Ala Leu
    130                 135                 140 ctc ttt gag gta aag gag atc ttc agg aag tca cct ttc ctg gta cca     480
```

```
Leu Phe Glu Val Lys Glu Ile Phe Arg Lys Ser Pro Phe Leu Val Pro
145                 150                 155                 160 aag ggc agt gtt agc atc atg gat gga tcc gac gaa ggc ata tta gct        528
Lys Gly Ser Val Ser Ile Met Asp Gly Ser Asp Glu Gly Ile Leu Ala
                165                 170                 175 tgg gtt act gtg aat ttt ctg aca ggt cag ctg cat ggc cac aga cag        576
Trp Val Thr Val Asn Phe Leu Thr Gly Gln Leu His Gly His Arg Gln
            180                 185                 190 gag act gtg ggg acc ttg gac cta ggg gga gcc tcc acc caa atc acg        624
Glu Thr Val Gly Thr Leu Asp Leu Gly Gly Ala Ser Thr Gln Ile Thr
        195                 200                 205 ttc ctg ccc cag ttt gag aaa act ctg gaa caa act cct agg ggc tac        672
Phe Leu Pro Gln Phe Glu Lys Thr Leu Glu Gln Thr Pro Arg Gly Tyr
    210                 215                 220 ctc act tcc ttt gag atg ttt aac agc act tat aag ctc tat aca cat        720
Leu Thr Ser Phe Glu Met Phe Asn Ser Thr Tyr Lys Leu Tyr Thr His
225                 230                 235                 240 agt tac ctg gga ttt gga ttg aaa gct gca aga cta gca acc ctg gga        768
Ser Tyr Leu Gly Phe Gly Leu Lys Ala Ala Arg Leu Ala Thr Leu Gly
                245                 250                 255 gcc ctg gag aca gaa ggg act gat ggg cac act ttc cgg agt gcc tgt        816
Ala Leu Glu Thr Glu Gly Thr Asp Gly His Thr Phe Arg Ser Ala Cys
            260                 265                 270 tta ccg aga tgg ttg gaa gca gag tgg atc ttt ggg ggt gtg aaa tac        864
Leu Pro Arg Trp Leu Glu Ala Glu Trp Ile Phe Gly Gly Val Lys Tyr
        275                 280                 285 cag tat ggt ggc aac caa gaa ggg gag gtg ggc ttt gag ccc tgc tat        912
Gln Tyr Gly Gly Asn Gln Glu Gly Glu Val Gly Phe Glu Pro Cys Tyr
    290                 295                 300 gcc gaa gtg ctg agg gtg gta cga gga aaa ctt cac cag cca gag gag        960
Ala Glu Val Leu Arg Val Val Arg Gly Lys Leu His Gln Pro Glu Glu
305                 310                 315                 320 gtc cag aga ggt tcc ttc tat gct ttc tct tac tat tat gac cga gct       1008
Val Gln Arg Gly Ser Phe Tyr Ala Phe Ser Tyr Tyr Tyr Asp Arg Ala
                325                 330                 335 gtt gac aca gac atg att gat tat gaa aag ggg ggt att tta aaa gtt       1056
Val Asp Thr Asp Met Ile Asp Tyr Glu Lys Gly Gly Ile Leu Lys Val
            340                 345                 350 gaa gat ttt gaa aga aaa gcc agg gaa gtg tgt gat aac ttg gaa aac       1104
Glu Asp Phe Glu Arg Lys Ala Arg Glu Val Cys Asp Asn Leu Glu Asn
        355                 360                 365 ttc acc tca ggc agt cct ttc ctg tgc atg gat ctc agc tac atc aca       1152
Phe Thr Ser Gly Ser Pro Phe Leu Cys Met Asp Leu Ser Tyr Ile Thr
    370                 375                 380 gcc ctg tta aag gat ggc ttt ggc ttt gca gac agc aca gtc tta cag       1200
Ala Leu Leu Lys Asp Gly Phe Gly Phe Ala Asp Ser Thr Val Leu Gln
385                 390                 395                 400 ctc aca aag aaa gtg aac aac ata gag acg ggc tgg gcc ttg ggg gcc       1248
Leu Thr Lys Lys Val Asn Asn Ile Glu Thr Gly Trp Ala Leu Gly Ala
                405                 410                 415 acc ttt cac ctg ttg cag tct ctg ggc atc tcc cat tga                    1287
Thr Phe His Leu Leu Gln Ser Leu Gly Ile Ser His
            420                 425

<210> SEQ ID NO 5
<211> LENGTH: 428
<212> TYPE: PRT
<213> ORGANISM: Homo sapiens

<400> SEQUENCE: 5
```

-continued

```
Met Ala Thr Ser Trp Gly Thr Val Phe Phe Met Leu Val Val Ser Cys
 1               5                  10                 15

Val Cys Ser Ala Val Ser His Arg Asn Gln Gln Thr Trp Phe Glu Gly
             20                  25                  30

Ile Phe Leu Ser Ser Met Cys Pro Ile Asn Val Ser Ala Ser Thr Leu
             35                  40                  45

Tyr Gly Ile Met Phe Asp Ala Gly Ser Thr Gly Thr Arg Ile His Val
     50                  55                  60

Tyr Thr Phe Val Gln Lys Met Pro Gly Gln Leu Pro Ile Leu Glu Gly
 65                  70                  75                  80

Glu Val Phe Asp Ser Val Lys Pro Gly Leu Ser Ala Phe Val Asp Gln
                 85                  90                  95

Pro Lys Gln Gly Ala Glu Thr Val Gln Gly Leu Leu Glu Val Ala Lys
                100                 105                 110

Asp Ser Ile Pro Arg Ser His Trp Lys Lys Thr Pro Val Val Leu Lys
            115                 120                 125

Ala Thr Ala Gly Leu Arg Leu Leu Pro Glu His Lys Ala Lys Ala Leu
        130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400

Leu Thr Lys Lys Val Asn Asn Ile Glu Thr Gly Trp Ala Leu Gly Ala
                405                 410                 415

Thr Phe His Leu Leu Gln Ser Leu Gly Ile Ser His
```

-continued

```
                    420             425

<210> SEQ ID NO 6
<211> LENGTH: 1287
<212> TYPE: DNA
<213> ORGANISM: Homo sapiens
<220> FEATURE:
<221> NAME/KEY: CDS
<222> LOCATION: (1)..(1284)

<400> SEQUENCE: 6 atg gcc act tct tgg ggc aca gtc ttt ttc atg ctg gtg gta tcc tgt      48
Met Ala Thr Ser Trp Gly Thr Val Phe Phe Met Leu Val Val Ser Cys
 1               5                  10                  15 gtt tgc agc gct gtc tcc cac agg aac cag cag act tgg ttt gag ggt      96
Val Cys Ser Ala Val Ser His Arg Asn Gln Gln Thr Trp Phe Glu Gly
             20                  25                  30 atc ttc ctg tct tcc atg tgc ccc atc aat gtc agc gcc agc acc ttg     144
Ile Phe Leu Ser Ser Met Cys Pro Ile Asn Val Ser Ala Ser Thr Leu
         35                  40                  45 tat gga att atg ttt gat gca ggg agc act gga act cga att cat gtt     192
Tyr Gly Ile Met Phe Asp Ala Gly Ser Thr Gly Thr Arg Ile His Val
     50                  55                  60 tac acc ttt gtg cag aaa atg cca gga cag ctt cca att cta gaa ggg     240
Tyr Thr Phe Val Gln Lys Met Pro Gly Gln Leu Pro Ile Leu Glu Gly
 65                  70                  75                  80 gaa gtt ttt gat tct gtg aag cca gga ctt tct gct ttt gta gat caa     288
Glu Val Phe Asp Ser Val Lys Pro Gly Leu Ser Ala Phe Val Asp Gln
                 85                  90                  95 cct aag cag ggt gct gag acc gtt caa ggg ctc tta gag gtg gcc aaa     336
Pro Lys Gln Gly Ala Glu Thr Val Gln Gly Leu Leu Glu Val Ala Lys
            100                 105                 110 gac tca atc ccc cga agt cac tgg aaa aag acc cca gtg gtc cta aag     384
Asp Ser Ile Pro Arg Ser His Trp Lys Lys Thr Pro Val Val Leu Lys
        115                 120                 125 gca aca gca gga cta cgc tta ctg cca gaa cac aaa gcc aag gct ctg     432
Ala Thr Ala Gly Leu Arg Leu Leu Pro Glu His Lys Ala Lys Ala Leu
    130                 135                 140 ctc ttt gag gta aag gag atc ttc agg aag tca cct ttc ctg gta cca     480
Leu Phe Glu Val Lys Glu Ile Phe Arg Lys Ser Pro Phe Leu Val Pro
145                 150                 155                 160 aag ggc agt gtt agc atc atg act gga caa gac gaa ggc ata ttc gct     528
Lys Gly Ser Val Ser Ile Met Thr Gly Gln Asp Glu Gly Ile Phe Ala
                165                 170                 175 tgg gtt act gtg aat ttt ctg aca ggt cag ctg cat ggc cac aga cag     576
Trp Val Thr Val Asn Phe Leu Thr Gly Gln Leu His Gly His Arg Gln
            180                 185                 190 gag act gtg ggg acc ttg gac cta ggg gga gcc tcc acc caa atc acg     624
Glu Thr Val Gly Thr Leu Asp Leu Gly Gly Ala Ser Thr Gln Ile Thr
        195                 200                 205 ttc ctg ccc cag ttt gag aaa act ctg gaa caa act cct agg ggc tac     672
Phe Leu Pro Gln Phe Glu Lys Thr Leu Glu Gln Thr Pro Arg Gly Tyr
    210                 215                 220 ctc act tcc ttt gag atg ttt aac agc act tat aag ctc tat aca cat     720
Leu Thr Ser Phe Glu Met Phe Asn Ser Thr Tyr Lys Leu Tyr Thr His
225                 230                 235                 240 agt tac ctg gga ttt gga ttg aaa gct gca aga cta gca acc ctg gga     768
Ser Tyr Leu Gly Phe Gly Leu Lys Ala Ala Arg Leu Ala Thr Leu Gly
                245                 250                 255 gcc ctg gag aca gaa ggg act gat ggg cac act ttc cgg agt gcc tgt     816
Ala Leu Glu Thr Glu Gly Thr Asp Gly His Thr Phe Arg Ser Ala Cys
```

```
                260                   265                   270
tta ccg aga tgg ttg gaa gca gag tgg atc ttt ggg ggt gtg aaa tac        864
Leu Pro Arg Trp Leu Glu Ala Glu Trp Ile Phe Gly Gly Val Lys Tyr
        275                   280                   285 cag tat ggt ggc aac caa gaa ggg gag gtg ggc ttt gag ccc tgc tat        912
Gln Tyr Gly Gly Asn Gln Glu Gly Glu Val Gly Phe Glu Pro Cys Tyr
        290                   295                   300 gcc gaa gtg ctg agg gtg gta cga gga aaa ctt cac cag cca gag gag        960
Ala Glu Val Leu Arg Val Val Arg Gly Lys Leu His Gln Pro Glu Glu
305                   310                   315                   320 gtc cag aga ggt tcc ttc tat gct ttc tct tac tat tat gac cga gct       1008
Val Gln Arg Gly Ser Phe Tyr Ala Phe Ser Tyr Tyr Tyr Asp Arg Ala
                325                   330                   335 gtt gac aca gac atg att gat tat gaa aag ggg ggt att tta aaa gtt       1056
Val Asp Thr Asp Met Ile Asp Tyr Glu Lys Gly Gly Ile Leu Lys Val
                340                   345                   350 gaa gat ttt gaa aga aaa gcc agg gaa gtg tgt gat aac ttg gaa aac       1104
Glu Asp Phe Glu Arg Lys Ala Arg Glu Val Cys Asp Asn Leu Glu Asn
                355                   360                   365 ttc acc tca ggc agt cct ttc ctg tgc atg gat ctc agc tac atc aca       1152
Phe Thr Ser Gly Ser Pro Phe Leu Cys Met Asp Leu Ser Tyr Ile Thr
        370                   375                   380 gcc ctg tta aag gat ggc ttt ggc ttt gca gac agc aca gtc tta cag       1200
Ala Leu Leu Lys Asp Gly Phe Gly Phe Ala Asp Ser Thr Val Leu Gln
385                   390                   395                   400 ctc aca aag aaa gtg aac aac ata gag acg ggc tgg gcc ttg ggg gcc       1248
Leu Thr Lys Lys Val Asn Asn Ile Glu Thr Gly Trp Ala Leu Gly Ala
                405                   410                   415 acc ttt cac ctg ttg cag tct ctg ggc atc tcc cat tga                   1287
Thr Phe His Leu Leu Gln Ser Leu Gly Ile Ser His
        420                   425

<210> SEQ ID NO 7
<211> LENGTH: 428
<212> TYPE: PRT
<213> ORGANISM: Homo sapiens

<400> SEQUENCE: 7

Met Ala Thr Ser Trp Gly Thr Val Phe Phe Met Leu Val Val Ser Cys
 1               5                  10                  15

Val Cys Ser Ala Val Ser His Arg Asn Gln Gln Thr Trp Phe Glu Gly
                20                  25                  30

Ile Phe Leu Ser Ser Met Cys Pro Ile Asn Val Ser Ala Ser Thr Leu
            35                  40                  45

Tyr Gly Ile Met Phe Asp Ala Gly Ser Thr Gly Thr Arg Ile His Val
        50                  55                  60

Tyr Thr Phe Val Gln Lys Met Pro Gly Gln Leu Pro Ile Leu Glu Gly
 65                 70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160
```

```
Lys Gly Ser Val Ser Ile Met Thr Gly Gln Asp Glu Gly Ile Phe Ala
                165                 170                 175
Trp Val Thr Val Asn Phe Leu Thr Gly Gln Leu His Gly His Arg Gln
            180                 185                 190
Glu Thr Val Gly Thr Leu Asp Leu Gly Gly Ala Ser Thr Gln Ile Thr
        195                 200                 205
Phe Leu Pro Gln Phe Glu Lys Thr Leu Glu Gln Thr Pro Arg Gly Tyr
    210                 215                 220
Leu Thr Ser Phe Glu Met Phe Asn Ser Thr Tyr Lys Leu Tyr Thr His
225                 230                 235                 240
Ser Tyr Leu Gly Phe Gly Leu Lys Ala Ala Arg Leu Ala Thr Leu Gly
                245                 250                 255
Ala Leu Glu Thr Glu Gly Thr Asp Gly His Thr Phe Arg Ser Ala Cys
            260                 265                 270
Leu Pro Arg Trp Leu Glu Ala Glu Trp Ile Phe Gly Gly Val Lys Tyr
        275                 280                 285
Gln Tyr Gly Gly Asn Gln Glu Gly Glu Val Gly Phe Glu Pro Cys Tyr
    290                 295                 300
Ala Glu Val Leu Arg Val Val Arg Gly Lys Leu His Gln Pro Glu Glu
305                 310                 315                 320
Val Gln Arg Gly Ser Phe Tyr Ala Phe Ser Tyr Tyr Asp Arg Ala
                325                 330                 335
Val Asp Thr Asp Met Ile Asp Tyr Glu Lys Gly Gly Ile Leu Lys Val
            340                 345                 350
Glu Asp Phe Glu Arg Lys Ala Arg Glu Val Cys Asp Asn Leu Glu Asn
        355                 360                 365
Phe Thr Ser Gly Ser Pro Phe Leu Cys Met Asp Leu Ser Tyr Ile Thr
    370                 375                 380
Ala Leu Leu Lys Asp Gly Phe Gly Phe Ala Asp Ser Thr Val Leu Gln
385                 390                 395                 400
Leu Thr Lys Lys Val Asn Asn Ile Glu Thr Gly Trp Ala Leu Gly Ala
                405                 410                 415
Thr Phe His Leu Leu Gln Ser Leu Gly Ile Ser His
            420                 425

<210> SEQ ID NO 8
<211> LENGTH: 9365
<212> TYPE: DNA
<213> ORGANISM: Homo sapiens
<220> FEATURE:
<221> NAME/KEY: misc_feature
<222> LOCATION: (3409)
<223> OTHER INFORMATION: n = adenine or guanine or cytosine or thymidine
<221> NAME/KEY: misc_feature
<222> LOCATION: (9214)
<223> OTHER INFORMATION: n = adenine or guanine or cytosine or thymidine
<221> NAME/KEY: misc_feature
<222> LOCATION: (9303)
<223> OTHER INFORMATION: n = adenine or guanine or cytosine or thymidine
<221> NAME/KEY: misc_feature
<222> LOCATION: (9311)
<223> OTHER INFORMATION: n = adenine or guanine or cytosine or thymidine

<400> SEQUENCE: 8
gcctctgcag gtgtgcgagc aggattgctt ctgcaacaaa agcctccacc cagccacatc     60
ttgggaaaag aatggccact tcttggggca cagtcttttt catgctggtg gtatcctgtg    120
tttgcagcgc tgtctcccac aggaaccagc agacttggtt tgagggtatc ttcctgtctt    180
```

-continued

```
ccatgtgccc catcaatgtc agcgccagca ccttgtatgg aattatgttt gatgcaggga    240
gcactggaac tcgaattcat gtttacacct ttgtgcagaa aatgccaggt aagtgcaact    300
gggrcccttr gtagagtctg taaatccaca ctttagcatc tcctcccaga aacaaatatg    360
ctgagagttt attatgtgaa ttacagaatc tcacacctag tggatgtctt tcttcagaga    420
actttggact acaattgaac atgtgggtta tttatttatt tttatttatt tgttttgttt    480
ttatttttta actttttttt tgagacaagg tcttgctttg ttgcccggtc tgtagtgcag    540
tggcatgatg acacatcact gcaaccttga cctcctgggc tcaagcagtc cttccacctc    600
agccccctga gttgttgaga ctacaggctt gtgccaccat gcccagctca ttttttaaatt    660 tttttataga gacctgctca gactggcctc aaactcctag gctcaattga tcctcccacc    720
tcagcctccc aaagtactgg gattataggt gtaagtcacc atgcttggcc agaacacatg    780
gcttaattca atgtgaaatt agaagagagc tgggctgtct gtagtctgaa acccatgtgt    840
tcaaaaagaa tagttataat ttgttcttcc tctttaaaca tgggatactc cagggatcca    900
taatattcag aatatgggga gtggttttgg gagaaggatc acatgagaat ttcactgcca    960
tccttggaca tgaggctagg aatccctgaa gattaacttt ttctgaattt gtcagtgttt   1020
tttcctcagg tcacttatgg agcctgggga aggtggagg agttaggtgt ccaccagaga   1080
aatggtagca gaaatggacc ctcagaggtt gctctagtcc ttctttccag tactcctgca   1140
agacattcct cacaactagg atcattgggg taacttcagg gaagtcatag gaaaacttac   1200
agagacagag cccagcatct gaagcagcct aacttttggt aaccagctct ctcttctgtt   1260
ttgttccatg racaaaatag gacagcttcc aattctagaa ggggaagttt ttgattctgt   1320
gaagccagga ctttctgctt ttgtagatca acctaagcag ggtgctgaga ccgttcaagg   1380
gctcttagag gtggccaaag actcaatccc ccgaagtcac tggaaaaaga ccccagtggt   1440
cctaaaggca acagcaggac tacgcttact gccagaacaa aaagccaagg ctctgctctt   1500
tgaggtaaag gagatcttca ggaagtcacc tttcctggta ccaaagggca gtgttagcat   1560
catggatgga tccgacgaag gtgggagagg tgttgatatg cgttccaggg ggagaggggc   1620
aggatcagtg aaagatctaa ctaaaggaac tggggccagg aataaacaga aggaatgaga   1680
tagcaggaaa tagaagacag ggagaaggga acatgtgctc tagacatgga atttagagag   1740
gaaaaaaaaa aaacaaggtt ggggccagga aagagaaaaa atgctctggg atctaatcct   1800
tgtctttctt tcttttttagg catattagct tgggttactg tgaattttct gacaggtaat   1860
acatcctcaa gtttatcttt agagcttaac tagcttttac atgcatagtc agaggagtaa   1920
aagcctcttc tttcattctg tattgtttct tcttctttaa aaaaggaaaa gaggctgggt   1980
gtggcagttc atgcctgtta attccagcgc tttgggaggc tgagttgggc agatcacttg   2040
aggccaggag ttcaagacca gcctggccaa catggcgaaa ctccgtctct accaaaaata   2100
caaaaatagc tgggcatggt ggtgtgtacc tgtagtccca gctactcagg aggctggaga   2160
atcacttgaa cccaggaggc agaggttgca gtgagctgag agccgagatt gcgccactgc   2220
actccaggct ggatgataga gcaagactct gtctccaaaa aggccttcca aaaaaaaaaa   2280
aaacacctgc cttgaaggcc tctgctgcaa caagagtcct tccgagttga cattcacctg   2340
cagccttggg gctggggagc agtggagtat atatggaata ccttcagtgt atgataagag   2400
caagagagac aagtgttggg ctgcccagga tgtcgaggct attagagct ggctctcatt   2460 tgacaggtca gctgcatggc cacagacagg agactgtggg gaccttggac ctaggggag   2520 cctccaccca aatcacgttc ctgccccagt ttgaggtgag tcatttaatg aagatctggt   2580
```

```
tagaagtgca cttggcaggc gtatcatggt gccaagaaag aggcgcccca ttttcagcca    2640
gcagctctac cacgcttagg cagagtcaag tcaattaata actaggtgaa tgttcccttg    2700
ccatctcact gttcagaatc ccttcgtttc ctcaagccta gtgagattag ccccttaatc    2760
tgtcttcatc tctgattttt tgctgggagg acgggtggt ggtgtgaaca tcttcaggta     2820
attacagatc ctgaatagct ttttgctttt tctgatttgc agaaaactct ggaacaaamt    2880
cyatrgggct acctcacttc ctttgagatg tttaacagca cttataagct ctatacacat    2940
aggtgaggac ggggacaggg aagaagaata tttmwtkttg tatgatksty ytamctktss    3000
maagcwtkct caaatctstk aytkyatctg attmgcaaaa acaaagdctg tgccaattcc    3060
ctaaggccta tcaactgaaa cccggwccac ttacaaagcc ggaggagcct aagaggcttc    3120
tccattcttg gcctcaaaag cattaatata tgacttaaga gtcaaaagtt ttggstgggg    3180
cagtggcttc atgcctgtaa tccctgcact ttgggaggcc gaggtgggtg ggtcacctga    3240
ggtcaggcgt ttragaccag cctggcaaac atggtgaaac cccgtctyta ctaaaataca    3300
aaaattagct ggatatgaca gcgcacacct gtaatcctag ctattcagga ggctgaggca    3360
ggagaatcat ttgaaccctg gaggcggaga ttgcagtgag ccgagatcnc accmctgcac    3420
ttcagccgga gcgacagagc aagactcagt ctcaaaaaaa aaaaaaaaa gaatcaaaag     3480 ctttctgtag ggagaggaca cttcaagaag gctcaggcaa agctccttgc cagctccttt    3540
gagctggcct tcagaggttc agaatccagc ctggaatgtg atcccagttg gggctaggag    3600
ctaagctaaa gagagctttt ctgggaatgg ttcctagwgt gggaccctag gaattgtcac    3660
tgtctctggc ctttgaatga taactgtggg gaattcttac tgcatagcct tgatccaaac    3720
tgtgcagaaa ttaccccttg ttgaccacag gagatgaata tgtcacagac agaacaaggt    3780
tttcatcttt ccagagggac acaggaacaa tgttactttt gaaagaggta gctttaggct    3840
agagaacttc aggaccagca tgaaattagt caatcctgta ttttacagtt acctgggatt    3900
tggattgaaa gctgcaagac tagcaaccct gggagccctg gagacagaag gtttgtctgg    3960
gtacctgtgc tgggggggga tggtgagggt gacacagata ctccgcttgc ttcttccctt    4020
ccttgatagc cattctatgg aggaaaagat tatgttgaat tgggaggcaa atgttgtata    4080
atggacctaa taatggcaaa ctccttttct agtttataag ttcagaagtt ttgatgtata    4140
ttattagcca ttttttagaat gaggtctact tgttcagggg taacagccta tgtctaggca    4200
gctgaagtgt ctgcagaaat cccaggcttt acgaatacat tcagcaggag cttgctcaag    4260
ccctgagctt tacattggag gcacaggaag cagagtctgt tctacatgca ggtgaacaa    4320 cagagtaact ccattgatct cttcacaggt caggcagaac tgggttcagt cccagtgttg    4380
tgatatgagg cragtaacct atctgtgccc ctttcctcac attaaatgag aatttgcatt    4440
taaggcactt tgtacagtaa tctgttattg ggatgacatc tattttgcat ttcagagtat    4500
acaaaacatc ttcaagtata tttaattgaa gcctctcagc aaccagtgag gaaggtagca    4560
tagcatttct ttcctgtttt tataaagggg aaagttgctg takgaaggtt ykrgatctct    4620
twragatgtg atraaagcca tggaccctc tgacaaaagc acatatgcat gaaaatttgc     4680
ttctggtttc aggggttca ccaaccccac aaagcctatc tttgaaccct gagttaagga     4740
ttcctgtcac aggatgttgt catggaatta atttcatagg attttaaggc ccagccccca    4800
tggtgaytct tttccacctc actggcttct tgcttgcctt cctccctctc tctcacttac    4860
ttacctctta ccttgtgccc tggattcttt cagggactga tgggcacact ttccggagtg    4920
```

```
cctgtttacc gagatggttg gaagcagagt ggatctttgg gggtgtgaaa taccagtatg  4980
gtggcaacca agaaggcaag tgatgttttt tcactggtta aagttacgtt tacaatggaa  5040
gctctggaaa agtcccatgg gaacttttt ccagaactca agagaagctt atcttgttgc  5100
agggasttat tccaaagatc ttggcatgcc tccaaggact aatgtgaagt gacagtgaac  5160
aaagcagctg tcattctgca tcagccaagt gtcatggacc cattagatac ctgcccttag  5220
ccaagtgctg tggtgcacat ctattgtcct agctactcca aaggttgagg caagaggatc  5280
acttgagccc atgagttcaa ggctatagtg cgcaatgcca ctgcactcca gcctgggcaa  5340
cagggagacc ctacctctta caaattaatt aagaagcata ttctaagcct aggtctaatg  5400
cagcagtgtg aaagcctgtt tagttaatgg ttagctattt aaattatagt aaaacttaaa  5460
accaagacaa gaatgattca tcttcttata aaaggtatat acctgaatat caaggaatga  5520
acctgaattc ccagtgaagg aagcaggcga gcccctttagc tacttgctta caaatgctat  5580
ggaatgtaat gctaggcagc agcacaaggt tggccatgat ctggtgaata cagattaggc  5640
aggagagcgg ccatggagaa acagactggt gaggctgcag acgtttgctc atctttgttt  5700
tgacgcctct tgtcccaagc ctcagccttc tcctgctttc ttgaccttcc tgctgttccc  5760
tcattgtctc cagcagcctg cctcagagag tgtccccttc cccagcgtc gttctcacct  5820
taccctgtg caccttgcc tggcagggga ggtgggcttt gagccctgct atgccgaagt  5880
gctgagggtg gtacgaggaa aacttcacca gccagaggag gtccagagag gttccttcta  5940
tgctttctct tactattatg accgagctgt tgacacagac atgattggtg agttcacccc  6000
aggtgtcagt ccagagagga aggtggatag ggctgtggtg gggaaggtca aggagaaaga  6060
gcacttgagg tgctttgtcg gggtgattac ccacctcttt tctagtcact cgaacaaaag  6120
ggtggaaatg acttagagtc ttttggaggt gagagatgac caaaacaact atatgaggtc  6180
tttttttttt taacatgttt attgaggtat aattggcata caataagtgc acatttaaa  6240
gtatacaatt taagttttgt catgtataca cccatgaatc catccagcac attgaagata  6300
ataaacatat ttcaccacaa aaagtttcct cctgtctctt tataacttt cttcttatca  6360
caaaagcagt gttttttgcct aactgtgaaa gtatatgtac ctgatctgtc atggcctgag  6420
agagatgaat taatttccta ttattgtggg ggttttgttg ttgttgttgt tttggttttt  6480
tgtttgtttg tttgtttttt gagacagagt ctcactctgt tacccaggct ggagtgcaat  6540
ggcatgatct aggctcactg caacctctgc ctccgggtt caaccgattc tcctgcccca  6600
gtctcctgag tagctgggat tacaggtgcc tgccaccaca cccggctaat ttttttttta  6660
atagagacga ggtttcacca tgttggtcag gctggtcttg aactcctgac ctcgttatct  6720
gccttcctcg gcctcccaaa gtgctgggat tacaggcatg agccaccaca cccggcctat  6780
tgtgttttat gggtctgttt tttccattgt ggttaaatat acataacatg gaatagattg  6840
taaataagta aattaggttg catagattac attatgtaca tgtgtatata atgaatgaat  6900
gaatgaattt cctatgctt ccttgaaggc gttttgatat cagataatct tctgtttttat  6960
ttcagattat gaaaagggg gtattttaaa agttgaagat tttgaaagaa aagccaggga  7020
agtgtgtgat aacttggaaa acttcacctc aggcagtcct ttcctgtgca tggatctcag  7080
ctacatcaca gccctgttaa aggatggctt tggctttgca gacagcacag tcttacaggt  7140
aagagacagg acaccagagt ctcataacag ccctcttttg tggggttga gaaggagtaa  7200
gagcttgttc agtaatcaga gtagctagaa gtgaaattat gaggtatttt tgtttgggct  7260
atggacaagg tactgtgctg ggcaccatga atgtgggaaa ttatctcaat gcaatggtag  7320
```

-continued

```
cctccgagtg tattaccagg caagctatcg cacaggtcac agaacagaaa gactagcagc    7380
ccaaattaag atgccaagtc acatggttta tttatttatt tatttattta ttattatttt    7440
tttgagacgg agtctygctc ttgttkccyr ggctggagtg cartggcryg atcwcrgctc    7500
actgcarcct ycrcctcctg ggttcaagcg attctyctgc ctcagcctcc cragtagctg    7560
ggattacagg crygcgccac cacgccyggc taatttttt gtatttttag tagagacggg    7620
gtttcaccat gttggccagg ctrktctyra actyctgayc tcaggtgatc cacccrcctc    7680
rgcctcccaa agtgctrgra ttayaggyrt gagccaccac kccyrgcctt ttttgktcgk    7740
ttctttttt tchtttttt tttttttt gagacagggt cttgctctgt cacccatgct        7800
ggagtgcagt ggcatgatct cagttcactg caacctctgc ctcccgggtt caagtgaccc    7860
tcccacctca gccctctgag tagctgggat tacaggtgtg tgccaccact cttgtctaat    7920
ttttttgtag acgggtt ttgccatgtt gcccaggctg tcttgaact cctggcctca        7980
agcaatccac ctgccttggc ctcccaaagt gccaggagta caggcatgag ccactgcgcc    8040
tggccccatg tttggttatt attagtgctt aggaagaggc acttgcttac atagtaggag    8100
ttgagaagct tggtttgttc tttcctaccc ctagatctat tctcacctcc tgaccatgct    8160
cttttctgcca catctattat cattacaagt tgccttatct gaaattagtg aatcagaaaa    8220
taaagcaggg gatactttgt gtagtttcaa cgttagggaa agttcagaat actgtctgtc    8280
taaactatct ctctagaagg cctgatgggc acaacctgg gccagaagca ttcagttcag    8340
atatgagaat ggtgggtgta ggggcaatgg ccaatgggcc atgccggaa ggaaattgtt     8400
acagagtagt gggaagcctg caaagactgg cttctgtccg ttttgccttg gtttgcccat    8460
gtggatattc tttgccaata ttttctgccc aagagctgtg cttgctagag ttggaaactg    8520
gatgaaaagg tgaagacttt ttttcttctc aacagctcac aaagaaagtg aacaacatag    8580
agacgggctg ggccttgggg gccacctttc acctgttgca gtctctgggc atctcccatt    8640
gaggccacgt acttccttgg agacctgcat ttgccaacac cttttttaagg ggaggagaga    8700
gcacttagtt tctgaactag tctggggaca tcctggactt gagcctagag atttaggttt    8760
aattaattt acacatctaa tagtgaactg ctgcctaacc actcaagagt acacagctgg    8820
caccagagca tcacagagag ccctgtgagc caaaagtat agttttggaa cttaaccttg    8880
gagtgagagc ccaggacag gtccctggaa accaaagaaa aatcgcattt caacccttttg    8940
agtgcctcat tccactgaat atttaaattt tcctcttaaa tgggaaactg acttattgca    9000
atcccaagac ccatcaatat cagtattttt ttcctcccta tacagggccc tgcccaccct    9060
tatctgcacc cacctcccct gaaaagaga gaaaaaaaa aamccbggtt ttgctttccw    9120
tgtwtaatyc amcgacmcaa aakgggacca tgtcaaaatc tgtwtgatcc tattytgggt    9180
tascyccaat cagccagctg aragccttcc taanttttaw taggatgara gagtaccycc    9240
taactgtgca taaattcagc cttaaaaaaa aaggcacccg ggctttgggg acatgtttgg    9300
ganggggggg ntgcctcata tacccacctt tggttttaata acattttatc agcactttgg    9360
gataa                                                                 9365
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

```
<400> SEQUENCE: 9
gctacctcac ttcctttgag                                            20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
ctggctggtg aagttttcct c                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
gcaggtctcc aaggaagtac g                                          21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 12
gtgagtgctc cctgcatcta acataattcc                                 30

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 13
gatgcaggga gcactcacac tagtattcat gtttacacct ttgtg                45

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 14
gcgtagtcct gctgttgccc ctaggtacac tggggtcttt ttcc                 44

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
gcaacagcag gactacgctt actgccagaa c                               31

<210> SEQ ID NO 16
<211> LENGTH: 48
```

```
<212> TYPE: DNA
<213> ORGANISM: Artificial Sequence
<220> FEATURE:
<223> OTHER INFORMATION: Description of Artificial Sequence: primer

<400> SEQUENCE: 16
cccaagcgaa tatgccttcg tcttgtccag tcatgatgct aacactgc            48

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 17
cgaaggcata ttcgcttggg ttactgtg                                  28

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 18
cttccttcac tgggaattca gg                                        22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 19
ctgtttaccg agatggttgg aagc                                      24

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 20
ttaaagcttg ggaaaagaat ggccacttc                                 29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 21
agactcgagg tggctcaatg ggagatgcc                                 29

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 22
```

-continued

```
gcgctgtctc ccacagagga tcgcatcacc atcaccatca caaccagcag acttggtt        58
```

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 23

```
aaccaagtct gctggttgtg atggtgatgg tgatgcgatc ctctgtggga gacagcgc        58
```

<210> SEQ ID NO 24
<211> LENGTH: 1601
<212> TYPE: DNA
<213> ORGANISM: Homo sapiens

<400> SEQUENCE: 24

```
gcgggctgcc gcgcaagggt ggcgcgcgcg cgttttcctt gttcctggtc aacaaagaaa        60
tgtggagtgt cttggctgaa tcctcataca gacaagatca ttatggtgct gttaggttga       120
aaaagtgata taataaagga accaaggaga aaattcagaa ggaaagaaaa aattgcctct       180
gcaggtgtgc gagcaggatt gcttctgcaa caaaagcctc cacccagcca catcttggga       240
aaagaatggc cacttcttgg ggcacagtct ttttcatgct ggtggtatcc tgtgtttgca       300
gcgctgtctc ccacaggaac cagcagactt ggtttgaggg tatcttcctg tcttccatgt       360
gccccatcaa tgtcagcgcc agcaccttgt atggaattat gtttgatgca gggagcactg       420
gaactcgaat tcatgtttac acctttgtgc agaaaatgcc aggacagctt ccaattctag       480
aaggggaagt ttttgattct gtgaagccag gactttctgc ttttgtagat caacctaagc       540
agggtgctga daccgttcaa gggctcttag aggtggccaa agactcaatc ccccgaagtc       600
actgaaaaa gaccccagtg gtcctaaagg caacagcagg actacgctta ctgccagaac       660
acaaagccaa ggctctgctc tttgaggtaa aggagatctt caggaagtca cctttcctgg       720
taccaaaggg cagtgttagc atcatggatg gatccgacga aggcatatta gcttgggtta       780
ctgtgaattt tctgacaggt cagctgcatg ccacagaca ggagactgtg gggaccttgg       840
acctaggggg agcctccacc caaatcacgt tcctgcccca gtttgagaaa actctggaac       900
aaactcctag gggctaccto acttcctttg agatgtttaa cagcacttat aagctctata       960
cacatagtta cctgggattt ggattgaaag ctgcaagact agcaaccctg ggagccctgg      1020
agacagaagg gactgatggg cacactttcc ggagtgcctg tttaccgaga tggttggaag      1080
cagagtggat ctttgggggt gtgaaatacc agtatggtgg caaccaagaa ggggaggtgg      1140
gctttgagcc ctgctatgcc gaagtgctga gggtggtacg aggaaaactt caccagccag      1200
aggaggtcca gagaggttcc ttctatgctt tctcttacta ttatgaccga gctgttgaca      1260
cagacatgat tgattatgaa aagggggta ttttaaaagt tgaagatttt gaaagaaaag      1320
ccagggaagt gtgtgataac ttggaaaact tcacctcagg cagtcctttc ctgtgcatgg      1380
atctcagcta catcacagcc ctgttaaagg atggctttgg ctttgcagac agcacagtct      1440
tacaggctgc cgtactgagg tgatgggcca agctggagat atccccaaag cccatgttga      1500
caccctgtcc tgcaagcgga tggactctgt gggctgcatc cctaagaata aagcagagtt      1560
caggtgtgac ctctggcagc aaaaaaaaaa aaaaaaaaa a                          1601
```

<210> SEQ ID NO 25
<211> LENGTH: 405

-continued

```
<212> TYPE: PRT
<213> ORGANISM: Homo sapiens

<400> SEQUENCE: 25

Met Ala Thr Ser Trp Gly Thr Val Phe Phe Met Leu Val Val Ser Cys
 1               5                  10                  15

Val Cys Ser Ala Val Ser His Arg Asn Gln Gln Thr Trp Phe Glu Gly
                20                  25                  30

Ile Phe Leu Ser Ser Met Cys Pro Ile Asn Val Ser Ala Ser Thr Leu
             35                  40                  45

Tyr Gly Ile Met Phe Asp Ala Gly Ser Thr Gly Thr Arg Ile His Val
         50                  55                  60

Tyr Thr Phe Val Gln Lys Met Pro Gly Gln Leu Pro Ile Leu Glu Gly
 65                  70                  75                  80

Glu Val Phe Asp Ser Val Lys Pro Gly Leu Ser Ala Phe Val Asp Gln
                 85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400
```

-continued

```
Ala Ala Val Leu Arg
            405

<210> SEQ ID NO 26
<211> LENGTH: 2762
<212> TYPE: DNA
<213> ORGANISM: Homo sapiens
<220> FEATURE:
<221> NAME/KEY: CDS
<222> LOCATION: (148)..(1599)

<400> SEQUENCE: 26
gtggggtcgt atcccgcggg tggaggccgg ggtggcgccg gccggggcgg gggagcccaa      60
aagaccggct gccgcctgct ccccggaaaa gggcactcgt ctccgtgggt gtggcggagc     120
gcgcggtgca tggaatgggc tatgtga atg aaa aaa ggt atc cgt tat gaa act    174
                        Met Lys Lys Gly Ile Arg Tyr Glu Thr
                          1               5 tcc aga aaa acg agc tac att ttt cag cag ccg cag cac ggt cct tgg     222
Ser Arg Lys Thr Ser Tyr Ile Phe Gln Gln Pro Gln His Gly Pro Trp
 10              15                  20                  25 caa aca agg atg aga aaa ata tcc aac cac ggg agc ctg cgg gtg gcg     270
Gln Thr Arg Met Arg Lys Ile Ser Asn His Gly Ser Leu Arg Val Ala
             30                  35                  40 aag gtg gca tac ccc ctg ggg ctg tgt gtg ggc gtg ttc atc tat gtt     318
Lys Val Ala Tyr Pro Leu Gly Leu Cys Val Gly Val Phe Ile Tyr Val
         45                  50                  55 gcc tac atc aag tgg cac cgg gcc acc gcc acc cag gcc ttc ttc agc     366
Ala Tyr Ile Lys Trp His Arg Ala Thr Ala Thr Gln Ala Phe Phe Ser
     60                  65                  70 atc acc agg gca gcc ccg ggg gcc cgg tgg ggt cag cag gcc cac agc     414
Ile Thr Arg Ala Ala Pro Gly Ala Arg Trp Gly Gln Gln Ala His Ser
 75                  80                  85 ccc ctg ggg aca gct gca gac ggg cac gag gtc ttc tac ggg atc atg     462
Pro Leu Gly Thr Ala Ala Asp Gly His Glu Val Phe Tyr Gly Ile Met
 90                  95                 100                 105 ttt gat gca gga agc act ggc acc cga gta cac gtc ttc cag ttc acc     510
Phe Asp Ala Gly Ser Thr Gly Thr Arg Val His Val Phe Gln Phe Thr
             110                 115                 120 cgg ccc ccc aga gaa act ccc acg tta acc cac gaa acc ttc aaa gca     558
Arg Pro Pro Arg Glu Thr Pro Thr Leu Thr His Glu Thr Phe Lys Ala
         125                 130                 135 gtg aag cca ggt ctt tct gcc tat gct gat gat gtt gaa aag agc gct     606
Val Lys Pro Gly Leu Ser Ala Tyr Ala Asp Asp Val Glu Lys Ser Ala
     140                 145                 150 cag gga atc cgg gaa cta ctg gat gtt gct aaa cag gac att ccg ttc     654
Gln Gly Ile Arg Glu Leu Leu Asp Val Ala Lys Gln Asp Ile Pro Phe
 155                 160                 165 gac ttc tgg aag gcc acc cct ctg gtc ctc aag gcc aca gct ggc tta     702
Asp Phe Trp Lys Ala Thr Pro Leu Val Leu Lys Ala Thr Ala Gly Leu
170                 175                 180                 185 cgc ctg tta cct gga gaa aag gcc cag aag tta ctg cag aag gtg aaa     750
Arg Leu Leu Pro Gly Glu Lys Ala Gln Lys Leu Leu Gln Lys Val Lys
             190                 195                 200 gaa gta ttt aaa gca tcg cct ttc ctt gta ggg gat gac tgt gtt tcc     798
Glu Val Phe Lys Ala Ser Pro Phe Leu Val Gly Asp Asp Cys Val Ser
         205                 210                 215 atc atg aac gga aca gat gaa ggc gtt tcg gcg tgg atc acc atc aac     846
Ile Met Asn Gly Thr Asp Glu Gly Val Ser Ala Trp Ile Thr Ile Asn
     220                 225                 230
```

-continued

| | |
|---|---|
| ttc ctg aca ggc agc ttg aaa act cca gga ggg agc agc gtg ggc atg<br>Phe Leu Thr Gly Ser Leu Lys Thr Pro Gly Gly Ser Ser Val Gly Met<br>235                       240                       245 | 894 |
| ctg gac ttg ggc gga gga tcc act cag atc gcc ttc ctg cca cgc gtg<br>Leu Asp Leu Gly Gly Gly Ser Thr Gln Ile Ala Phe Leu Pro Arg Val<br>250                       255                     260               265 | 942 |
| gag ggc acc ctg cag gcc tcc cca ccc ggc tac ctg acg gca ctg cgg<br>Glu Gly Thr Leu Gln Ala Ser Pro Pro Gly Tyr Leu Thr Ala Leu Arg<br>                  270                     275                     280 | 990 |
| atg ttt aac agg acc tac aag ctc tat tcc tac agc tac ctc ggg ctc<br>Met Phe Asn Arg Thr Tyr Lys Leu Tyr Ser Tyr Ser Tyr Leu Gly Leu<br>           285                     290                     295 | 1038 |
| ggg ctg atg tcg gca cgc ctg gcg atc ctg ggc ggc gtg gag ggg cag<br>Gly Leu Met Ser Ala Arg Leu Ala Ile Leu Gly Gly Val Glu Gly Gln<br>300                       305                     310 | 1086 |
| cct gct aag gat gga aag gag ttg gtc agc cct tgc ttg tct ccc agt<br>Pro Ala Lys Asp Gly Lys Glu Leu Val Ser Pro Cys Leu Ser Pro Ser<br>315                       320                     325 | 1134 |
| ttc aaa gga gag tgg gaa cac gca gaa gtc acg tac agg gtt tca ggg<br>Phe Lys Gly Glu Trp Glu His Ala Glu Val Thr Tyr Arg Val Ser Gly<br>330                       335                     340               345 | 1182 |
| cag aaa gca gcg gca agc ctg cac gag ctg tgt gct gcc aga gtg tca<br>Gln Lys Ala Ala Ala Ser Leu His Glu Leu Cys Ala Ala Arg Val Ser<br>                  350                     355                     360 | 1230 |
| gag gtc ctt caa aac aga gtg cac agg acg gag gaa gtg aag cat gtg<br>Glu Val Leu Gln Asn Arg Val His Arg Thr Glu Glu Val Lys His Val<br>           365                     370                     375 | 1278 |
| gac ttc tat gct ttc tcc tac tat tac gac ctt gca gct ggt gtg ggc<br>Asp Phe Tyr Ala Phe Ser Tyr Tyr Tyr Asp Leu Ala Ala Gly Val Gly<br>380                       385                     390 | 1326 |
| ctc ata gat gcg gag aag gga ggc agc ctg gtg gtg ggg gac ttc gag<br>Leu Ile Asp Ala Glu Lys Gly Gly Ser Leu Val Val Gly Asp Phe Glu<br>395                       400                     405 | 1374 |
| atc gca gcc aag tac gtg tgt cgg acc ctg gag aca cag ccg cag agc<br>Ile Ala Ala Lys Tyr Val Cys Arg Thr Leu Glu Thr Gln Pro Gln Ser<br>410                       415                     420               425 | 1422 |
| agc ccc ttc tca tgc atg gac ctc acc tac gtc agc ctg cta ctc cag<br>Ser Pro Phe Ser Cys Met Asp Leu Thr Tyr Val Ser Leu Leu Leu Gln<br>                  430                     435                     440 | 1470 |
| gag ttc ggc ttt ccc agg agc aaa gtg ctg aag ctc act cgg aaa att<br>Glu Phe Gly Phe Pro Arg Ser Lys Val Leu Lys Leu Thr Arg Lys Ile<br>           445                     450                     455 | 1518 |
| gac aat gtt gag acc agc tgg gct ctg ggg gcc att ttt cat tac atc<br>Asp Asn Val Glu Thr Ser Trp Ala Leu Gly Ala Ile Phe His Tyr Ile<br>460                       465                     470 | 1566 |
| gac tcc ctg aac aga cag aag agt cca gcc tca tagtggccga gccatccctg<br>Asp Ser Leu Asn Arg Gln Lys Ser Pro Ala Ser<br>475                       480 | 1619 |
| tccccgtcag cagtgtctgt gtgtctgcat aaaccctcct gtcctggacg tgacttcatc | 1679 |
| ctgaggagcc acagcacagg ccgtgctggc actttctgca cactggctct gggacttgca | 1739 |
| gaaggcctgg tgctgccctg gcatcagcct cttccagtca catctggcca gagggctgtc | 1799 |
| tggacctggg ccctgctcaa tgccacctgt ctgcctgggc tccaagtggg caggaccagg | 1859 |
| acagaaccac aggcacacac tgagggggca gtgtggctcc ctgcctgtcc catccccatg | 1919 |
| ccccgtccgc ggggctgtgg ctgctgctgt gcatgtccct gcgatgggag tcttgtctcc | 1979 |
| cagcctgtca gtttcctccc cagggcagag ctcccctccc tgcaagagtc tgggaggcgg | 2039 |
| tgcaggctgt cctggctgct ctggggaagc cgagggacag ccataacacc cccgggacag | 2099 |

-continued

```
taggtctggg cggcaccact gggaactctg gacttgagtg tgtttgctct tccttgggta    2159
tgaatgtgtg agttcaccca gaggcctgct ctcctcacac attgtgtggt ttggggttaa    2219
tgatggaggg agacacctct tcatagacgg caggtgccca cctttcaggg agtctcccag    2279
catgggcgga tgccgggcat gagctgctgt aaactatttg tggctgtgct gcttgagtga    2339
cgtctctgtc gtgtgggtgc caagtgcttg tgtagaaact gtgttctgag ccccttttc     2399 tggacaccaa ctgtgtcctg tgaatgtatc gctactgtga gctgttcccg cctagccagg    2459
gccatgtctt aggtgcagct gtgccacggg tcagctgagc cacagtccca gaaccaagct    2519
ctcggtgtct cgggccacca tccgcccacc tcgggctgac cccacctcct ccatggacag    2579
tgtgagcccc gggccgtgca tcctgctcag tgtggcgtca gtgtcgggc tgagcccctt     2639 gagctgcttc agtgaatgta cagtgcccgg cacgagctga acctcatgtg ttccactccc    2699
aataaaaggt tgacaggggc ttctccttca aaaaaaaaaa aaaaaaaaaa aaaaaaaaa     2759 aaa                                                                  2762
```

<210> SEQ ID NO 27
<211> LENGTH: 484
<212> TYPE: PRT
<213> ORGANISM: Homo sapiens

<400> SEQUENCE: 27

```
Met Lys Lys Gly Ile Arg Tyr Glu Thr Ser Arg Lys Thr Ser Tyr Ile
  1               5                  10                  15

Phe Gln Gln Pro Gln His Gly Pro Trp Gln Thr Arg Met Arg Lys Ile
                 20                  25                  30

Ser Asn His Gly Ser Leu Arg Val Ala Lys Val Ala Tyr Pro Leu Gly
             35                  40                  45

Leu Cys Val Gly Val Phe Ile Tyr Val Ala Tyr Ile Lys Trp His Arg
         50                  55                  60

Ala Thr Ala Thr Gln Ala Phe Phe Ser Ile Thr Arg Ala Ala Pro Gly
 65                  70                  75                  80

Ala Arg Trp Gly Gln Gln Ala His Ser Pro Leu Gly Thr Ala Ala Asp
                 85                  90                  95

Gly His Glu Val Phe Tyr Gly Ile Met Phe Asp Ala Gly Ser Thr Gly
            100                 105                 110

Thr Arg Val His Val Phe Gln Phe Thr Arg Pro Pro Arg Glu Thr Pro
        115                 120                 125

Thr Leu Thr His Glu Thr Phe Lys Ala Val Lys Pro Gly Leu Ser Ala
    130                 135                 140

Tyr Ala Asp Asp Val Glu Lys Ser Ala Gln Gly Ile Arg Glu Leu Leu
145                 150                 155                 160

Asp Val Ala Lys Gln Asp Ile Pro Phe Asp Phe Trp Lys Ala Thr Pro
                165                 170                 175

Leu Val Leu Lys Ala Thr Ala Gly Leu Arg Leu Leu Pro Gly Glu Lys
            180                 185                 190

Ala Gln Lys Leu Leu Gln Lys Val Lys Glu Val Phe Lys Ala Ser Pro
        195                 200                 205

Phe Leu Val Gly Asp Asp Cys Val Ser Ile Met Asn Gly Thr Asp Glu
    210                 215                 220

Gly Val Ser Ala Trp Ile Thr Ile Asn Phe Leu Thr Gly Ser Leu Lys
225                 230                 235                 240

Thr Pro Gly Gly Ser Ser Val Gly Met Leu Asp Leu Gly Gly Gly Ser
```

```
                        245                 250                 255
Thr Gln Ile Ala Phe Leu Pro Arg Val Glu Gly Thr Leu Gln Ala Ser
                260                 265                 270
Pro Pro Gly Tyr Leu Thr Ala Leu Arg Met Phe Asn Arg Thr Tyr Lys
            275                 280                 285
Leu Tyr Ser Tyr Ser Tyr Leu Gly Leu Gly Leu Met Ser Ala Arg Leu
        290                 295                 300
Ala Ile Leu Gly Gly Val Glu Gly Gln Pro Ala Lys Asp Gly Lys Glu
305                 310                 315                 320
Leu Val Ser Pro Cys Leu Ser Pro Ser Phe Lys Gly Glu Trp Glu His
                325                 330                 335
Ala Glu Val Thr Tyr Arg Val Ser Gly Gln Lys Ala Ala Ser Leu
                340                 345                 350
His Glu Leu Cys Ala Ala Arg Val Ser Glu Val Leu Gln Asn Arg Val
            355                 360                 365
His Arg Thr Glu Glu Val Lys His Val Asp Phe Tyr Ala Phe Ser Tyr
        370                 375                 380
Tyr Tyr Asp Leu Ala Ala Gly Val Gly Leu Ile Asp Ala Glu Lys Gly
385                 390                 395                 400
Gly Ser Leu Val Val Gly Asp Phe Glu Ile Ala Ala Lys Tyr Val Cys
                405                 410                 415
Arg Thr Leu Glu Thr Gln Pro Gln Ser Ser Pro Phe Ser Cys Met Asp
                420                 425                 430
Leu Thr Tyr Val Ser Leu Leu Leu Gln Glu Phe Gly Phe Pro Arg Ser
            435                 440                 445
Lys Val Leu Lys Leu Thr Arg Lys Ile Asp Asn Val Glu Thr Ser Trp
        450                 455                 460
Ala Leu Gly Ala Ile Phe His Tyr Ile Asp Ser Leu Asn Arg Gln Lys
465                 470                 475                 480
Ser Pro Ala Ser

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 28
cgtatcccgc gggtggaggc cggggtg                                    27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 29
cttctgcaag tcccagagcc agtgtgc                                    27

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 30
```

```
ggagcccaaa agaccggctg c                                          21
```

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 31

```
tgaagtcacg tccaggacag g                                          21
```

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 32

```
cggaattcaa catgaaaaaa ggtaatccgt tatgaa                          36
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 33

```
tgtctagatg aggctggact cttctg                                     26
```

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 34

```
atcctggact tgagcctaga g                                          21
```

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 35

```
ctgatattga tgggtcttgg g                                          21
```

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 36

```
ggatggaaag gagttggtca g                                          21
```

```
<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 37
gtccacatgc ttcacttcct c                                              21

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 38
cggatccctg tgctacgtcg ccctggac                                       28

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 39
cggaattcac tggcgcaggc ggtgatctcc tt                                  32

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 40
catcctgagg agccacagca c                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 41
aggttcagct cgtgccgggc a                                              21

<210> SEQ ID NO 42
<211> LENGTH: 14747
<212> TYPE: DNA
<213> ORGANISM: Homo sapiens
<220> FEATURE:
<221> NAME/KEY: misc_feature
<222> LOCATION: (13641)
<223> OTHER INFORMATION: n = adenosine or guanine or cytosine or thymidine

<400> SEQUENCE: 42
aactagatac ccttcggaaa aggtgctaag agcccacatc accctggttt agcttgttgt     60
acaggttatt agaataggga aggaacacct tgggcccagg agtgagtgtt tcttcttttta   120 caggtgtaac taaaaaagct agttggtcta acttgtgtgt ctttgtccta taagcctctg   180
caggtgtgcg agcaggattg cttctgcaac aaaagcctcc acccagccac atcttgggaa   240
```

```
aagaatggcc acttcttggg gcacagtctt tttcatgctg gtggtatcct gtgtttgcag    300
cgctgtctcc cacaggaacc agcagacttg gtttgagggt atcttcctgt cttccatgtg    360
ccccatcaat gtcagcgcca gcaccttgta tggaattatg tttgatgcag ggagcactgg    420
aactcgaatt catgtttaca cctttgtgca gaaaatgcca ggtaagtgca actgggrccc    480
ttagtagagt ctgtaaatcc acactttagc atctcctccc agaaacaaat atgctgagag    540
tttattatgt gaattacaga atctcacacc tagtggatgt ctttcttcag agaactttgg    600
actacaattg aacatgtggg ttatttattt attttatt atttgttttg ttttattt        660 ttaactttt ttttgagaca aggtcttgct ttgttgcccg gtctgtagtg cagtggcatg      720
atgacacatc actgcaacct tgacctcctg ggctcaagca gtccttccac ctcagccccc    780
tgagttgttg agactacagg cttgtgccac catgcccagc tcatttttaa atttttttat    840
agagacctgc tcagactggc tcaaactcc taggctcaat tgatcctccc acctcagcct     900
cccaaagtac tggattata gtgtaagtc accatgcttg ccagaacac atggcttaat       960 tcaatgtgaa attagaagag agctgggctg tctgtagtct gaaacccatg tgttcaaaaa   1020
gaatagttat aatttgttct tcctctttaa acatgggata ctccagggat ccataatatt   1080
cagaatatgg ggagtggttt tgggagaagg atcacatgag aatttcactg ccatccttgg   1140
acatgaggct aggaatccct gaagattaac ttttctgaa tttgtcagtg ttttttcctc    1200
aggtcactta tggagcctgg ggaaaggtgg aggagttagg tgtccaccag agaaatggta   1260
gcagaaatgg accctcagag gttgctctag tccttctttc cagtactcct gcaagacatt   1320
cctcacaact aggatcattg gggtaacttc agggaagtca taggaaaact tacagagaca   1380
gagcccagca tctgaagcag cctaactttt ggtaaccagc tctctcttct gttttgttcc   1440
atggacaaaa taggacagct tccaattcta gaagggaag tttttgattc tgtgaagcca    1500
ggactttctg cttttgtaga tcaacctaag caggtgagyt tcttatgatt tgatgtttag   1560
attctcratg ccttgataac ttgaccacac cactgctgtt aaatatttca tgctattcac   1620
taatgagatt gagatcatgt gtgagatcag ctttctctcc tcagctaatc tcctggataa   1680
aattaattac atttcccacg ctcatgaggg ctgggtggaa gaaggctaga aaattggttg   1740
tggtaatgca aggatgacac tagctttaa gagattactc cctatgtact tactgtttaa    1800
aattttgagt tgaagccatc agttgtattt gttcatgtaa gcgcagaaga taaacatgaa   1860
gttctgtagg gtatgatgta taaacatggc agttgaaggc atggtgagca gtgaattcca   1920
tttcagagtg ccttgatgca ggatggaacc atatctatac ttgagaaatt aggcaacaac   1980
ccatgatgac aaaaatcttt ggtggtagaa gatgaataga gagtttgtgg cgactatatt   2040
tcacatttga gcatctacaa catactacat cctatgtgtc tgaggccatg ttgaaataaa   2100
atagaataat gcagaatgtt aaacttgggg agcaaatgta aagtattta ttgttcattg    2160 tcacaagaat aatcattacc caaatgcttg atgttaaaaa tgatttgagt ttggagaact   2220
gagaggatat atggatatat atacattttc ttcttttct tttttttttt tttttgacg     2280 gagtatcact ctgttaccca ggctggagtg cagtggcctg atctcggctt actacaacct   2340
ctgcctcgcg ggttcaagca attcttctgc ctcagcctcc cgagtagctg ggactacagg   2400
catgtgccac catgcccggc taattttgt attttagta gagacggggt ttcactatga     2460
tggycaggct ggtcttgaac tcctgacctt gtgatccrcc catgtcagcc tcccaaagtt   2520
ctgggattac aggtgtgaga caccactgcg cctggcctgg attctccttc aaagcggccc   2580
```

```
acttctctag gtttctcctg ctacagagca gagagaggtt ggagccctat gccacctccc   2640
tcttcttgct cccasaaagt atgttgacag aatagaccag tgccagccac taaatggatc   2700
gttcatcaga tgaacgggtt atctcttttg aagggtgctg agaccgttca agggctctta   2760
gaggtggcca aagactcaat cccccgaagt cactggaaaa agacccagt ggtcctaaag    2820 gcaacagcag gactacgctt actgccagaa cacaaagcca aggctctgct ctttgaggta   2880
agttttaaaa ctgcatcttg gatcattctg ccctttccc tatatgaata ctttatgagt    2940
ttttagcctt ttggaatgtg accactacct tcagtattcc accatgcca aagcattgtg    3000 atgactctga ccacttgtta tagctagttg tttacatttt taactatcac tcttaaatgt   3060
atagagcttt tcctaaaaaa tttaaagtac tttctatcta ggatattctt cattcttttt   3120
atttttattt ttattttttg agatggagtc tcactctgtc acccaggctg gagtgcagtg   3180
gcgccatctt ggctcactgc aagctccacc tcccaggtta atgccattct cctacctcag   3240
cctcccaggt agctgggatt acaggtgccc accaccatgc taatttttt gtattttag    3300 tagagatggg gtttcatcat gttggccagg ccggtctcga actcctgacc tcaggtgatc   3360
cacctgcctc ggcctccaaa agtgctggga tgagaggtat gagccaccat gcccggctgc   3420
cactggaagg ttttgagcca aggaaacaca tgatttgacg tccatttta aagcaccgtt    3480 ctggctgctg ttttgagaac aaactgtagg atggggagagaaagtggaga aggcaagagc    3540 agaagctctc ttgctgtgct tcatcctgtt cacttatctg tctttaaaag tttgtttata   3600
tataacttaa ctgttttttc ctggttgaaa caggatccag aggtcattat gtggtatgtt   3660
tcatccatca gaaatgagaa cagcaaacag actagcgttc ttcctatcct attcggagaa   3720 ttctttttc tttcccttga taattatata aacataagac attaacaccc atatcaatgg    3780
tctgtattat ggagaggcaa gatgttttg caagatcgtc attcccatct cctgaaacag    3840
gattccttaa gtctagatct ggagtctccc catgctctag agaccctagc catgtgccag   3900
aatctgacag gagctggtag cagagtacct cagcccttag gtgtgaactt caccacagca   3960
ggttcatgtc agctcatcta aggaatggag tgggaaggct cctcctagtt tccagtgtat   4020
gtccaggtag agtttatcag gtttaaaagt tacaggatcc tgatttgagc tggcagggtt   4080
aaatatatgc ctttccatag gtccagttca cctatacatt tagatggttt ggtttagctt   4140
tacttaaagt caaaggaatc tctgtgtttg tgttttgca agaaactggt aatggcttgc    4200
ctagttttct ctctagtttc ttagggcaaa ggaatgagtt ttgccaaaat tttatctagg   4260
aaaaatggag tagtttcta agtcttacag aacactgtca aaatatggaa atctatttta    4320
ttgccttagg gaattctttt ttttttttt ccttttctc taggtaaagg agatcttcag     4380
gaagtcacct ttcctggtac caagggcag tgttagcatc atggatggat ccgacgaagg    4440
tgggagaggt gttgatatgc gttccagggg gagagggca ggatcagtga agatctaac    4500 taaaggaact ggggccagga ataaacagaa ggaatgagat agcaggaaat agaagacagg   4560
gagaagggaa catgtgctct agacatgaa tttagagagg aaaaaaaaa aacaaggttg    4620 gggccaggaa agagaaaaaa tgctctggga tctaatcctt gtctttcttt cttttaggc   4680 atattagctt gggttactgt gaattttctg acagtaata catcctcaag tttatcttta    4740
gagcttaact agcttttaca tgcatagtca gaggagtaaa agcctcttct ttcattctgt   4800
attgtttctt cttcttaaaa aaggaaaag aggctgggtg tggcagttca tgcctgttaa    4860
ttccagcgct ttgggaggct gagttgggca gatcacttga ggccaggagt tcaagaccag   4920
cctggccaac atggcgaaac tccgtctcta ccaaaaatac aaaaatagct gggcatggtg   4980
```

-continued

```
gtgtgtacct gtagtcccag ctactcagga ggctggagaa tcacttgaac ccaggaggca    5040
gaggttgcag tgagctgaga gccgagattg cgccactgca ctccaggctg gatgatagag    5100
caagactctg tctccaaaaa ggccttccaa aaaaaaaaaa aacacctgcc ttgaaggcct    5160
ctgctgcaac aagagtcctt ccgagttgac attcacctgc agccttgggg ctggggagca    5220
gtggagtata tatggaatac cttcagtgta tgataagagc aagagagaca agtgttgggc    5280
tgcccaggat gtcgaggcta tttagagctg gctctcattt gacaggtcag ctgcatggcc    5340
acagacagga gactgtgggg accttggacc taggggagc ctccacccaa atcacgttcc     5400
tgccccagtt tgaggtgagt catttaatga agatctggtt agaagtgcac ttggcaggcg    5460
tatcatggtg ccaagaaaga ggcgccccat tttcagccag cagctctacc acgcttaggc    5520
agagtcaagt caattaataa ctaggtgaat gttcccttgc catctcactg ttcagaatcc    5580
cttcgtttcc tcaagcctag tgagattagc cccttaatct gtcttcatct ctgatttttt    5640
gctgggaggg acgggtggtg gtgtgaacat cttcaggtaa ttacagatcc tgaatagtct    5700
ttttgctttt tctgatttgc agaaaactct ggaacaaact cctaggggct acctcacttc    5760
ctttgagatg tttaacagca cttataagct ctatacacat aggtgaggac ggggacaggg    5820
aagaagaata tttcatgttg tatgattctc ctaactttcc aaagcattct caaatctgtt    5880
attgtatctg attagcaaaa acaaagtctg tgccaattcc ctaaggccta tcaactgaaa    5940
cccggtccac ttacaaagcc ggaggagcct aagaggcttc tccattcttg gcctcaaaag    6000
cattaatata tgacttaaga gtcaaaagtt ttcggctggg tgcagtggct tcatgcctgt    6060 aatcccctgca ctttgggagg ccgaggtggg tgggtcacct gaggtcaggc gtttgagacc    6120
agcctggcaa acatggtgaa accccgtctc tactaaaata caaaaattag ctggatatga    6180
cagcgcacac ctgtaatcct agctattcag gaggctgagg caggagaatc atttgaaccc    6240
tggaggcgga gattgcagtg agccgagatc acaccactgc acttcagccg gagcgacaga    6300
gcaagactca gtctcaaaaa aaaaaaaaaa aagaatcaaa agctttctgt agggagagga    6360
cacttcaaga aggctcaggc aaagctcctt gccagctcct ttgagctggc cttcagaggt    6420
tcagaatcca gcctggaatg tgatcccagt tggggctagg agctaagcta aagagagctt    6480
ttctgggaat ggttcctagt gtgggaccct aggaattgtc actgtctctg gcctttgaat    6540
gataactgtg gggaattctt actgcatagc cttgatccaa actgtgcaga aattacccct    6600
tgttgaccac aggagatgaa tatgtcacag acagaacaag gttttcatct ttccagaggg    6660
acacaggaac aatgttactt ttgaaagagg tagctttagg ctagagaact tcaggaccag    6720
catgaaatta gtcaatcctg tattttacag ttacctggga tttggattga agctgcaag    6780 actagcaacc ctgggagccc tggagacaga aggtttgtct gggtacctgt gctgggggg    6840 gatggtgagg gtgacacaga tactccgctt gcttcttccc ttccttgata gccattctat    6900
ggaggaaaag attatgttga attgggaggc aaatgttgta taatggacct aataatggca    6960
aactcctttt ctagtttata agttcagaag ttttgatgta tattattagc cattttaga    7020 atgaggtcta cttgttcagg ggtaacagcc tatgtctagg cagctgaagt gtctgcagaa    7080 atccaggct ttacgaatac attcagcagg agcttgctca agccctgagc tttacattgg     7140
aggcacagga agcagagtct gttctacatg caggtggaac aacagagtaa ctccattgat    7200
ctcttcacag gtcaggcaga actgggttca gtcccagtgt tgtgatatga ggcgagtaac    7260
ctatctgtgc ccctttcctc acattaaatg agaatttgca tttaaggcac tttgtacagt    7320
```

```
aatctgttat tgggatgaca tctattttgc atttcagagt atacaaaaca tcttcaagta   7380
tatttaattg aagcctctca gcaaccagtg aggaaggtag catagcattt ctttcctgtt   7440
tttataaagg tggaaagttg ctgtattgaa ggttttggat ctctttgaga tgtgatgaaa   7500
gccatggacc cctctgacaa aagcacatat gcatgaaaat ttgcttctgg tttcaggggg   7560
ttcaccaacc ccacaaagcc tatctttgaa ccctgagtta aggattcctg tcacaggatg   7620
ttgtcatgga attaatttca taggatttta aggcccagcc ccatggtga ttcttttcca    7680 cctcactggc ttcttgcttg ccttcctccc tctctctcac ttacttacct cttaccttgt   7740
gccctggatt ctttcaggga ctgatgggca cactttccgg agtgcctgtt taccgagatg   7800
gttggaagca gagtggatct tgggggtgt gaaataccag tatggtggca accaagaagg    7860
caagtgatgt tttttcactg gttaaagtta cgtttacaat ggaagctctg aaaagtccc    7920 atgggaaact ttttccagaa ctcaagagaa gcttatcttg ttgcagggac ttattccaaa   7980
gatcttggca tgcctccaag gactaatgtg aagtgacagt gaacaaagca gctgtcattc   8040
tgcatcagcc aagtgtcatg gacccattag ataccctgccc ttagccaagt gctgtggtgc  8100
acatctattg tcctagctac tccaaaggtt gaggcaagag gatcacttga gcccatgagt   8160
tcaaggctat agtgcgcaat gccactgcac tccagcctgg gcaacaggga gacctacct    8220 cttacaaatt aattaagaag catattctaa gcctaggtct aatgcagcag tgtgaaagcc   8280
tgtttagtta atggttagct atttaaatta tagtaaaact taaaccaag acaagaatga    8340 ttcatcttct tataaaaggt atatacctga atatcaagga atgaacctga attcccagtg   8400
aaggaagcag gcgagccctt tagctacttg cttacaaatg ctatggaatg taatgctagg   8460
cagcagcaca aggttggcca tgatctggtg aatacagatt aggcaggaga gcggccatgg   8520
agaaacagac tggtgaggct gcagacgttt gctcatcttt gttttgacgc ctcttgtccc   8580
aagcctcagc cttctcctgc tttccttgac cttcctgctg ttccctcatt gtctccagca   8640
gcctgcctca gagagtgtcc ccttccccca gcgtcgttct caccttaccc ctgtgcacct   8700
ttgcctggca ggggaggtgg gctttgagcc ctgctatgcc gaagtgctga gggtggtacg   8760
aggaaaactt caccagccag aggaggtcca gagaggttcc ttctatgctt tctcttacta   8820
ttatgaccga gctgttgaca cagacatgat tggtgagttc accccaggtg tcagtccaga   8880
gaggaaggtg gatagggctg tggtggggaa ggtcaaggag aaagagcact tgaggtgctt   8940
tgtcggggtc attacccacc tcttttctag tcactcgaac aaaagggtgg aaatgactta   9000
gagtcttttg gaggtgagag atgaccaaaa caactatatg aggtcttttt ttttttaaca   9060
tgtttattga ggtataattg gcatacaata agtgccacat ttaaagtata caatttaagt   9120
tttgtcatgt atacacccat gaatccatcc agcacattga agataataaa catatttcac   9180
cacaaaaagt ttcctcctgt ctctttataa cttttcttct tatcacaaaa gcagtgtttt   9240
tgcctaactg tgaaagtata tgtacctgat ctgtcatggc ctgagagaga tgaattaatt   9300
tcctattatt gtgggggttt tgttgttgtt gttgtttttgg ttttttgttt gtttgtttgt   9360
tttttgagac agagtctcac tctgttaccc aggctggagt gcaatggcat gatctaggct   9420
cactgcaacc tctgcctccc gggttcaacc gattctcctg ccccagtctc ctgagtagct   9480
gggattacag gtgcctgcca ccacacccgg ctaattttt ttttaataga gacgaggttt    9540
caccatgttg gtcaggctgg tcttgaactc ctgacctcgt tatctgcctt cctcggcctc   9600
ccaaagtgct gggattacag gcatgagcca ccacacccgg cctattgtgt tttatgggtc   9660
tgttttttcc attgtggtta aatatacata acatggaata gattgtaaat aagtaaatta   9720
```

```
ggttgcatag attacattat gtacatgtgt atataatgaa tgaatgaatg aatttcctta    9780
tgcttccttg aaggcgtttt gatatcagat aatcttctgt tttatttcag attatgaaaa    9840
gggggggtatt ttaaaagttg aagattttga aagaaaagcc agggaagtgc aagttcttca    9900
gaagttgcgg tcttacagag gcagtcagtg cagtttagtc tttgagatgc ctaagcatta    9960
accaaaggga gacttcwgct ttgcttattc ttcttctccc cctaccttt ttttttgaga   10020
cagagtcttg ctctgtcacc caggctggag tgcagtggtg agatctcggc tcactgcaac   10080
ctctgccttc caggttcaag cgattctcct gcctcagcct cccgagtagc tgggattaca   10140
gcggtacacc accacgccgt gctaattttt gtattttag tagagatggg gtttcaccac   10200
gttggccagg ctgatctcaa actcctgacc tcaggtgatc cacccgcctc agcctcccaa   10260
agtgctagga ttacaggcgt gagccaccgc gcctggcccc tattccactt ctttctaaga   10320
gaaaatccta cacctctcag ttagttgcaa acttgagctc cactgttwac tctctctttc   10380
agtgtgtgat aacttggaaa acttcacctc aggcagtcct ttcctgtgca tggatctcag   10440
ctacatcaca gccctgttaa aggatggctt tggctttgca gacagcacag tcttacaggt   10500
aagagacagg acaccagagt ctcataacag ccctcttttg tggggttga aaggagtaa    10560
gagcttgttc agtaatcaga gtagctagaa gtgaaattat gaggtatttt tgtttgggct   10620
atggacaagg tactgtgctg ggcaccatga atgtgggaaa ttatctcaat gcaatggtag   10680
cctccgagtg tattaccagg caagctatcg cacaggtcac agaacagaaa gactagcagc   10740
ccaaattaag atgccaagtc acatggttta tttatttatt tatttattta ttattatttt   10800
tttgagacgg agtctygctc ttgttkccyr ggctggagtg cartggcryg atcwcrgctc   10860
actgcarcct ycrcctcctg ggttcaagcg attctyctgc ctcagcctcc cragtagctg   10920
ggattacagg crygcgccac cacgccyggc taatttttt gtattttag tagagacggg   10980
gtttcaccat gttggccagg ctrktctyra actyctgayc tcaggtgatc caccrcctc   11040
rgcctcccaa agtgctrgra ttayaggyrt gagccaccac kccyrgcctt ttttgktcgk   11100
ttctttttt ttchtttttt tttttttttt gagacagggt cttgctctgt cacccatgct   11160
ggagtgcagt ggcatgatct cagttcactg caacctctgc ctcccgggtt caagtgaccc   11220
tcccacctca gcctctgag tagctgggat tacaggtgtg tgccaccact cttgtctaat   11280
tttttgtag agacgggtt ttgccatgtt gcccaggctg tcttgaact cctggcctca   11340
agcaatccac ctgccttggc ctcccaaagt gccaggagta caggcatgag ccactgcgcc   11400
tggccccatg tttggttatt attagtgctt aggaagaggc acttgcttac atagtaggag   11460
ttgagaagct tggtttgttc tttcctaccc ctagatctat tctcacctcc tgaccatgct   11520
ctttctgcca catctattat cattacaagt tgccttatct gaaattagtg aatcagaaaa   11580
taaagcaggg atactttgt gtagtttcaa cgttagggaa agttcagaat actgtctgtc   11640
taaactatct ctctagaagg cctgatgggc cacaacctgg gccagaagca ttcagttcag   11700
atatgagaat ggtgggtgta ggggcaatgg ccaatgggcc atggccggaa ggaaattgtt   11760
acagagtagt gggaagcctg caaagactgg cttctgtccg ttttgccttg gtttgcccat   11820
gtggatattc tttgccaata ttttctgccc aagagctgtg cttgctagag ttggaaactg   11880
gatgaaaagg tgaagacttt ttttcttctc aacagctcac aaagaaagtg aacaacatag   11940
agacgggctg ggccttgggg gccaccttc acctgttgca gtctctgggc atctcccatt   12000
gaggccacgt acttccttgg agacctgcat ttgccaacac ctttttaagg ggaggagaga   12060
```

```
gcacttagtt tctgaactag tctggggaca tcctggactt gagcctagag atttaggttt    12120
aattaatttt acacatctaa tgtgaactgc tgcctaacca ctcaagagta cacagctggc    12180
accagagcat cacagagagc cctgtgagcc aaaaagtata gttttggaac ttaaccttgg    12240
agtgagagcc cagggacagg tccctggaaa ccaaagaaaa atcgcatttc aacccttttga   12300 gtgcctcatt ccactgaata tttaaatttt cctcttaaat ggtaaactga cttattgcaa    12360
tcccaagacc catcaatatc agtattttt tcctccctat acagtgccct gcccacccttt    12420 atctgcaccc acctcccctg aaaaagagag aaaaaaaaaa acctggtttt gctttccatg    12480
tataattcaa caacgcaaaa tggtaccatg tcagaatctg tatgatccta ttctgtgtta    12540
gctccaatca gccagctgag agccatccta aatattaata ggatgagaga gtaactccta    12600
actgtgcata aattacagcc ttaagaaaga aggccacccg gtctctgggg acatgttttg    12660
ggagggtgtg gctgcctcat atagcctacc tttgctttaa tcagcatttt atcagtcaac    12720
tctgggatta atgaacatat ccgactttat gggtatgtgt atattcagtg ccagtaccac    12780
ctcccaggct aatgtgttaa cagtgttttc tatgattcta aacttgtttt ctttgtattt    12840
ctaagaaata caactaggcc ctaactttg gtctgtggtc agaggtcagt gtctgtgcta    12900
ttccaggatc tattatttca gtttgccctt ttattctctc cgtttgtaac agtaccttcc    12960
tgtcctggtc cctgatcact ttagctaata tcctttgaat tatttatcta gttcagagtt    13020
tccaataccg ttcctgacaa accccacttt ggatttggtt ggctctctca gcccacatca    13080
gtacagtgga ccaacatttc cagggagaac catatttaat gtccctcatg ctctcttttt    13140
gaatccaagt gctcagagct cttgactgtg aattatttac cccaaattca ttatcttgca    13200
cttttttttg agatggagtc tcgctctgtt gctcaggcta gagtggagtg gcgcaatctc    13260
agctcactgc aacctccgcc cccaggttca agcgawtctt gwtctcagcc tcctgaagag    13320
ctgggattac aggtgtgagc cactgcaccc atcagaaaaa acatatcttt aaatggaagt    13380
tctcagggat gaaactagtc aagcagcaaa aggagcttaa acatcttcat cattagaaat    13440
ccctattcat ttttttttc aagagactgg tcttaactct gtcacccagt ctgagtaaca    13500
atgatgtgat catagcccac tgcagcctca aactcctagg cttaaattat cctcttgcct    13560
cagkctcctg aatagctagg actacaggca tgtgccacca cactccctat tcactatttt    13620
taagcccttt ttatacatag ntattgctta gatgtgggcc gtaacaccta aaagcctagc    13680
aagtactctt ctgcttgtaa cccttgggaa ggcaaacaca taaagataat acatttaca    13740 gccaagaaaa ttaattcaaa gaaattaaga gctgtgggcc agccgcagtg gctcacgcct    13800
gtaatcccag cactttggga ggccgaggca ggcagatcac gaggtcagga gttcaagacc    13860
agcttggcca acatggtgaa accccatctc tactaaaaat aagaaaatta gccgggtgtg    13920
gtggtgggcg cctgtaatcc cagctacttg ggaggctgag gcaggataat cacttgaacc    13980
tgggaggcag aggctgcagt gagtggaaat tgtgccactg cactccatcc tgggcgataa    14040
gaccaagact ctgtttcaaa aaaagcaaaa agaaattaag agctgtttgc aaagtcattc    14100
ctctgagcaa cctcttactt tgagtggaga cactgcattt gtggcctgca agccccacgt    14160
cctgagcaac acaagcgggg aggcactggt agaatagagc cttttttagta agtctgtagc    14220 agccagaaga gcagtgttgt gacgctgtct ttctgtttca taacctgtga ggtggctcac    14280
ggaacctgaa gggcagagga aagattaaat ccctaatcca ataataaggt tttcttccat    14340
ctcctagcaa gccagatata ttttatgtcc actccctctt gctactgtgg gccctgatct    14400
tgcctaacta tatgacctct ggatacttcc ccatagtacc tgaatcctta cctaagtcct    14460
```

-continued

```
tcccattgaa ggctgccgta ctgaggtgat gggccaagct ggagatatcc ccaaagccca    14520
tgttgacacc ctgtcctgca agcggatgga ctctgtgggc tgcatccta agaataaagc    14580 agagttcagg tgtgacctct ggcagcaaag tgagaaggga gtggccctgc tctgtatcgt    14640
cttacccaat gagcgccacc cgaggcctga cgtactcagc agcatgttcc aacccaagag    14700
gaaacagaac tcggcttttg gcatccaccc tgggctaccc cttgggg                  14747
```

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: peptide

<400> SEQUENCE: 43

Glu Val Ala Lys Asp Ser Ile Pro Arg Ser His Trp Lys Lys
 1               5                  10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: peptide

<400> SEQUENCE: 44

Thr Arg Pro Pro Arg Glu Thr Pro Thr Leu Thr His Glu Thr
 1               5                  10

<210> SEQ ID NO 45
<211> LENGTH: 1498
<212> TYPE: DNA
<213> ORGANISM: Homo sapiens

<400> SEQUENCE: 45

```
atgaaaaaag gtatccgtta tgaaacttcc agaaaaacga gctacatttt tcagcagccg    60
cagcacggtc cttggcaaac aaggatgaga aaaatatcca accacgggag cctgcgggtg    120
gcgaaggtgg catacccct ggggctgtgt gtgggcgtgt tcatctatgt tgcctacatc    180
aagtggcacc gggccaccgc cacccaggcc ttcttcagca tcaccagggc agccccgggg    240
gcccgtgggg gtcagcaggc ccacagcccc ctggggacag ctgcagacgg gcacgaggtc    300
ttctacggga tcatgtttga tgcaggaagc actggcaccc gagtacacgt cttccagttc    360
acccggcccc ccagagaaac tcccacgtta acccacgaaa ccttcaaagc agtgaagcca    420
ggtctttctg cctatgctga tgatgttgaa agagcgctc agggaatccg gaactactg    480 gatgttgcta acaggacat tccgttcgac ttctggaagg ccaccctct ggtcctcaag    540 gccacagctg gcttacgcct gttacctgga gaaaaggccc agaagttact gcagaaggtg    600
aaagaagtat ttaaagcatc gcctttcctt gtagggatg actgtgtttc catcatgaac    660
ggaacagatg aaggcgtttc ggcgtggatc accatcaact tcctgacagg cagcttgaaa    720
actccaggag ggagcagcgt gggcatgctg gacttgggcg aggatccac tcagatcgcc    780 ttcctgccac gcgtggaggg caccctgcag gcctccccac ccggctacct gacggcactg    840
cggatgttta acaggaccta caagctctat tcctacagct acctcgggct cgggctgatg    900
tcggcacgcc tggcgatcct gggcggcgtg gaggggcagc tgctaaggta tggaaaggag    960
ttggtcagcc ttgcttgtc tcccagtttc aaaggagagt gggaacacgc agaagtcacg    1020
```

-continued

| | |
|---|---|
| tacagggttt caggcagaa agcagcggca agcctgcacg agctgtgtgc tgccagagtg | 1080 |
| tcagaggtcc ttcaaaacag agtgcacagg acggaggaag tgaagcatgt ggacttctat | 1140 |
| gctttctcct actattacga ccttgcagct ggtgtgggcc tcatagatgc ggagaaggga | 1200 |
| ggcagcctgg tggtggggga cttcgagatc gcagccaagt acggtgggag tcacctggag | 1260 |
| cgtgaaggga cgtgtctcat ccccagtgtg tcggaccctg agacacagc cgcagagcag | 1320 |
| ccccttctca tgcatggacc tcacctacgt cagcctgcta ctccaggagt tcggctttcc | 1380 |
| caggagcaaa gtgctgaagc tcactcggaa aattgacaat gttgagacca gctgggctct | 1440 |
| gggggccatt tttcattaca tcgactccct gaacagacag aagagtccag cctcatag | 1498 |

<210> SEQ ID NO 46
<211> LENGTH: 2371
<212> TYPE: DNA
<213> ORGANISM: Homo sapiens

<400> SEQUENCE: 46

| | |
|---|---|
| gtggggtcgt atcccgcggg tggaggccgg ggtggcgccg gccggggcgg gggagcccaa | 60 |
| aagaccggct gccgcctgct ccccggaaaa gggcactcgt ctccgtgggt gtggcggagc | 120 |
| gcgcggtgca tgaaactccc acgttaaccc acgaaaacctt caaagcagtg aagccaggtc | 180 |
| tttctgccta tgctgatgat gttgaaaaga gcgctcaggg aatccgggaa ctactggatg | 240 |
| ttgctaaaca ggacattccg ttcgacttct ggaaggccac ccctctggtc ctcaaggcca | 300 |
| cagctggctt acgcctgtta cctggagaaa aggcccagaa gttactgcag aaggtgaaag | 360 |
| aagtatttaa agcatcgcct ttccttgtag gggatgactg tgtttccatc atgaacggaa | 420 |
| cagatgaagg cgtttcggcg tggatcacca tcaacttcct gacaggcagc ttgaaaactc | 480 |
| caggagggag cagcgtgggc atgctggact gggcggagg atccactcag atcgccttcc | 540 |
| tgccacgcgt ggagggcacc ctgcaggcct cccaccccgg ctacctgacg gcactgcgga | 600 |
| tgtttaacag gacctacaag ctctattcct acagctacct cgggctcggg ctgatgtcgg | 660 |
| cacgcctggc gatcctgggc ggcgtggagg gcagcctgc taaggatgga aaggagttgg | 720 |
| tcagcccttg cttgtctccc agtttcaaag gagagtggga acacgcagaa gtcacgtaca | 780 |
| gggtttcagg gcagaaagca gcggcaagcc tgcacgagct gtgtgctgcc agagtgtcag | 840 |
| aggtccttca aaacagagtg cacaggacgg aggaagtgaa gcatgtggac ttctatgctt | 900 |
| tctcctacta ttacgacctt gcagctggtg tgggcctcat agatgcggag aagggaggca | 960 |
| gcctggtggt gggggacttc gagatcgcag ccaagtacgt gtgtcggacc ctggagacac | 1020 |
| agccgcagag cagcccccttc tcatgcatgg acctcaccta cgtcagcctg ctactccagg | 1080 |
| agttcggctt tcccaggagc aaagtgctga agctcactcg gaaaattgac aatgttgaga | 1140 |
| ccagctgggc tctgggggcc attttttcatt acatcgactc cctgaacaga cagaagagtc | 1200 |
| cagcctcata gtggccgagc catccctgtc cccgtcagca gtgtctgtgt gtctgcataa | 1260 |
| accctcctgt cctggacgtg acttcatcct gaggagccac agcacaggcc gtgctggcac | 1320 |
| tttctgcaca ctggctctgg gacttgcaga aggcctggtg ctgccctggc atcagcctct | 1380 |
| tccagtcaca tctggccaga gggctgtctg gacctgggcc ctgctcaatg ccacctgtct | 1440 |
| gcctgggctc caagtgggca ggaccaggac agaaccacag gcacacactg aggggggcagt | 1500 |
| gtggctccct gcctgtccca tcccatgcc ccgtccgcgg ggctgtggct gctgctgtgc | 1560 |
| atgtccctgc gatgggagtc ttgtctccca gcctgtcagt ttcctcccca gggcagagct | 1620 |
| cccccttcctg caagagtctg ggaggcggtg caggctgtcc tggctgctct ggggaagccg | 1680 |

| | | |
|---|---|---|
| agggacagcc ataacacccc cgggacagta ggtctgggcg gcaccactgg gaactctgga | 1740 |
| cttgagtgtg tttgctcttc cttgggtatg aatgtgtgag ttcacccaga ggcctgctct | 1800 |
| cctcacacat tgtgtggttt ggggttaatg atggaggag acacctcttc atagacggca | 1860 |
| ggtgcccacc tttcagggag tctcccagca tgggcggatg ccgggcatga gctgctgtaa | 1920 |
| actatttgtg gctgtgctgc ttgagtgacg tctctgtcgt gtgggtgcca agtgcttgtg | 1980 |
| tagaaactgt gttctgagcc cccttttctg gacaccaact gtgtcctgtg aatgtatcgc | 2040 |
| tactgtgagc tgttcccgcc tagccagggc catgtcttag gtgcagctgt gccacgggtc | 2100 |
| agctgagcca cagtcccaga accaagctct cggtgtctcg ggccaccatc cgcccacctc | 2160 |
| gggctgaccc cacctcctcc atggacagtg tgagccccgg gccgtgcatc ctgctcagtg | 2220 |
| tggcgtcagt gtcggggctg agccccttga gctgcttcag tgaatgtaca gtgcccggca | 2280 |
| cgagctgaac ctcatgtgtt ccactcccaa taaaaggttg acaggggctt ctccttcaaa | 2340 |
| aaaaaaaaa aaaaaaaaa aaaaaaaaa a | 2371 |

<210> SEQ ID NO 47
<211> LENGTH: 1900
<212> TYPE: DNA
<213> ORGANISM: Homo sapiens

<400> SEQUENCE: 47

| | | |
|---|---|---|
| gggggaatgt agggcagatg gtcccaacag gccagaggcc actggtgtca ggcatcagca | 60 |
| gcttcctcct cagagtccag gtctgccgct gccttcgtgc ccacggtctt cactccctgc | 120 |
| gccgggacca acaatgccct ggctcctgag ggctgctttt gacctgtgcg gggagcagcc | 180 |
| ccaacttggg gtggggtctt acaggcttct ggacctgcct tttcctgaca attcaggtca | 240 |
| gagtctcaag tcccctggga ggggcccaa gcagctgtga ggcctgggtg ctcggagccc | 300 |
| actgaccgct agccttgtgc ttgtcccag cggcaagcct gcacgagctg tgtgctgcca | 360 |
| gagtgtcaga ggtccttcaa aacagagtgc acaggacgga ggaagtgaag catgtggact | 420 |
| tctatgcttt ctcctactat tacgaccttg cagctggtgt gggcctcata gatgcggaga | 480 |
| agggaggcag cctggtggtg ggggacttcg agatcgcagc caagtacgtg tgtcggaccc | 540 |
| tggagacaca gccgcagagc agccccttct catgcatgga cctcacctac gtcagcctgc | 600 |
| tactccagga gttcggcttt ccaggagca aagtgctgaa gctcactcgg aaaattgaca | 660 |
| atgttgagac cagctgggct ctgggggcca tttttcatta catcgactcc ctgaacagac | 720 |
| agaagagtcc agcctcatag tggccgagcc atccctgtcc ccgtcagcag tgtctgtgtg | 780 |
| tctgcataaa ccctcctgtc ctggacgtga cttcatcctg aggagccaca gcacaggccg | 840 |
| tgctggcact ttctgcacac tggctctggg acttgcagaa ggcctggtgc tgccctggca | 900 |
| tcagcctctt ccagtcacat ctggccagag ggctgtctgg acctgggccc tgctcaatgc | 960 |
| cacctgtctg cctgggctcc aagtgggcag gaccaggaca gaaccacagg cacacactga | 1020 |
| gggggcagtg tggctccctg cctgtcccat cccatgccc cgtccgcggg gctgtggctg | 1080 |
| ctgctgtgca tgtccctgcg atgggagtct tgtctcccag cctgtcagtt tcctccccag | 1140 |
| ggcagagctc cccttcctgc aagagtctgg gaggcggtgc aggctgtcct ggctgctctg | 1200 |
| gggaagccga gggacagcca taacacccc gggacagtag gtctgggcgg caccactggg | 1260 |
| aactctggac ttgagtgtgt ttgctcttcc ttgggtatga atgtgtgagt tcacccagag | 1320 |
| gcctgctctc ctcacacatt gtgtggtttg gggttaatga tggagggaga cacctcttca | 1380 |

```
tagacggcag gtgcccacct ttcagggagt ctcccagcat gggcggatgc cgggcatgag    1440
ctgctgtaaa ctatttgtgg ctgtgctgct tgagtgacgt ctctgtcgtg tgggtgccaa    1500
gtgcttgtgt agaaactgtg ttctgagccc ccttttctgg acaccaactg tgtcctgtga    1560
atgtatcgct actgtgagct gttcccgcct agccagggcc atgtcttagg tgcagctgtg    1620
ccacgggtca gctgagccac agtcccagaa ccaagctctc ggtgtctcgg gccaccatcc    1680
gcccacctcg ggctgacccc acctcctcca tggacagtgt gagccccggg ccgtgcatcc    1740
tgctcagtgt ggcgtcagtg tcgggctga gccccttgag ctgcttcagt gaatgtacag     1800
tgcccggcac gagctgaacc tcatgtgttc cactcccaat aaaaggttga cagggcttc     1860 tccttcaaaa aaaaaaaaaa aaaaaaaaaa aaaaaaaaa                           1900

<210> SEQ ID NO 48
<211> LENGTH: 2693
<212> TYPE: DNA
<213> ORGANISM: Homo sapiens

<400> SEQUENCE: 48
gtggggtcgt atcccgcggg tggaggccgg ggtggcgccg gccggggcgg gggagcccaa      60
aagaccggct gccgcctgct ccccggaaaa gggcactcgt ctccgtgggt gtggcggagc     120
gcgcggtgca tgcagccgca gcacggtcct tggcaaacaa ggatgagaaa aatatccaac     180
cacgggagcc tgcgggtggc gaaggtggca taccccctgg ggctgtgtgt gggcgtgttc     240
atctatgttg cctacatcaa gtggcaccgg gccaccgcca cccaggcctt cttcagcatc     300
accagggcag ccccgggggc ccggtggggt cagcaggccc acagccccct ggggacagct     360
gcagacgggc acgaggtctt ctacgggatc atgtttgatg caggaagcac tggcacccga     420
gtacacgtct tccagttcac ccggcccccc agagaaactc ccacgttaac ccacgaaacc     480
ttcaaagcag tgaagccagg tctttctgcc tatgctgatg atgttgaaaa gagcgctcag     540
ggaatccggg aactactgga tgttgctaaa caggacattc cgttcgactt ctggaaggcc     600 accctctgg tcctcaaggc cacagctggc ttacgcctgt tacctggaga aaaggcccag     660
aagttactgc agaaggtgaa agaagtattt aaagcatcgc ctttccttgt aggggatgac     720
tgtgtttcca tcatgaacgg aacagatgaa ggcgtttcgg cgtggatcac catcaacttc     780
ctgacaggca gcttgaaaac tccaggaggg agcagcgtgg gcatgctgga cttgggcgga     840
ggatccactc agatcgcctt cctgccacgc gtggagggca ccctgcaggc ctccccaccc     900
ggctacctga cggcactgcg gatgtttaac aggacctaca agctctattc ctacagctac     960
ctcgggctcg ggctgatgtc ggcacgcctg gcgatcctgg gcggcgtgga ggggcagcct    1020
gctaaggatg gaaaggagtt ggtcagccct tgcttgtctc ccagtttcaa aggagagtgg    1080
gaacacgcag aagtcacgta cagggtttca gggcagaaag cagcggcaag cctgcacgag    1140
ctgtgtgctg ccagagtgtc agaggtcctt caaaacagag tgcacaggac ggaggaagtg    1200
aagcatgtgg acttctatgc tttctcctac tattacgacc ttgcagctgg tgtgggcctc    1260
atagatgcgg agaagggagg cagcctggtg gtgggggact cgagatcgc agccaagtac    1320 gtgtgtcgga ccctggagac acagccgcag agcagcccct tctcatgcat ggacctcacc    1380
tacgtcagcc tgctactcca ggagttcggc tttcccagga gcaaagtgct gaagctcact    1440
cggaaaattg acaatgttga gaccagctgg gctctggggg ccattttttca ttacatcgac    1500 tccctgaaca gacagaagag tccagcctca tagtggccga gccatccctg tccccgtcag    1560
cagtgtctgt gtgtctgcat aaaccctcct gtcctggacg tgacttcatc ctgaggagcc    1620
```

```
acagcacagg ccgtgctggc actttctgca cactggctct gggacttgca gaaggcctgg    1680
tgctgccctg gcatcagcct cttccagtca catctggcca gagggctgtc tggacctggg    1740
ccctgctcaa tgccacctgt ctgcctgggc tccaagtggg caggaccagg acagaaccac    1800
aggcacacac tgagggggca gtgtggctcc ctgcctgtcc catccccatg ccccgtccgc    1860
ggggctgtgg ctgctgctgt gcatgtccct gcgatggagt cttgtctcc cagcctgtca     1920 gtttcctccc cagggcagag ctccccttcc tgcaagagtc tgggaggcgg tgcaggctgt    1980
cctggctgct ctggggaagc cgagggacag ccataacacc cccgggacag taggtctggg    2040
cggcaccact gggaactctg gacttgagtg tgtttgctct tccttgggta tgaatgtgtg    2100
agttcaccca gaggcctgct ctcctcacac attgtgtggt ttggggttaa tgatggaggg    2160
agacacctct tcatagacgg caggtgccca cctttcaggg agtctcccag catgggcgga    2220
tgccgggcat gagctgctgt aaactatttg tggctgtgct gcttgagtga cgtctctgtc    2280
gtgtgggtgc caagtgcttg tgtagaaact gtgttctgag ccccttttc tggacaccaa     2340 ctgtgtcctg tgaatgtatc gctactgtga gctgttcccg cctagccagg gccatgtctt    2400
aggtgcagct gtgccacggg tcagctgagc cacagtccca gaaccaagct ctcggtgtct    2460
cgggccacca tccgcccacc tcgggctgac cccacctcct ccatggacag tgtgagcccc    2520
gggccgtgca tcctgctcag tgtggcgtca gtgtcggggc tgagccccctt gagctgcttc   2580 agtgaatgta cagtgcccgg cacgagctga acctcatgtg ttccactccc aataaaaggt    2640
tgacaggggc ttctccttca aaaaaaaaaa aaaaaaaaa aaaaaaaaa aaa              2693
```

<210> SEQ ID NO 49
<211> LENGTH: 2294
<212> TYPE: DNA
<213> ORGANISM: Homo sapiens

<400> SEQUENCE: 49

```
gtggggtcgt atcccgcggg tggaggccgg ggtggcgccg gccggggcgg gggagcccaa      60
aagaccggct gccgcctgct ccccggaaaa gggcactcgt ctccgtgggt gtggcggagc     120
gcgcggtgca tgagcgctca gggaatccgg gaactactgg atgttgctaa acaggacatt     180
ccgttcgact tctggaaggc caccccctctg gtcctcaagg ccacagctgg cttacgcctg    240
ttacctggag aaaaggccca gaagttactg cagaaggtga agaagtatt taaagcatcg      300 cctttccttg tagggatga ctgtgtttcc atcatgaacg gaacagatga aggcgtttcg       360
gcgtggatca ccatcaactt cctgacaggc agcttgaaaa ctccaggagg gagcagcgtg    420
ggcatgctgg acttgggcgg aggatccact cagatcgcct cctgccacg cgtggagggc      480 accctgcagg cctccccacc cggctacctg acggcactgc ggatgtttaa caggacctac    540
aagctctatt cctacagcta cctcgggctc gggctgatgt cggcacgcct ggcgatcctg    600
ggcggcgtgg aggggcagcc tgctaaggat ggaaaggagt tggtcagccc ttgcttgtct    660
cccagtttca aaggagagtg ggaacacgca gaagtcacgc acagggtttc agggcagaaa    720
gcagcggcaa gcctgcacga gctgtgtgct gccagagtgt cagaggtcct tcaaaacaga    780
gtgcacagga cggaggaagt gaagcatgtg gacttctatg cttctcctg ctattacgac     840 cttgcagctg gtgtgggcct catagatgcg gagaaggag gcagcctggt ggtggggggac   900 ttcgagatcg cagccaagta cgtgtgtcgg accctgagga cacagccgca gagcagcccc    960
ttctcatgca tggacctcac ctacgtcagc ctgctactcc aggagttcgg cttcccagg     1020
```

-continued

```
agcaaagtgc tgaagctcac tcggaaaatt gacaatgttg agaccagctg ggctctgggg      1080
gccatttttc attacatcga ctccctgaac agacagaaga gtccagcctc atagtggccg      1140
agccatccct gtccccgtca gcagtgtctg tgtgtctgca taaaccctcc tgtcctggac      1200
gtgacttcat cctgaggagc acagcacag gccgtgctgg cactttctgc acactggctc       1260
tgggacttgc agaaggcctg tgctgccct ggcatcagcc tcttccagtc acatctggcc       1320
agagggctgt ctggacctgg gccctgctca atgccacctg tctgcctggg ctccaagtgg      1380
gcaggaccag gacagaacca caggcacaca ctgaggggc agtgtggctc cctgcctgtc       1440 ccatcccat gccccgtccg cggggctgtg gctgctgctg tgcatgtccc tgcgatggga      1500
gtcttgtctc ccagcctgtc agtttcctcc caggg caga gctcccttc ctgcaagagt       1560 ctgggaggcg gtgcaggctg tcctggctgc tctggggaag ccagggaca gccataacac      1620 ccccgggaca gtaggtctgg gcggcaccac tgggaactct ggacttgagt gtgtttgctc      1680
ttccttgggt atgaatgtgt gagttcaccc agaggcctgc tctcctcaca cattgtgtgg     1740
tttggggtta atgatggagg gagacacctc ttcatagacg gcaggtgccc acctttcagg    1800
gagtctccca gcatgggcgg atgccgggca tgagctgctg taaactattt gtggctgtgc     1860
tgcttgagtg acgtctctgt cgtgtgggtg ccaagtgctt gtgtagaaac tgtgttctga    1920
gccccctttt ctggacacca actgtgtcct gtgaatgtat cgctactgtg agctgttccc     1980
gcctagccag ggccatgtct taggtgcagc tgtgccacgg gtcagctgag ccacagtccc    2040
agaaccaagc tctcggtgtc tcgggccacc atccgcccac ctcgggctga ccccacctcc    2100
tccatggaca gtgtgagccc cgggccgtgc atcctgctca gtgtggcgtc agtgtcgggg    2160
ctgagcccct tgagctgctt cagtgaatgt acagtgcccg gcacgagctg aacctcatgt   2220
gttccactcc caataaaagg ttgacagggg cttctccttc aaaaaaaaaa aaaaaaaaa     2280 aaaaaaaaaa aaaa                                                      2294
```

<210> SEQ ID NO 50
<211> LENGTH: 2805
<212> TYPE: DNA
<213> ORGANISM: Homo sapiens

<400> SEQUENCE: 50

```
gtggggtcgt atcccgcggg tggaggccgg ggtggcgccg gccggggcgg gggagcccaa        60
aagaccggct gccgcctgct ccccggaaaa gggcactcgt ctccgtgggt gtggcggagc       120
gcgcggtgca tggaatgggc tatgtgaatg aaaaaaggta tccgttatga aacttccaga       180
aaaacgagct acattttca gcagccgcag cacggtcctt ggcaaacaag gatgagaaaa       240
atatccaacc acgggagcct gcgggtggcg aaggtggcat acccctggg gctgtgtgtg       300 ggcgtgttca tctatgttgc ctacatcaag tggcaccggg ccaccgccac ccaggccttc      360
ttcagcatca ccagggcagc cccggggcc cgtgggtc agcaggccca cagccccctg         420
gggacagctg cagacgggca cgaggtcttc tacgggatca tgtttgatgc aggaagcact      480
ggcacccgag tacacgtctt ccagttcacc cggccccca gagaaactcc cacgttaacc       540
cacgaaacct tcaaagcagt gaagccaggt ctttctgcct atgctgatga tgttgaaaag      600
agcgctcagg gaatccggga actactggat gttgctaaac aggacattcc gttcgacttc      660
tggaaggcca cccctctggt cctcaaggcc acagctggct tacgcctgtt acctggagaa      720
aaggcccaga agttactgca gaaggtgaaa gaagtattta aagcatcgcc tttccttgta     780
ggggatgact gtgttccat catgaacgga acagatgaag gcgtttcggc gtggatcacc      840
```

-continued

| | |
|---|---|
| atcaacttcc tgacaggcag cttgaaaact ccaggaggga gcagcgtggg catgctggac | 900 |
| ttgggcggag gatccactca gatcgccttc ctgccacgcg tggagggcac cctgcaggcc | 960 |
| tccccacccg gctacctgac ggcactgcgg atgtttaaca ggacctacaa gctctattcc | 1020 |
| tacagctacc tcgggctcgg gctgatgtcg gcacgcctgg cgatcctggg cggcgtggag | 1080 |
| gggcagcctg ctaaggatgg aaaggagttg gtcagcccct tgcttgtctcc cagtttcaaa | 1140 |
| ggagagtggg aacacgcaga agtcacgtac agggtttcag ggcagaaagc agcggcaagc | 1200 |
| ctgcacgagc tgtgtgctgc cagagtgtca gaggtccttc aaaacagagt gcacaggacg | 1260 |
| gaggaagtga agcatgtgga cttctatgct ttctcctact attacgacct tgcagctggt | 1320 |
| gtgggcctca tagatgcgga aagggaggc agcctggtgg tgggggactt cgagatcgca | 1380 |
| gccaagtacg gtgggagtca cctggagcgt gaagggacgt gtctcatccc cagtgtgtcg | 1440 |
| gaccctggag acacagccgc agagcagccc cttctcatgc atggacctca cctacgtcag | 1500 |
| cctgctactc caggagttcg gctttcccag gagcaaagtg ctgaagctca ctcggaaaat | 1560 |
| tgacaatgtt gagaccagct gggctctggg gccattttt cattacatcg actccctgaa | 1620 |
| cagacagaag agtccagcct catagtggcc gagccatccc tgtccccgtc agcagtgtct | 1680 |
| gtgtgtctgc ataaaccctc ctgtcctgga cgtgacttca tcctgaggag ccacagcaca | 1740 |
| ggccgtgctg gcactttctg cacactggct ctgggacttg cagaaggcct ggtgctgccc | 1800 |
| tggcatcagc ctcttccagt cacatctggc cagagggctg tctggacctg ggccctgctc | 1860 |
| aatgccacct gtctgcctgg gctccaagtg ggcaggacca ggacagaacc acaggcacac | 1920 |
| actgagggg cagtgtggct ccctgcctgt cccatcccca tgccccgtcc gcggggctgt | 1980 |
| ggctgctgct gtgcatgtcc ctgcgatggg agtcttgtct cccagcctgt cagtttcctc | 2040 |
| cccagggcag agctcccctt cctgcaagag tctgggaggc ggtgcaggct gtcctggctg | 2100 |
| ctctggggaa gccgagggac agccataaca ccccgggac agtaggtctg ggcggcacca | 2160 |
| ctgggaactc tggacttgag tgtgtttgct cttccttggg tatgaatgtg tgagttcacc | 2220 |
| cagaggcctg ctctcctcac acattgtgtg gtttggggtt aatgatggag ggagacacct | 2280 |
| cttcatagac ggcaggtgcc cacctttcag ggagtctccc agcatgggcg gatgccgggc | 2340 |
| atgagctgct gtaaactatt tgtggctgtg ctgcttgagt gacgtctctg tcgtgtgggt | 2400 |
| gccaagtgct tgtgtagaaa ctgtgttctg agccccctt tctggacacc aactgtgtcc | 2460 |
| tgtgaatgta tcgctactgt gagctgttcc cgcctagcca gggccatgtc ttaggtgcag | 2520 |
| ctgtgccacg ggtcagctga gccacagtcc cagaaccaag ctctcggtgt ctcgggccac | 2580 |
| catccgccca cctcgggctg accccacctc ctccatggac agtgtgagcc ccgggccgtg | 2640 |
| catcctgctc agtgtggcgt cagtgtcggg gctgagcccc ttgagctgct tcagtgaatg | 2700 |
| tacagtgccc ggcacgagct gaacctcatg tgttccactc ccaataaaag gttgacaggg | 2760 |
| gcttctcctt caaaaaaaaa aaaaaaaaa aaaaaaaaa aaaaa | 2805 |

<210> SEQ ID NO 51
<211> LENGTH: 2497
<212> TYPE: DNA
<213> ORGANISM: Homo sapiens

<400> SEQUENCE: 51

| | |
|---|---|
| tgctgccttc ctgtccaggc tccattaggg ctccctggat gtctgggctc cgctgaccgg | 60 |
| tggggggcaa gtccagtgtt ttgggccaca gggcgggcca aatagcaggg gcctgtagcc | 120 |

-continued

| | |
|---|---|
| ccaggggggcc ccagccctgc tgcgttcatt cattcagccc gcttttgcgg acccgccccc | 180 |
| agtctgcgtc agggacagac ccctccgccc tggatgagcc cggcggggaa gcttcgcgta | 240 |
| gcagtttctg ggaaacagaa actcccacgt taacccacga aaccttcaaa gcagtgaagc | 300 |
| caggtctttc tgcctatgct gatgatgttg aaaagagcgc tcagggaatc cgggaactac | 360 |
| tggatgttgc taaacaggac attccgttcg acttctggaa ggccaccct ctggtcctca | 420 |
| aggccacagc tggcttacgc ctgttacctg agaaaaggc ccagaagtta ctgcagaagg | 480 |
| tgaaagaagt atttaaagca tcgccttttcc ttgtaggga tgactgtgtt tccatcatga | 540 |
| acggaacaga tgaaggcgtt tcggcgtgga tcaccatcaa cttcctgaca ggcagcttga | 600 |
| aaactccagg agggagcagc gtgggcatgc tggacttggg cggaggatcc actcagatcg | 660 |
| ccttcctgcc acgcgtggag ggcaccctgc aggcctcccc acccggctac ctgacggcac | 720 |
| tgcggatgtt taacaggacc tacaagctct attcctacag ctacctcggg ctcgggctga | 780 |
| tgtcggcacg cctggcgatc ctgggcggcg tggaggggca gcctgctaag gatggaaagg | 840 |
| agttggtcag cccttgcttg tctcccagtt caaaggaga gtgggaacac gcagaagtca | 900 |
| cgtacagggt ttcagggcag aaagcagcgg caagcctgca cgagctgtgt gctgccagag | 960 |
| tgtcagaggt ccttcaaaac agagtgcaca ggacggagga agtgaagcat gtggacttct | 1020 |
| atgctttctc ctactattac gaccttgcag ctggtgtggg cctcatagat gcggagaagg | 1080 |
| gaggcagcct ggtggtgggg gacttcgaga tcgcagccaa gtacgtgtgt cggaccctgg | 1140 |
| agacacagcc gcagagcagc cccttctcat gcatggacct cacctacgtc agcctgctac | 1200 |
| tccaggagtt cggctttccc aggagcaaag tgctgaagct cactcggaaa attgacaatg | 1260 |
| ttgagaccag ctgggctctg ggggccattt ttcattacat cgactccctg aacagacaga | 1320 |
| agagtccagc ctcatagtgg ccgagccatc cctgtccccg tcagcagtgt ctgtgtgtct | 1380 |
| gcataaaccc tcctgtcctg gacgtgactt catcctgagg agccacagca caggccgtgc | 1440 |
| tggcactttc tgcacactgg ctctgggact tgcagaaggc ctggtgctgc cctggcatca | 1500 |
| gcctcttcca gtcacatctg gccagagggc tgtctggacc tgggccctgc tcaatgccac | 1560 |
| ctgtctgcct gggctccaag tgggcaggac caggacagaa ccacaggcac acactgaggg | 1620 |
| ggcagtgtgg ctccctgcct gtcccatccc catgccccgt ccgcggggct gtggctgctg | 1680 |
| ctgtgcatgt ccctgcgatg ggagtcttgt ctcccagcct gtcagtttcc tccccagggc | 1740 |
| agagctcccc ttcctgcaag agtctgggag gcggtgcagg ctgtcctggc tgctctgggg | 1800 |
| aagccgaggg acagccataa cacccccggg acagtaggtc tgggcggcac cactgggaac | 1860 |
| tctggacttg agtgtgtttg ctcttccttg ggtatgaatg tgtgagttca cccagaggcc | 1920 |
| tgctctcctc acacattgtg tggtttgggg ttaatgatgg agggagacac ctcttcatag | 1980 |
| acggcaggtg cccaccttc agggagtctc ccagcatggg cggatgccgg gcatgagctg | 2040 |
| ctgtaaacta tttgtggctg tgctgcttga gtgacgtctc tgtcgtgtgg gtgccaagtg | 2100 |
| cttgtgtaga aactgtgttc tgagcccct tttctggaca ccaactgtgt cctgtgaatg | 2160 |
| tatcgctact gtgagctgtt cccgcctagc cagggccatg tcttaggtgc agctgtgcca | 2220 |
| cgggtcagct gagccacagt cccagaacca agctctcggt gtctcgggcc accatccgcc | 2280 |
| cacctcgggc tgacccacc tcctccatgg acagtgtgag ccccggggccg tgcatcctgc | 2340 |
| tcagtgtggc gtcagtgtcg gggctgagcc ccttgagctg cttcagtgaa tgtacagtgc | 2400 |
| ccggcacgag ctgaacctca tgtgttccac tcccaataaa aggttgacag gggcttctcc | 2460 |
| ttcaaaaaaa aaaaaaaaaa aaaaaaaaaa aaaaaaa | 2497 |

<210> SEQ ID NO 52
<211> LENGTH: 2762
<212> TYPE: DNA
<213> ORGANISM: Homo sapiens

<400> SEQUENCE: 52

| | | | | | |
|---|---|---|---|---|---|
| gtgggtcgt | atcccgcggg | tggaggccgg | ggtggcgccg | gccggggcgg | gggagcccaa | 60 |
| aagaccggct | gccgcctgct | ccccggaaaa | gggcactcgt | ctccgtgggt | gtggcggagc | 120 |
| gcgcggtgca | tggaatgggc | tatgtgaatg | aaaaaaggta | tccgttatga | aacttccaga | 180 |
| aaaacgagct | acatttttca | gcagccgcag | cacggtcctt | ggcaaacaag | gatgagaaaa | 240 |
| atatccaacc | acgggagcct | gcgggtggcg | aaggtggcat | accccctggg | gctgtgtgtg | 300 |
| ggcgtgttca | tctatgttgc | ctacatcaag | tggcaccggg | ccaccgccac | ccaggccttc | 360 |
| ttcagcatca | ccagggcagc | cccggggggcc | cggtggggtc | agcaggccca | cagccccctg | 420 |
| gggacagctg | cagacgggca | cgaggtcttc | tacgggatca | tgtttgatgc | aggaagcact | 480 |
| ggcacccgag | tacgtgtctt | ccagttcacc | cggcccccca | gagaaactcc | cacgttaacc | 540 |
| cacgaaacct | tcaaagcagt | gaagccaggt | ctttctgcct | atgctgatga | tgttgaaaag | 600 |
| agcgctcagg | gaatccggga | actactggat | gttgctaaac | aggacattcc | gttcgacttc | 660 |
| tggaaggcca | cccctctggt | cctcaaggcc | acagctggct | tacgcctgtt | acctggagaa | 720 |
| aaggcccaga | agttactgca | gaaggtgaaa | gaagtattta | agcatcgcc | tttccttgta | 780 |
| ggggatgact | gtgtttccat | catgaacgga | acagatgaag | gcgtttcggc | gtggatcacc | 840 |
| atcaacttcc | tgacaggcag | cttgaaaact | ccaggaggga | gcagcgtggg | catgctggac | 900 |
| ttgggcggag | gatccactca | gatcgccttc | ctgccacgcg | tggagggcac | cctgcaggcc | 960 |
| tccccacccg | gctacctgac | ggcactgcgg | atgtttaaca | ggacctacaa | gctctattcc | 1020 |
| tacagctacc | tcgggctcgg | gctgatgtcg | gcacgcctgg | cgatcctggg | cggcgtggag | 1080 |
| gggcagcctg | ctaaggatgg | aaaggagttg | gtcagccctt | gcttgtctcc | cagtttcaaa | 1140 |
| ggagagtggg | aacacgcaga | agtcacgtac | agggtttcag | ggcagaaagc | agcggcaagc | 1200 |
| ctgcacgagc | tgtgtgctgc | cagagtgtca | gaggtccttc | aaaacagagt | gcacaggacg | 1260 |
| gaggaagtga | agcatgtgga | cttctatgct | ttctcctact | attacgacct | tgcagctggt | 1320 |
| gtgggcctca | tagatgcgga | gaagggaggc | agcctggtgg | tgggggactt | cgagatcgca | 1380 |
| gccaagtacg | tgtgtcggac | cctggagaca | cagccgcaga | gcagcccctt | ctcatgcatg | 1440 |
| gacctcacct | acgtcagcct | gctactccag | gagttcggct | ttcccaggag | caaagtgctg | 1500 |
| aagctcactc | ggaaaattga | caatgttgag | accagctggg | ctctgggggc | catttttcat | 1560 |
| tacatcgact | ccctgaacag | acagaagagt | ccagcctcat | agtggccgag | ccatccctgt | 1620 |
| ccccgtcagc | agtgtctgtg | tgtctgcata | aaccctcctg | tcctggacgt | gacttcatcc | 1680 |
| tgaggagcca | cagcacaggc | cgtgctggca | cttttctgcac | actggctctg | ggacttgcag | 1740 |
| aaggcctggt | gctgccctgg | catcagcctc | ttccagtcac | atctgccag | agggctgtct | 1800 |
| ggacctgggc | cctgctcaat | gccacctgtc | tgcctgggct | ccaagtgggc | aggaccagga | 1860 |
| cagaaccaca | ggcacacact | gaggggggcag | tgtggctccc | tgcctgtccc | atccccatgc | 1920 |
| cccgtccgcg | gggctgtggc | tgctgctgtg | catgtccctg | cgatgggagt | cttgtctccc | 1980 |
| agcctgtcag | tttcctcccc | aggcagagc | tcccctttcct | gcaagagtct | gggaggcggt | 2040 |
| gcaggctgtc | ctggctgctc | tggggaagcc | gagggacagc | cataacaccc | ccgggacagt | 2100 |

-continued

| | |
|---|---|
| aggtctgggc ggcaccactg ggaactctgg acttgagtgt gttgctctt ccttgggtat | 2160 |
| gaatgtgtga gttcacccag aggcctgctc tcctcacaca ttgtgtggtt tggggttaat | 2220 |
| gatggaggga gacacctctt catagacggc aagtgcccac ctttcaggga gtctcccagc | 2280 |
| atgggcggat gccgggcatg agctgctgta aactatttgt ggctgtgctg cttgagtgac | 2340 |
| gtctctgtcg tgtgggtgcc aagtgcttgt gtagaaactg tgttctgagc ccccttttct | 2400 |
| ggacaccaac tgtgtcctgt gaatgtatcg ctactgtgag ctgttccgc ctagccaggg | 2460 |
| ccatgtctta ggtgcagctg tgccacgggt cagctgagcc acagtcccag aaccaagctc | 2520 |
| tcggtgtctc gggccaccat ccgcccacct cgggctgacc ccacctcctc catggacagt | 2580 |
| gtgagccccg ggccgtgcat cctgctcagt gtggcgtcag tgtcgggct gagccccttg | 2640 |
| agctgcttca gtgaatgtac agtgcccggc acgagctgaa cctcatgtgt tccactccca | 2700 |
| ataaaaggtt gacaggggct tctccttcaa aaaaaaaaa aaaaaaaaa aaaaaaaaa | 2760 |
| aa | 2762 |

<210> SEQ ID NO 53
<211> LENGTH: 1588
<212> TYPE: DNA
<213> ORGANISM: Homo sapiens

<400> SEQUENCE: 53

| | |
|---|---|
| gtggggtcgt atcccgcggg tggaggccgg ggtggcgccg gccggggcgg gggagcccaa | 60 |
| aagaccggct gccgcctgct ccccggaaaa gggcactcgt ctccgtgggt gtggcggagc | 120 |
| gcgcggtgca tggaatgggc tatgtgaatg aaaaaaggta ccgttatga aacttccaga | 180 |
| aaaacgagct acattttca gcagccgcag cacggtcctt ggcaaacaag gatgagaaaa | 240 |
| atatccaacc acgggagcct gcgggtggcg aaggtggcat accccctggg gctgtgtgtg | 300 |
| ggcgtgttca tctatgttgc ctacatcaag tggcaccggg ccaccgccac ccaggccttc | 360 |
| ttcagcatca ccagggcagc cccggggcc cggtgggtc agcaggccca cagcccctg | 420 |
| gggacagctg cagacgggca cgaggtcttc tacgggatca tgttttgatgc aggaagcact | 480 |
| ggcacccgag tacacgtctt ccagttcacc cggccccca gagaaactcc cacgttaacc | 540 |
| cacgaaacct tcaaagcagt gaagccaggt ctttctgcct atgctgatga tgttgaaaag | 600 |
| agcgctcagg gaatccggga actactggat gttgctaaac aggacattcc gttcgacttc | 660 |
| tggaaggcca cccctctggt cctcaaggcc acagctggct tacgcctgtt acctggagaa | 720 |
| aaggcccaga agttactgca aaggtgaaa gaagtattta agcatcgcc tttccttgta | 780 |
| ggggatgact gtgtttccat catgaacgga acagatgaag gcgtttcggc gtggatcacc | 840 |
| atcaacttcc tgacaggcag cttgaaaact ccaggaggga gcagcgtggg catgctggac | 900 |
| ttgggcggag gatccactca gatcgccttc ctgccacgcg tggagggcac cctgcaggcc | 960 |
| tccccacccg gctacctgac ggcactgcgg atgtttaaca ggacctacaa gctctattcc | 1020 |
| tacagctacc tcgggctcgg gctgatgtcg gcacgcctgg cgatcctggg cggcgtggag | 1080 |
| ggcagcctg ctaaggatgg aaaggagttg gtcagccctt gcttgtctcc cagtttcaaa | 1140 |
| ggagagtggg aacacgcaga agtcacgtac agggtttcag gcagaaagc agcggcaagc | 1200 |
| ctgcacgagc tgtgtgctgc cagagtgtca gaggtccttc aaaacagagt gcacaggacg | 1260 |
| gaggaagtga agcatgtgga cttctatgct ttctccctact attacgacct tgcagctggt | 1320 |
| gtgggcctca tagatgcgga aagggaggc agcctggtgg tgggggactt cgagatcgca | 1380 |
| gccaagtacg aaagcttagg ttttatgcag cttgacacct gggagaggtg tccagggtct | 1440 |

-continued

| | |
|---|---|
| tagatgtaga aatgtggctt gggagacatt ggcccatgac cctaacacca ggcgtgcaaa | 1500 |
| tcccccttgga gcccagaccc agtggcagcc ggggttgccg cccacctgcc tgtgctgtgc | 1560 |
| actgggtgcc ttctgcgctc agctgcgg | 1588 |

<210> SEQ ID NO 54
<211> LENGTH: 2882
<212> TYPE: DNA
<213> ORGANISM: Homo sapiens

<400> SEQUENCE: 54

| | |
|---|---|
| gtggggtcgt atcccgcggg tggaggccgg ggtggcgccg gccggggcgg gggagcccaa | 60 |
| aagaccggct gccgcctgct ccccggaaaa gggcactcgt ctccgtgggt gtggcggagc | 120 |
| gcgcggtgca tggaatgggc tatgtgaatg aaaaaaggta tccgttatga aacttccaga | 180 |
| aaaacgagct acattttca gcagccgcag cacggtcctt ggcaaacaag gatgagaaaa | 240 |
| atatccaacc acgggagcct gcgggtggcg aaggtggcat accccctggg gctgtgtgtg | 300 |
| ggcgtgttca tctatgttgc ctacatcaag tggcaccggg ccaccgccac ccaggccttc | 360 |
| ttcagcatca ccagggcagc cccgggggcc cggtggggtc agcaggccca cagccccctg | 420 |
| gggacagctg cagacgggca cgaggtcttc tacgggatca tgtttgatgc aggaagcact | 480 |
| ggcacccgag tacacgtctt ccagttcacc cggcccccca gagaaactcc cacgttaacc | 540 |
| cacgaaacct tcaaagcagt gaagccaggt ctttctgcct atgctgatga tgttgaaaag | 600 |
| agcgctcagg gaatccggga actactggat gttgctaaac aggacattcc gttcgacttc | 660 |
| tggaaggcca cccctctggt cctcaaggcc acagctggct tacgcctgtt acctggagaa | 720 |
| aaggcccaga agttactgca gaaggtgaaa gaagtattta agcatcgcc tttccttgta | 780 |
| ggggatgact gtgtttccat catgaacgga acagatgaag gcgtttcggc gtggatcacc | 840 |
| atcaacttcc tgacaggcag cttgaaaact ccaggaggga gcagcgtggg catgctggac | 900 |
| ttgggcggag gatccactca gatcgccttc ctgccacgcg tggagggcac cctgcaggcc | 960 |
| tccccacccg gctacctgac ggcactgcgg atgtttaaca ggacctacaa gctctattcc | 1020 |
| tacagctacc tcgggctcgg gctgatgtcg gcacgcctgg cgatcctggg cggcgtggag | 1080 |
| gggcagcctg ctaaggatgg aaaggagttg gtcagcccctt gcttgtctcc cagtttcaaa | 1140 |
| ggagagtggg aacacgcaga agtcacgtac agggtttcag ggcagaaagc agcggcaagc | 1200 |
| ctgcacgagc tgtgtgctgc cagagtgtca gaggtccttc aaaacagagt gcacaggacg | 1260 |
| gaggaagtga agcatgtgga cttctatgct ttctcctact attacgacct tgcagctggt | 1320 |
| gtgggcctca taggaggcca gaagcagatt tgagaaggcg tctcatcctg agtaggaaaa | 1380 |
| gatcagttct ttgagccctt cagtaaaacc tcgtggctgg tgacttgctg ttgattccag | 1440 |
| ttcctgctgg aagatgcgga gaagggaggc agcctggtgg tgggggactt cgagatcgca | 1500 |
| gccaagtacg tgtgtcggac cctggagaca cagccgcaga gcagcccctt ctcatgcatg | 1560 |
| gacctcacct acgtcagcct gctactccag gagttcggct ttcccaggag caaagtgctg | 1620 |
| aagctcactc ggaaaattga caatgttgag accagctggg ctctgggggc cattttcat | 1680 |
| tacatcgact ccctgaacag acagaagagt ccagcctcat agtggccgag ccatccctgt | 1740 |
| ccccgtcagc agtgtctgtg tgtctgcata aaccctcctg tcctggacgt gacttcatcc | 1800 |
| tgaggagcca cagcacaggc cgtgctggca ctttctgcac actggctctg ggacttgcag | 1860 |
| aaggcctggt gctgccctgg catcagcctc ttccagtcac atctggccag agggctgtct | 1920 |

```
                                                        -continued ggacctgggc cctgctcaat gccacctgtc tgcctgggct ccaagtgggc aggaccagga     1980
cagaaccaca ggcacacact gaggggggcag tgtggctccc tgcctgtccc atccccatgc   2040
cccgtccgcg gggctgtggc tgctgctgtg catgtccctg cgatgggagt cttgtctccc    2100
agcctgtcag tttcctcccc agggcagagc tccccttcct gcaagagtct gggaggcggt   2160
gcaggctgtc ctggctgctc tggggaagcc gagggacagc cataacaccc ccgggacagt    2220
aggtctgggc ggcaccactg ggaactctgg acttgagtgt gtttgctctt ccttgggtat    2280
gaatgtgtga gttcacccag aggcctgctc tcctcacaca ttgtgtggtt tggggttaat    2340
gatggaggga gacacctctt catagacggc aggtgcccac ctttcaggga gtctcccagc    2400
atgggcggat gccgggcatg agctgctgta aactatttgt ggctgtgctg cttgagtgac    2460
gtctctgtcg tgtgggtgcc aagtgcttgt gtagaaactg tgttctgagc ccccttttct    2520
ggacaccaac tgtgtcctgt gaatgtatcg ctactgtgag ctgttcccgc ctagccaggg    2580
ccatgtctta ggtgcagctg tgccacgggt cagctgagcc acagtcccag aaccaagctc    2640
tcggtgtctc gggccaccat ccgcccacct cgggctgacc ccacctcctc catggacagt    2700
gtgagccccg ggccgtgcat cctgctcagt gtggcgtcag tgtcggggct gagccccttg    2760
agctgcttca gtgaatgtac agtgcccggc acgagctgaa cctcatgtgt tccactccca    2820
ataaaaggtt gacagggct tctccttcaa aaaaaaaaa aaaaaaaaa aaaaaaaaa        2880 aa                                                                   2882
```

METHODS AND MATERIALS RELATING TO CD39-LIKE POLYPEPTIDES

1. RELATED APPLICATIONS

This patent application is a continuation-in-part of U.S. patent application Ser. No. 09/481,238 filed Jan. 11, 2000, now abandoned, which is a continuation-in-part of U.S. patent application Ser. No. 09/370,265 filed Aug. 9, 1999 which is a continuation-in-part of PCT patent application Serial No. PCT/US99/16180 filed Jul. 16, 1999 which is a continuation-in-part of U.S. patent application Ser. No. 09/350836 filed Jul. 9, 1999 which is a continuation-in-part of U.S. patent application Ser. No. 09/273,447 filed Mar. 19, 1999, now abandoned, which is a continuation-in-part of U.S. patent application Ser. No. 09/122,449 filed Jul. 24, 1998, now abandoned, and also a continuation-in-part of U.S. patent application Ser. No. 09/244,444 filed Feb. 4, 1999, now abandoned, which in turn is a continuation of U.S. patent application Ser. No. 09/118,205 filed Jul. 16, 1998, now abandoned, the disclosures of all of which are incorporated by reference herein in their entirety.

2. FIELD OF THE INVENTION

This invention relates in general to novel polynucleotides isolated from cDNA libraries of human fetal liver-spleen and macrophages and to polypeptides encoded by these polynucleotides. In particular, the invention relates to a human CD39-like protein with homologies to ATP diphosphohydrolases and variants thereof.

3. BACKGROUND

CD39 (cluster of differentiation 39) is a cell-surface molecule recognized by a "cluster" of monoclonal antibodies that can be used to identify the lineage or stage of differentiation of lymphocytes and thus to distinguish one class of lymphocytes from another. This CD39 molecule was originally defined as a B lymphocyte marker (Rowe, M., et al. Int. J. Cancer 29:373 (1982)). Subsequent studies have shown CD39 to be a marker for a distinct subset of activated lymphocytes within the allosensitized CD8-positive cytotoxic cells (Gouttefangeas C., et al., Eur. J. Immunol. 22:2681 (1992)). Outside of lymphoid tissue, CD39 can be found in quiescent vascular endothelial cells (Kansas, G. S., et al., J. Immunol. 146:2235 (1991)) and throughout rat brain in the neurons of the cerebral cortex, hippocampus, and cerebellum, as well as in glial cells (Wang, T -F. and Guidotti, G., Brain Res. 790:318 (1998)).

CD39 is a 510-amimio acid protein with a predicted molecular mass of 57 kDa. However, because of heavy glycosylation at asparagine residues (six potential N-glycosylation sites) the molecule displays a mobility closer to 100 kDa (Maliszewski, C. R., et al., J. Immunol. 153:3574 (1994)). CD39 contains two hydrophobic regions, one near the amino terminus and the other near the carboxyl terminus which are believed to be transmembrane regions.

The role of CD39 in platelet aggregation and ATP/ADP hydrolysis is unclear. Although CD39 was originally reported to be an ectoADPase with a preference for ATP over ADP as a substrate, Wang, et al., *J. Biol. Chem.* 271:9898–9901(1996), Marcus, et al., *J. Clin. Invest.* 99:1351–1360 (1997) reported that CD39 was unique for its high preference for ADP over ATP as a substrate and in 1998, Gayle, et al., *J. Clin Invest.* 10:1851–1859 (1998), described CD39 as an ecto ADPase with no preference for one substrate over the other.

Reports that several ATP Diphosphohydrolases (ATPDases) share amino acid sequence homology with CD39 have been substantiated by the showing that CD39 is itself an ATPDase (Wang, T- F., et al., J. Biol. Chem. 271:9898 (1996); Kaczmarek, E., et al., J. Biol. Chem. 271:33116 (1996)). Since CD39 is a plasma membrane-bound enzyme, CD39 has been termed an "ecto-ATPase," but CD39 is more often referred to as an "ecto-apyrase" because of the reduced rate of hydrolysis of ADP when compared with ecto-ATPases.

This activity has shown to modulate platelet reactivity and aggregation in response to vascular injury. During vascular injury, activated platelets aggregate forming an occlusive thrombus. Excessive platelet accumulation at sites of vascular injury can contribute to vessel occlusion. Endothelial cells respond to the potentially occlusive effects of platelet aggregation by several mechanisms. One of these mechanisms results ecto-apyrase-mediated removal of ADP, which in turn eliminates platelet reactivity and recruitment. It is now known that the endothelial ecto-apyrase responsible for this ADP removal is CD39 (Marcus, A. J., et al., J. Clin. Invest. 99:1 351 (1997)).

Recently, CD39 was engineered to produce a soluble form of the molecule. This soluble CD39 was shown to display the same nucleotidase activity as the membrane-bound molecule (Gayle, R. B., et al., J. Clin. Invest. 101:1851 (1998)). Intravenously administered soluble CD39 also remained active in mice for an extensive period of time, indicating that soluble CD39 could be useful as a inhibitor of platelet aggregation in the prophylaxis or treatment of platelet-mediated thrombotic conditions.

Platelet aggregation inhibitors (antithrombotic agents) decrease the formation or the action of chemical signals that promote platelet aggregation. Currently available antithrombotic agents include aspirin, ticlopidine, and dipyridamole. These agents have proven beneficial in the prevention and treatment of occlusive cardiovascular diseases, including myocardial infarction, cerebral ischemia, angina. Antithrombotic therapy has also been used in the maintenance of vascular grafts.

Myocardial infarction is the development of necrosis of the myocardium (the middle muscular layer of the heart wall) due to a critical imbalance between oxygen and myocardial demand. The most common cause of acute myocardium infarction is narrowing of the epicardial blood vessels due to atheromatous plaques. Plaque rupture with subsequent exposure of basement membrane results in platelet aggregation and thrombus formation, which can result in partial or complete occlusion of the vessel and subsequent myocardial ischemia.

In cerebral ischemia, inadequate blood flow results from an occlusion in a blood vessel or hemorrhaging. In the latter case, excessive bleeding in one area of the brain deprives another area of blood. If the damage occurs in a singular small area, "transient" or "focused" cerebral ischemia results. When a major artery is blocked (carotid artery) global or diffused ischemia results. The primary medical strategy for secondary prevention of stroke is antiplatelet therapy. Aspirin is currently employed for reducing the risk of recurrent transient ischemic attacks or stroke in men who have transient ischemia of the brain due to fibrin emboli.

Each year, thousands of patients suffer a decline in blood flow to one or more limbs. Without sufficient blood flow, and, unless blood flow can be restored in time, the limb must be amputated. In some cases, grafts from the patient's veins can be used to form new arteries. However, in cases where the quality of the veins is poor, polymeric vascular grafts are typically used. The polymeric grafts are inherently thrombogenic as the blood constituents passing through the grafts become activated and tend to form clots. Efforts to line the grafts with endothelial cells can reduce blood clotting, but better results are obtained when antithrombotic therapy is employed.

Angina pectoris is a characteristic chest pain caused by inadequate blood flow through the blood vessels of the myocardium. The imbalance between oxygen delivery and utilization may result from a spasm of the vascular smooth muscle or from obstruction of blood vessels caused by atherosclerotic lesions. Three classes of drugs have been shown to be effective in treating angina: nitrates, beta-blockers and calcium channel blockers. Currently, the antithrombotics dipyridamole and aspirin are employed to prophylactically treat angina pectoris.

Ecto-apyrases, such as CD39, offer a number of advantages over several of the standard antithrombotics. For example, aspirin treatment controls the prothrombotic action of thromboxane; however, aspirin also prevents formation of antithrombotic prostacyclin, which limits aspirin's efficacy. Another antithrombotic, endothelium-derived relaxing factor (nitric oxide; "EDRF/NO"), is inhibited in vitro and in vivo by hemoglobin after its rapid diffusion into erythrocytes. In contrast, CD39 is aspirin-insensitive and completely inhibits platelet reactivity even when eicosanoid and EDRF/NO production are blocked.

CD39's ATPDase activity also implicates CD39 in the modulation of neurotransmission. ATP is a major purinergic neurotransmitter that is often co-released into the synaptic cleft with several neurotransmitters. Responses to ATP are mediated by specific plasma membrane receptors, called P2 purinergic receptors (Dubyak, G. R. and El-Motassim, C. Am J. Physiol. 34:C577–C606 (1993)). The distribution of CD39 in the rat brain indicates that CD39 plays a role in terminating P2 purinergic neurotransmission (Wang, T. F. and Guidotti, G., Brain Res. 790:318 (1998)). Furthermore, a decrease in ecto-apyrase activity is believed to lead to an accumulation of the excitatory neurotransmitter, extracellular ATP, as well as a deficiency of the endogenous anticonvulsant extracellular adenosine.

The chomosomal localization of CD39 provides additional support for a role in modulation of neurotransmission. More specifically, CD39 has been mapped to chromosome 10q 23.1–24.1 (Maliszewski, C. R., et al., J. Immunol. 153:3574 (1994)), and this site overlaps with the susceptibility locus for human partial epilepsy with audiogenic symptoms (Ottman, R. et al., Nature Genet. 10:56 (1995)). This co-localization of the CD39 gene and the susceptibility locus has led to the hypothesis that decrease in ecto-apyrase activity in the brain is the primary cause of partial epilepsy (Wang T -F., et al., Mol. Brain Res. 47:295 (1997)).

A screen for human cDNAs that hybridize to cosmids from the human chromosome 9q34 region lead to the identification of a transcript with high homology to a chicken muscle ecto-ATPase (60% identity) and the ecto-apyrase CD39 (41% amino acid identity) (Chadwick, B. P., Mamm. Genome 8:668 (1997)). This gene, designated "CD39-like-1 gene" (CD39L1), has a higher degree of homology to CD39 than does chicken muscle ecto-ATPase. The biological activity of this protein has not been tested but on the basis of the high amino acid homology, CD39L1 is believed to be a new member of the ecto-ATPase family. Recently, a mouse gene with homology to NTPases was cloned and sequenced (Acc. No. AF006482) by Chadwick et al. (Mamm. Gen. 9:162–164 (1998).)

4. SUMMARY OF THE INVENTION

The invention is based on polynucleotides isolated from cDNA libraries prepared from human fetal liver-spleen and macrophages. The compositions of the present invention include novel isolated polypeptides with apyrase and/or NDPase activity, in particular, novel human CD39-like polypeptides, and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies.

The compositions of the invention additionally include vectors, including expression vectors, containing the polynucleotides of the invention, cells genetically engineered to contain such polynucleotides and cells genetically engineered to express such polynucleotides.

The isolated polynucleotides of the invention include naturally occurring or wholly or partially synthetic DNA, e.g., cDNA and genomic DNA, and RNA, e.g., mRNA. One polynucleotide according to the invention encodes a novel CD39-like protein having the amino acid sequence shown in FIG. 2 (SEQ ID NO. 3), which has been designated CD39-L4. Another polynucleotide according to the invention encodes a novel CD39-like protein having the amino acid sequence shown in SEQ ID NO: 27, which has been designated CD39-L2. In another embodiment, a polynucleotide according to the invention encodes a novel CD39-like protein having the full length or mature amino acid sequence set forth in SEQ ID NO. 25, which has been designated CD39-L66, and is an isoform of CD39-L4. The isolated polynucleotides of the invention include a polynucleotide comprising the nucleotide sequence of SEQ ID NO. 2, 24 or 26. The polynucleotides of the invention also include polynucleotides that encode polypeptides with a biological activity of the polypeptide of SEQ ID NO. 3 or 27 (including apyrase or NDPase activity) such as (a) the nucleotide sequence of SEQ ID NO. 2, 24, 26 or (b) a nucleotide sequence encoding the full length or mature amino acid sequence of SEQ ID NO. 3, 25, or 27; (c) a polynucleotide which is an allelic variant of any polynucleotide recited above; (d) a polynucleotide that hybridizes under stringent conditions to (a) or (b); (e) or a polynucleotide that encodes a polypeptide comprising at least one CD39-like domain, e.g. catalytic domain.

The polynucleotides of the invention additionally include the complement of any of the polynucleotides recited above.

A collection as used in this application can be a collection of only one polynucleotide. The collection of sequence information or identifying information of each sequence can be provided on a nucleic acid array. In one embodiment, segments of sequence information are provided on a nucleic acid array to detect the polynucleotide that contains the segment. The array can be designed to detect nucleic acids that are perfectly complementary (full-match) or mismatched to the polynucleotide that contains the segment. The collection can also be provided in a computer-readable format.

The invention also provides a polynucleotide including a nucleotide sequence that is substantially equivalent to these polynucleotides. Polynucleotides according to the invention can have at least about 80%, more typically at least about 90%, and even more typically at least about 95%, sequence identity to a polynucleotide of SEQ ID NO. 2, 24 or 26 and specifically include a human polynucleotide which has at least 80% sequence identity to a polynucleotide of SEQ ID NO. 2, 24 or 26; or a polynucleotide which has at least 90% sequence identity to a polynucleotide of SEQ ID NO. 2, 24 or 26. Similarly, polypeptides of the invention include polypeptides having apyrase or NDPase activity and at least about 80%, 90% or 95% sequence identity to SEQ ID NO. 3, 25 or 27. Polypeptides of the invention further include multimeric, especially dimeric, polypeptides having apyrase or NDPase activity and at least about 80%, 90% or 95% sequence identity to SEQ ID NO. 3, 25or 27.

A further aspect of the invention is the development of novel CD39-L4 polynucleotide or polypeptide variants which preferably exhibit increased recombinant expression levels or improved ADPase or NDPase activity compared to wild type CD39-L4 (SEQ ID NO: 5). This aspect of the invention includes polypeptides comprising at least one amino acid substitution selected from the group consisting of: D168→T, S170→Q and L175→F, wherein said substitution(s) result in increased ADPase activity of the polypeptide. One preferred embodiment is the polypeptide having the amino acid sequence set forth in SEQ ID NO: 7 (encoded by the nucleotide sequence of SEQ ID NO. 6), which is a variant CD39-L4 containing all three substitutions that has been designated ACRIII. A plasmid containing this DNA was deposited with the American Type Culture Collection (ATCC), 10801 University Avenue, Manassas, Va., on Jul. 13, 1999 under the terms of the Budapest Treaty (ATCC accession number PTA-346). Alternatively, instead of making the specific D168→T, S170→Q and/or L175→F substitution(s), substitution of amino acids with similar properties is contemplated. Additional conservative substitutions at amino acid positions other than D168, S170 and/or L175 are further contemplated. For example, all of the corresponding amino acids from CD39 could be substituted for amino acids 167–181 of CD39-L66 or CD39-L4.

This aspect of the invention also specifically contemplates that, in view of the fact that variant polynucleotides containing changes in the codons for amino acid 168, 170 and 175 are more highly expressed, such polynucleotides may be more highly expressed if the codons at these same positions are modified without changing the wild type amino acid sequence (e.g., polynucleotides having codon substitutions at or around nucleotide positions 747–749, 753–755, and/or 768–770 of SEQ ID NO: 2, or positions 502–504, 508–510 and/or 523–525 of SEQ ID NO: 4, or corresponding nucleotide positions in SEQ ID NO: 24 are contemplated).

In addition, development of novel CD39-L2 polynucleotide or polypeptide variants which preferably exhibit increased recombinant expression levels or improved ADPase or NDPase activity compared to wild type CD39-L2 (SEQ ID NO: 27) is also contemplated. This aspect of the invention includes polypeptides comprising at least one amino acid substitution wherein said substitution(s) result in increased recombinant expression levels or increased ADPase activity of the polypeptide, as well as polynucleotides encoding the wild type CD39-L2 sequence that have silent codon substitutions at nucleotide positions 806–808, 812–814 and/or 827–829 corresponding to those identified above for CD39-L4.

Polynucleotides encoding these polypeptides, vectors and host cells comprising such polynucleotides, methods of using such host cells to produce polypeptides, and other therapeutic products comprising the polypeptides (including fusion proteins in which the CD39-like polypeptide is fused to a heterologous peptide or polypeptide, such as an immunoglobulin constant region, or derivatives in which the CD39-like polypeptide is modified by water soluble polymers to increase its half-life) are also comprehended by the invention, as are methods of treating a subject suffering from a disorder relating to thrombosis, coagulation or platelet aggregation by administering such therapeutic products.

The invention further comprises methods of inhibiting platelet aggregation in a mammalian subject by reducing the ratio of ADP:ATP in a mammalian subject to a less than normal ratio by administering the polypeptides of the invention or by administering polypeptides with ADPase activity and at least about 90% sequence identity to SEQ ID NO: 3, 25 or 27. Preferably the ratio of ADP:ATP is reduced without significantly affecting ATP levels. In one embodiment, the ADP:ATP ratio is reduced systemically in circulation. In another embodiment, the ADP:ATP ratio is reduced locally, for example, in heart, brain, kidney, lungs, limbs or other organs.

Methods of identifying compounds capable of reducing the ratio of ADP:ATP to a less than normal ratio are also contemplated. For example, compounds may be identified by steps including: determining apyrase activity of said compound on ATP; determining apyrase activity of said compounds on ADP; and selecting a compound that has greater activity with respect to ADP compared to ATP. Exemplary compounds to be screened include, but are not limited to, CD39-L4 and CD39-L2 variants.

Gene therapy techniques are also provided to modulate disease states associated with CD39-L4 or CD39-L2 expression and/or biological activity. Delivery of a functional CD39-L4 or CD39-L2 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments).

The invention also relates to methods for producing polypeptides of the invention comprising growing a culture of cells of the invention in a suitable culture medium under conditions permitting expression of the desired polypeptide, and purifying the protein from the cells or the culture medium. Preferred embodiments include those in which the protein produced by such process is a mature form of the protein.

Protein compositions of the present invention, including therapeutic compositions, comprise polypeptides of the invention and optionally an acceptable carrier, such as a hydrophilic (e.g., pharmaceutically acceptable) carrier.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, because the expression of CD39-L4 and CD39-L2 mRNA is largely restricted to specific tissues (CD39-L4 in macrophages and CD39-L2 in adult heart and fetal brain), polynucleotides of the invention can be used as hybridization probes to detect the presence of specific mRNA in a sample using, e.g., in situ hybridization.

In other exemplary embodiments, the polynucleotides are used in diagnostics as expressed sequence tags for identifying expressed genes or, as well known in the art and exemplified by Vollrath, et al., Science 258:52–59 (1992), as expressed sequence tags for physical mapping of the human genome.

A polynucleotide according to the invention can be joined to any of a variety of other nucleotide sequences by well-established recombinant DNA techniques (see Sambrook, J., et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The polypeptides according to the invention can be used in a variety of conventional procedures and methods that are currently applied to other proteins. For example, a polypeptide of the invention can be used to generate an antibody which specifically binds the polypeptide. The polypeptides of the invention having ATPDase activity are also useful for inhibiting platelet aggregation and can therefore be employed in the prophylaxis or treatment of pathological conditions caused by the inflammatory response. The polypeptides of the invention can also be used as molecular weight markers, and as a food supplement.

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention and anti-idiotype antibodies.

Antibodies of the invention are useful for detection and/or purification of the polypeptides of the invention.

Methods are also provided for preventing, treating or ameliorating a medical condition, including thrombotic diseases, which comprises administering to a mammalian subject, including but not limited to humans, a therapeutically effective amount of a composition comprising a polypeptide of the invention or a therapeutically effective amount of a composition comprising a binding partner of (e.g., antibody specifically reactive for) CD39-like polypeptides of the invention. The mechanics of the particular condition or pathology will dictate whether the polypeptides of the invention or binding partners (or inhibitors) of these would be beneficial to the individual in need of treatment.

The invention also provides a method of inhibiting platelet function comprising administering a CD39-L4 or CD39-L2 polypeptide of the invention to a medium comprising platelets. According to this method, polypeptides of the invention can be administered to produce an in vitro or in vivo inhibition of platelet function. A polypeptide of the invention can be administered in vivo as antithrombotic agent alone or as an adjunct to other therapies.

Also provided are methods of hydrolyzing nucleotide diphosphates comprising administering CD39-L4 or CD39-L2 polypeptides of the invention to a medium comprising nucleotidediphosphates. According to this method, polypeptides of the invention can be administered to produce an in vitro or in vivo hydrolysis of nucleotidediphosphates. A polypeptide of the invention can be administered in vivo alone or as an adjunct to other therapies. For example, CD39-L4 or CD39-L2 polypeptides of the invention may be administered to prevent or treat cancer conditions involving elevated levels of one or more nucleotide diphosphates.

The invention further provides methods for manufacturing medicaments useful in the above described methods relating to platelet aggregation and thrombosis.

The invention also provides methods for detecting or quantitating the presence of the polynucleotides or polypeptides of the invention in a tissue or fluid sample, and corresponding kits that comprise suitable polynucleotide probes or antibodies, together with an optional quantitative standard. Such methods and kits can be utilized as part of prognostic and diagnostic evaluation of patients and for the identification of subjects exhibiting a predisposition to platelet mediated conditions.

The invention also provides methods for the identification of compounds that modulate (i.e. increase or decrease) the expression or activity of the polynucleotides and/or polypeptides of the invention. Such methods can be utilized, for example, for the identification of compounds and other substances that interact with (e.g., bind to) the polypeptides of the invention, and assays for identifying compounds and other substances that enhance or inhibit the activity of the polypeptides of the invention, such assays comprising the step of measuring activity of such polypeptides in the presence and absence of the test compound.

5. BRIEF DESCRIPTION OF THE DRAWINGS

FIG. 1 shows polynucleotide sequences according to the invention. SEQ ID NO:1 was obtained from the b2HFLS20W cDNA library using standard PCR, sequencing by hybridization signature analysis, and single pass gel sequencing technology. A—adenosine; C—cytosine; G—guanosine; T—thymine. Ambiguous positions are designated as follows: R indicates A or G; M indicates A or C; W indicates A or T; Y indicates C or T; S indicates C or G; K indicates G or T; V indicates A or C or G; H indicates A or C or T; D indicates A or G or T; B indicates C or G or T; and N indicates any of the four bases.

SEQ ID NO:2 is an extended version of SEQ ID NO:1 which was obtained as described in Example 2.

FIG. 2 shows an amino acid sequence corresponding to the polynucleotide sequence of SEQ ID NO:2. This sequence is designated as SEQ ID NO:3. The open reading frame encoding SEQ ID NO:3 begins at nucleotide 246 (numbered from the 5' end) of SEQ ID NO:2. A—Alanine; R—Arginine; N—Asparagine; D—Aspartic Acid; C—Cysteine; E—Glutamic Acid; Q—Glutamine; G—Glycine; H—Histidine; I—Isoleucine; L—Leucine; K—Lysine; M—Methionine; F—Phenylalanine; P—Proline; S—Serine; T—Threonine; W—Tryptophan; Y—Tyrosine; V—Valine; X—any of the twenty amino acids.

FIGS. 3A and 3B shows the amino acid sequence alignment of SEQ ID NO:3 (identified as "246 prot") and human CD39 ("CD39Human.seq"). The amino acid residues are designated as for FIG. 2. The alignment was generated using the Jotun Hein method with the PAM250 residue weight table. Gaps are indicated by dashes; residues that are identical between the two sequences (within 1 distance unit) are boxed.

FIGS. 4A and 4B show the amino acid sequence alignment of SEQ ID NO:3 (identified as "264 prot") and murine NTPase ("mur ntpase"). The amino acid residues are designated as for FIG. 2. The alignment was generated as discussed for FIGS. 3A and 3B. Gaps are indicated by dashes; residues that are identical between the two sequences (within 1 distance unit) are boxed.

FIG. 5 shows the apyrase conserved regions (ACR) in CD39-L4 in bold. ACR I starts at Phe 53, ACR II starts at Pro 124 and ACR III starts at Met 167. The boxed sections highlight the amino acid substitutions that were made in the wild type CD39-L4 amino acid sequence to form mutants designated ACRI, ACRII and ACRIII.

FIG. 6 (SEQ ID NOS: 6 and 7) shows the nucleotide and corresponding amino acid sequences of a preferred ACRIII mutant containing the following substitutions in the wild type CD39-L4 amino acid sequence: D168→T, S170→Q and L175→F. Changes in both sequences are shown in bold and are underlined. The G to A and A to C changes at positions 502 and 503 produce a Thr, the T to C, C to A and C to A changes at positions 508–510 result in a Gln and the A to C changed at position 525 results in a Phe.

FIG. 7 shows the ADPase activity of CD39-L4 variants ACRI, ACRII and ACRIII in comparison to wild type CD39-L4: (1) CD39-L4 ACR I mutant; (2) CD39-L4 ACR II mutant; (3) CD39-L4 ACR III mutant; (4) CD39-L4 wild type; (5) sCD39; and (6) pSecTag2 vector (Invitrogen).

Figure 8:
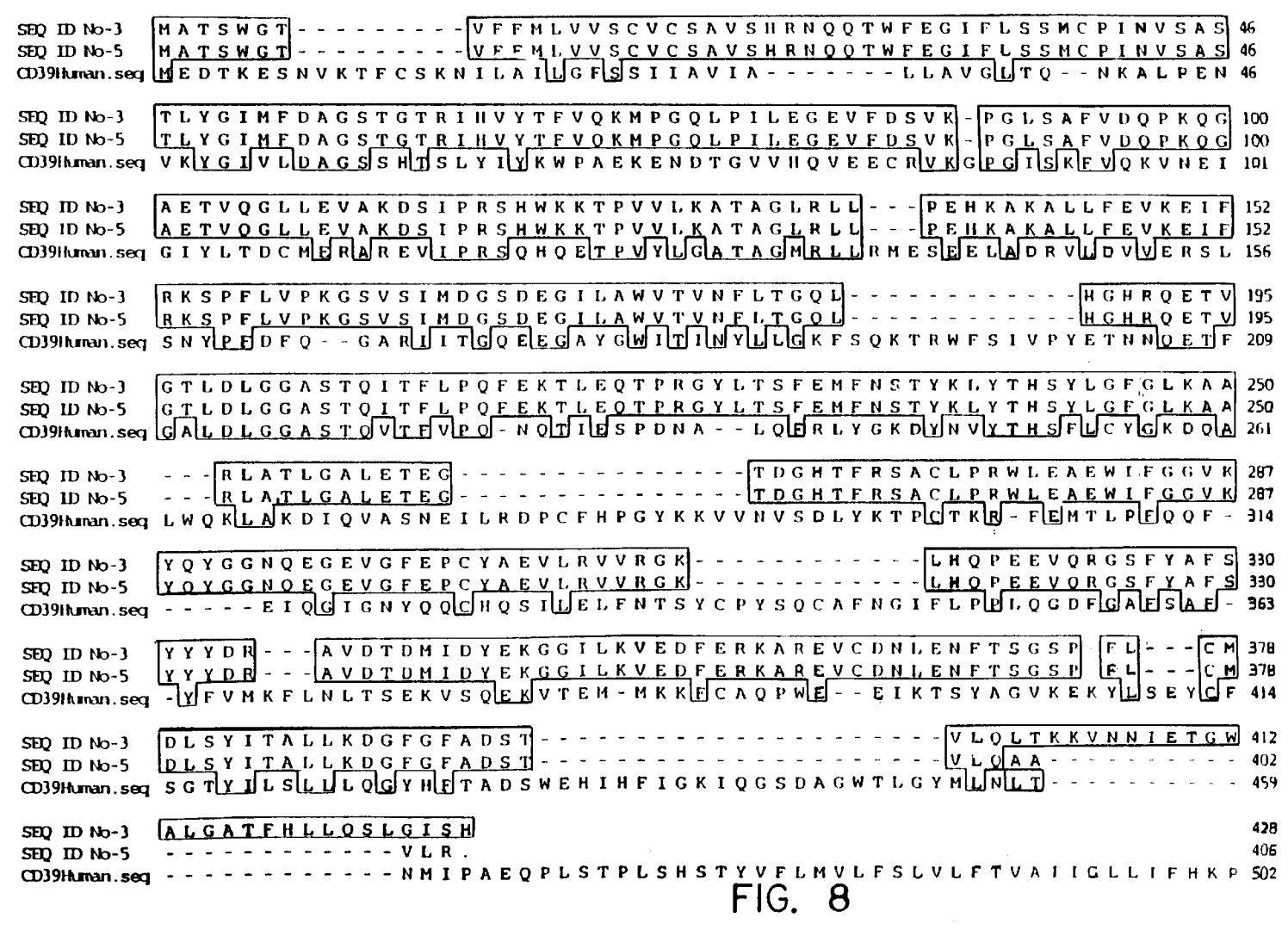

FIG. 8 shows the amino acid sequence alignment of SEQ ID NO. 3, SEQ ID NO. 25 (previously identified as SEQ ID NO. 5 in FIG. 5 of U.S. Ser. No. 09/122,449) and human CD39 ("CD39Human.seq") (SEQ ID NO: 55). The alignment was generated using the Jotun Hein method with the PAM250 residue weight table. Gaps are indicated by dashes; residues that are identical between the two sequences (within 1 distance unit) are boxed.

Figure 9:
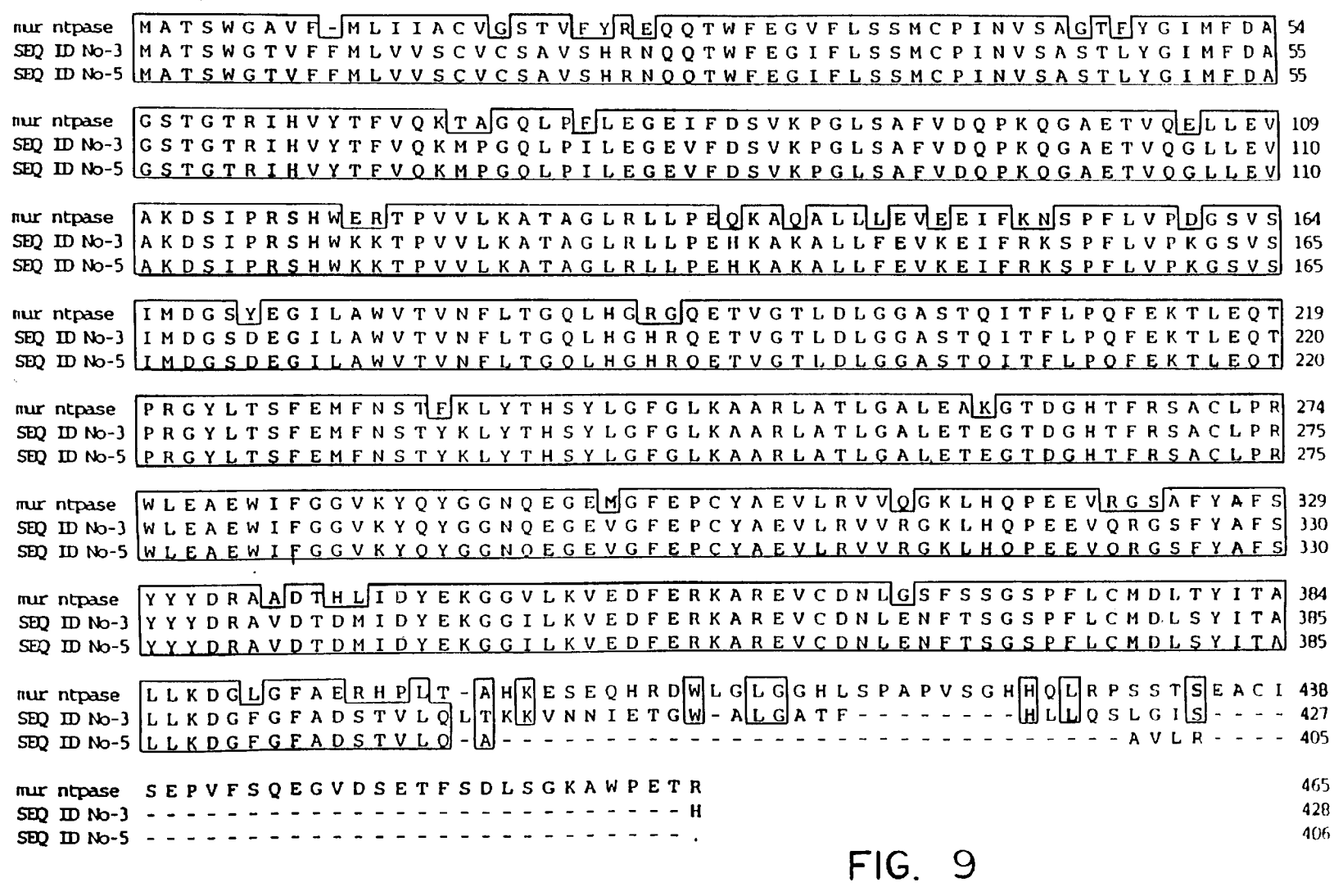

FIG. 9 shows the amino acid sequence alignment of SEQ ID NO. 3, SEQ ID NO. 25 (previously identified as SEQ ID NO. 5 in FIG. 6 of U.S. Ser. No. 09/122,449) and the murine NTPase ("mur ntpase") (SEQ ID NO: 56). The alignment was generated as discussed for FIG. 8. Gaps are indicated by dashes; residues that are identical between the two sequences (within 1 distance unit) are boxed.

6. DETAILED DESCRIPTION

6.1 Definitions

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, to provide a synthetic nucleic acid which is capable of being expressed in a recombinant transcriptional unit comprising regulatory elements derived from a microbial or viral operon.

An "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

"Oligonucleotides" or "nucleic acid probes" are prepared based on the cDNA sequence provided in the present invention. Oligonucleotides comprise portions of the DNA sequence having at least about 15 nucleotides and usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs are present in a cell or tissue or to isolate similar nucleic acid sequences from chromosomal DNA as described by Walsh, P.S., et al (1992 PCR Methods Appl 1:241–250).

The term "probes" includes naturally occurring or recombinant single-or double-stranded nucleic acids or chemically synthesized nucleic acids. They may be labeled by nick translation, Klenow fill-in reaction, PCR or other methods well known in the art. Probes of the present invention, their preparation and/or labeling are elaborated in Sambrook, J., et al (1989) Molecular Cloning: A Laboratory Manual, Cold Spring Harbor Laboratory, NY; or Ausubel, F. M., et al (1989) Current Protocols in Molecular Biology, John Wiley & Sons, New York N.Y., both incorporated herein by reference.

The term "stringent" is used to refer to conditions that are commonly understood in the art as stringent. An exemplary set of conditions include a temperature of 60–70° C., (preferably about 65° C.) and a salt concentration of 0.70 M to 0.80 M (preferably about 0.75M). Further exemplary conditions include, hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0. 1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

The term "recombinant," as used herein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern different from that expressed in mammalian cells.

The term "recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extrachromosomally. The cells can be prokaryotic or eukaryotic. Recombinant expression systems as defined herein will express heterologous polypeptides or proteins upon induction of the regulatory elements linked to the DNA segment or synthetic gene to be expressed.

The term "open reading frame," ORF, means a series of triplets coding for amino acids without any termination codons and is a sequence translatable into protein.

The term "expression modulating fragment," EMF, means a series of nucleotide molecules which modulates the expression of an operably linked ORF or EMF. As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression of an operably linked ORF in response to a specific regulatory factor or physiological event.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems known in the art.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

"Active" refers to those forms of the polypeptide which retain the biologic and/or immunologic activities of any naturally occurring polypeptide.

"Naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

"Derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

"Recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a mutant sequence varies from one of those listed herein by no more than about 20% (i.e., the number of substitutions, additions, and/or deletions in a mutant sequence, as compared to the corresponding listed sequence, divided by the total number of residues in the mutant sequence is about 0.2 or less). Such a mutant sequence is said to have 80% sequence identity to the listed sequence. In one embodiment, a mutant sequence of the invention varies from a listed sequence by no more than 10% (90% sequence identity), in a variation of this embodiment, by no more than 5% (95% sequence identity), and in a further variation of this embodiment, by no more than 2% (98% sequence identity). Mutant amino acid sequences according to the invention generally have at least 95% sequence identity with a listed amino acid sequence, whereas mutant nucleotide sequence of the invention can have lower percent sequence identities. For the purposes of the present invention, sequences having substantially equivalent biological activity and substantially equivalent expression characteristics are considered substantially equivalent. For the purposes of determining equivalence, truncation of the mature sequence should be disregarded.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polypeptide sequence may be reflected in the polypeptide or domains of other peptides added to the polypeptide to modify the properties of any part of the polypeptide, to change characteristics such as ligand-binding affinities, interchain affinities, or degradation/turnover rate.

"Activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

Each of the above terms is meant to encompasses all that is described for each, unless the context dictates otherwise.

6.2 Hybridization Conditions

Suitable hybridization conditions may be routinely determined by optimization procedures or pilot studies. Such procedures and studies are routinely conducted by those skilled in the art to establish protocols for use in a laboratory. See e.g., Ausubel, et al., Current Protocols in Molecular Biology, Vol. 1–2, John Wiley & Sons (1989); Sambrook, et al., Molecular Cloning A Laboratory Manual, 2nd Ed., Vols. 1–3, Cold Springs Harbor Press (1989); and Maniatis, et al., Molecular Cloning: A Laboratory Manual, Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

6.3 Nucleic Acids of the Invention

The sequences falling within the scope of the present invention are not limited to the specific sequences herein described, but also include allelic variations thereof. Allelic variations can be routinely determined by comparing the sequence provided in SEQ ID NOs: 1, 2, 24 or 26, a representative fragment thereof, or a nucleotide sequence at least 99.9% identical to SEQ ID NO: 1, 2, 24 or 26 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

Any specific sequence disclosed herein can be readily screened for errors by resequencing a particular fragment, such as an ORF, in both directions (i.e., sequence both strands).

The present invention further provides recombinant constructs comprising a nucleic acid having the sequence of any one of SEQ ID NO: 1, 2, 24 or 26, the mature protein coding sequence or a fragment thereof. The recombinant constructs of the present invention comprise a vector, such as a plasmid or viral vector, into which a nucleic acid having the sequence of any one of SEQ ID NO: 1, 2, 24 or 26 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequences in FIG. 1, which fragment is greater than about 10 bp, preferably 20–50 bp, and even greater than 100 bp, including 200 bp or greater, 300 bp or greater, 400 bp or greater, and 500 bp or greater.

In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982).

PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook, et al., supra, and Current Protocols in Molecular Biology, Ausubel, et al.

Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Furthermore, knowledge of the DNA sequence provided by the present invention allows for the modification of cells to permit, or increase, expression of endogenous CD39-like polypeptides. Cells can be modified (e.g., by homologous recombination) to provide increased CD39-like expression by replacing, in whole or in part, the naturally occurring CD39-like promoter with all or part of a heterologous promoter so that the cells express CD39-like polypeptides at a higher level. The heterologous promoter is inserted in such a manner that it is operatively linked to CD39-like encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the CD39-like coding sequence, amplification of the marker DNA by standard selection methods results in co-amplification of the CD39-like coding sequences in the cells.

The polynucleotides of the present invention also make possible the development, through, e.g., homologous recombination or knock out strategies, of animals that fail to express functional CD39-like polypeptides or that express a variant of a CD39-like polypeptide. Such animals are useful as models for studying the in Vivo activities of CD39-like polypeptides as well as for studying modulators of CD39-like polypeptides.

6.4 Identification of Polymorphisms

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labelled nucleotides). In addition, traditional restriction fragment length polymorphism analysis (using restriction enzymes that provide differential digestion of the genomic DNA depending on the presence or absence of the polymorphism) may be performed.

Alternatively, a polymorphism resulting in a change in the amino acid sequence could also be detected by detecting a corresponding change in amino acid sequence of the protein, e.g., by an antibody specific to the variant sequence.

6.5 Hosts

The present invention further provides host cells containing SEQ ID NO: 1, 2, 24 or 26 of the present invention, wherein the nucleic acid has been introduced into the host cell using known transformation, transfection or infection methods. The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L., et al., Basic Methods in Molecular Biology (1986)).

The host cells containing one of SEQ ID NO: 1, 2, 24 or 26 of the present invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level.

Mature proteins can be expressed in mammalian cells, yeast, bacteria, insect cells or other cells under the control of appropriate promoters. Cell-free translation systems can also be employed to produce such proteins using RNAs derived from the DNA constructs of the present invention. Appropriate cloning and expression vectors for use with prokaryotic and eukaryotic. hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

6.6 Peptides

The present invention further provides isolated polypeptides encoded by the nucleic acid fragments of the present invention or by degenerate variants of the nucleic acid fragments of the present invention. Fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention. Analogs of the polypeptides of the invention can be fused to another moiety or moieties, e,g., targeting moiety or another therapeutic agent. Such analogs may exhibit improved properties such as activity and/or stability. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs which encode proteins.

The invention also provides both full length and mature forms (for example, without a signal sequence or precursor sequence) of CD39-like polypeptides. The full length form of such proteins is identified in the sequence listing by translation of the nucleotide sequence of each disclosed clone. The mature form of such protein may be obtained by expression of the full-length polynucleotide in a suitable mammalian cell or other host cell. The sequence of the mature form of the protein is also determinable from the amino acid sequence of the full length form.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel, et al., Current Protocols in Molecular Biology.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The purified polypeptides are used in in vitro binding assays which are well known in the art to identify molecules which bind to the polypeptides. These molecules include but are not limited to for example, small molecules, molecules from combinatorial libraries, antibodies or other proteins. The molecules identified in the binding assay are then tested for antagonist or agonist activity in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to the tumor or other cell by the specificity of the binding molecule for SEQ ID NOs:3–4.

6.7 Gene Therapy

Mutations in the CD39-like gene that result in loss of normal function of the CD39-like gene product underlie CD39-related human disease states. The invention comprehends gene therapy to restore CD39-like activity that would thus be indicated in treating those disease states. Delivery of a functional CD39-like gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no 6679, pp. 25–30 (1998). For additional reviews of gene therapy technology, see Friedmann, Science, 244: 1275–1281 (1989); Verma, Scientific American: 68–84 (1990); and Miller, Nature, 357: 455–460 (1992). Alternatively, it is contemplated that in other human disease states, preventing the expression of or inhibiting the activity of CD39-like polypeptides will be useful in treating the disease states. It is contemplated that antisense therapy or gene therapy could be applied to negatively regulate the expression of CD39-like polypeptides.

6.8 Deposit of clone

A plasmid containing DNA encoding the ACR III mutant was deposited with the American Type Culture Collection (ATCC), 10801 University Avenue, Manassas, Va., on Jul. 13, 1999 under the terms of the Budapest Treaty (ATCC accession no. PTA-346).

6.9 Antibodies

In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth, et al., J. Immunol. 35:1–21 (1990); Kohler and Milstein, Nature 256:495–497 (1975)), the trioma technique, the human B-cell hybridoma technique (Kozbor, et al., Immunology Today 4:72 (1983); Cole, et al., in Monoclonal Antibodies and Cancer Therapy, Alan R. Liss, Inc. (1985), pp. 77–96). in addition, techniques for preparing chimeric and humanized antibodies (including polypeptides containing CDR and/or antigen-binding sequences of antibodies) are well known in the art.

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or -galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp. Cell Research. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms. etc. Procedures for accomplishing such labeling are well-known in the art, for example, see (Stemberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics.

The present invention further provides the above-described antibodies immobilized on a solid support. Examples of such solid supports include plastics such as polycarbonate, complex carbohydrates such as agarose and sepharose, acrylic resins and polyacrylamide and latex beads. Techniques for coupling antibodies to Such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

6.10 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate manufactures comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NO: 1, 2, 24 or 26, a representative fragment thereof, or a nucleotide sequence at least 99.9% identical to SEQ ID NO: 1, 2, 24 or 26 in computer readable form, a skilled artisan can routinely access the sequence information for a variety of purposes. Computer software is publicly available which allows a skilled artisan to access sequence information provided in a computer readable medium. Software which implements the BLAST (Altschul, et al., J. Mol. Biol. 215:403–410 (1990)) and BLAZE (Brutlag, et al., Comp. Chem. 17:203–207 (1993)) search algorithms on a Sybase system may be used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems is suitable for use in the present invention.

As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems.

As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

6.11 Expression Modulating Sequences

EMF sequences can be identified within a genome by their proximity to the ORFs. An intergenic segment, or a fragment of the intergenic segment, from about 10 to 200 nucleotides in length, taken 5' from any ORF will modulate the expression of an operably linked 3' ORF in a fashion similar to that found with the naturally linked ORF sequence. As used herein, an "intergenic segment" refers to the fragments of a genome which are between two ORF(S) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below. A sequence which is suspected of being an EMF is cloned in all three reading frames in one or more restriction sites upstream from the marker. sequence in the EMF trap vector. The vector is then transformed into an appropriate host using known procedures and the phenotype of the transformed host is examined under appropriate conditions. As described above, an EMF will modulate the expression of an operably linked marker sequence.

6.12 Triplex Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee, et al., Nucl. Acids Res. 6:3073 (1979); Cooney, et al., Science 15241:456 (1988); and Deran, et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)).

Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

6.13 Diagnostic Assays and Kits

The present invention further provides methods to identify the expression of one of the ORFs of the present invention, or homolog thereof, in a test sample, using a nucleic acid probe or antibodies of the present invention.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985).

The test samples of the present invention include cells, protein or membrane extracts of cells, or biological fluids Such as sputum, blood. serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention.

Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe.

Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

6.14 Screening Assays

Using the isolated proteins of the present invention, the present invention further provides methods of obtaining and identifying agents which bind to a protein encoded by one of the ORFs from a nucleic acid with a sequence of one of SEQ ID NO: 1, 2, 24 or 26, or to a nucleic acid with a sequence of one of SEQ ID NO: 1, 2, 24 or 26.

In detail, said method comprises the steps of: (a) contacting an agent with an isolated protein encoded by one of the ORFs of the present invention, or nucleic acid of the invention; and (b) determining whether the agent binds to said protein or said nucleic acid.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby, et al., Application of Synthetic Peptides: Antisense Peptides," In Synthetic Peptides, A User's Guide, W. H. Freeman, NY (1992), pp. 289–307, and Kaspczak, et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee, et al., Nucl. Acids Res. 6:3073 (1979); Cooney, et al., Science 241:456 (1988); and Dervan, et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

6.15 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NO: 1, 2 24 or 26. Because the corresponding gene is expressed in only one out of 18 tissues tested, namely macrophages. a hybridization probe derived from SEQ ID NO: 1, 2, 24 or 26 can be used as an indicator of the presence of macrophage RNA in a sample. Any suitable hybridization technique can be employed, such as, for example, in situ hybridization.

PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places. in Verma, et al (1988) Human Chromosomes: A Manual of Basic Techniques, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981 f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence may be used to produce purified polypeptides using well known methods of recombinant DNA technology. Among the many publications that teach methods for the expression of genes after they have been isolated is Goeddel, (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

6.15.1 Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto. Canada) which consists of a square (60×60 cm) polysulfone polymer (Gelman Tuffryn HT-450, 0.45$\mu$pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF-replicator. One such instrument replicates growth from each of the 1600 cells of the ISO-GRID and enables many copies of the master HGMF to be made (Peterkin et al., 1987).

Sharpe et al. (1989) also used ISO-GRID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation With small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 $\mu$M/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula BxNn, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as (N)nBx(N)m.

6.15.2 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) describe the use of Biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond. allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/$\mu$l). and denaturing for 10 min. at 95° C. and cooling on ice for 10 min. Ice-cold 0.1 M 1-methylimidazole, pH 7.0 (1-MeIm7), is then added to a final concentration of 10 mM 1-MeIm7. A ss DNA solution is then dispensed into CovaLink NH strips (75 µl/well) standing on ice.

Carbodiimide 0.2 M 1-ethyl-3-(3-dimethylaminopropyl)-carbodiimide (EDC), dissolved in 10 mM 1-MeIm7, is made fresh and 25 µl added per well. The strips are incubated for 5 hours at 50° C. After incubation the strips are washed using, e.g., Nunc-immuno Wash; first the wells are washed 3 times, then they are soaked with washing solution for 5 min., and finally they are washed 3 times (where in the washing, solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleotide 3'-reagent through the phosphate group by a covalent phosphodiester link to aliphatic hydroxyl groups canied by the support. The oligonucleotide is then synthesized on the supported nucleotide and protecting groups removed from the synthetic oligonucleotide chain under standard conditions that do not cleave the oligonucleotide from the support. Suitable reagents include nucleotide phosphoramidite and nucleotide hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al.(1991); or linked to Teflon using the method of Duncan & Cavalier (1988); all references being specifically incorporated herein.

To link an oiigonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucieotides is to utilize the light-generated synthesis described by Pease et al., (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

6.15.3 Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 µg instead of 2–5 µg); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

6.15.4 Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$, depending on the type of label used. By avoiding spotting in some preselected number of rows and columns, separate subsets (subarrays) may be formed. Samples in one subarray may be the same genomic segment of DNA (or the same gene) from different individuals or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm² and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

6.15.5 Sequence comparisons

BLAST, which stands for Basic Local Alignment Search Tool, is used to search for local sequence alignments (Altschul, S. F., (1993) J Mol Evol 36:290–300; Altschul, S. F., et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

6.16 SEQ ID NOs

Referring to FIG. 1, SEQ ID NO:1 is the nucleotide sequence of an expressed sequence tag corresponding to a polynucleotide isolated from a cDNA library of human fetal liver-spleen. SEQ ID NO:2 is an extended version of SEQ ID NO:1 obtained as described in Example 2, and the encoded polypeptide in SEQ ID NO: 3 is referred to herein as CD39-L4. SEQ ID NO:2 encodes a polypeptide having the amino acid sequence of SEQ ID NO:3 (shown in FIG. 2). The open reading frame corresponding to SEQ ID NO:3 starts at nucleotide 246, as numbered from the 5' end of SEQ ID NO:2. This open reading frame encodes a polypeptide 428 amino acids in length. The estimated molecular weight of the unglycosylated polypeptide is approximately 47.52 kDa.

Protein database searches with the BLAST algorithm indicate that SEQ ID NO:3 is homologous to the CD39 family. FIGS. 3A and 3B shows the amino acid sequence alignment between SEQ ID NO:3 (identified as "246 prot") and human CD39 ("CD39Human.seq"), indicating that the two sequences share 30% amino acid sequence identity. Moreover, a higher degree of homology between the apyrase conserved regions (Kaczmarek et al., J. Biol. Chem. 271:33116–33122 (1996) is observed. In particular, an almost perfect match to a putative ATP-binding region was found from amino acids 54–58, DAGST (DAGSS in CD39). In addition, the DLGGASTQ motif (DLGGASTQ in CD39), which is very well conserved among ATPDases, is found from amino acids 199–206 in SEQ ID NO:3. Other regions conserved in apyrases were found from amino acids 129–134, ATAGLR (ATAGMR in CD39) and from amino acids 169–173, GSDEG (GQEEG in CD39).

SEQ ID NO:3 differs from CD39 in that SEQ ID NO:3 contains a hydrophobic stretch of 22 amino acids at its amino terminus, which is indicative of a leader peptide. SEQ ID NO:3 also lacks the transmembrane domain found at the carboxyl terminus of CD39. These features indicate that SEQ ID NO:3 is a soluble ATPDase.

SEQ ID NO:3 shares an even higher degree of homology (86% identity) with a murine NTPase, as shown in the amino acid sequence alignment presented in FIGS. 4A and 4B (SEQ ID NO:3 is identified as "246 prot," and mouse CD39 as "mur ntpase").

The message encoding SEQ ID NO:3 is tightly regulated in a tissue-specific manner. An expression study using a semiquantitative PCR/Southern blot approach revealed a significant level of expression in macrophage. In contrast, human CD39 is expressed in tissues such as placenta, lung, skeletal muscle, kidney, and heart.

SEQ ID NO:4 is a polynucleotide sequence for CD39-L4 that was amplified from a macrophage cDNA library. SEQ ID NO: 5 is the corresponding amino acid sequence (and is identical to SEQ ID NO: 3).

SEQ ID NO: 6 is the polynucleotide sequence for a CD39-L4 variant designated ACRIII, wherein the following amino acid substitutions have been made: D168→T, S170→Q and L175→F; SEQ ID NO: 7 is the corresponding amino acid sequence.

SEQ ID NO: 8 is the genomic sequence for the human CD39-L4 gene; exons appear at nucleotides 1–288 (exon 1), 1281–1580 (exon 2), 1820–1855 (exon 3) 2467–2555 (exon 4), 2863–2942 (exon 5), 3889–3950 (exon 6), 4894–4995 (exon 7), 5847–5987 (exon 8), 6966–7138 (exon 9) and 8556–9365 (exon 10).

SEQ ID NO: 24 is the polynucleotide sequence for a CD39-L4 splice variant that creates an isoform designated CD39-L66. SEQ ID NO: 25 is the corresponding amino acid sequence.

SEQ ID NO: 26 is the polynucleotide sequence for CD39-L2. SEQ ID NO: 27 is the corresponding amino acid sequence.

SEQ ID NO: 42 is the complete genomic sequence for the human CD39-L4 gene; exons appear at nucleotides 245–461, 1454–1533, 2734–2877, 4364–4439, 4679–4714, 5326–5414, 5723–5802, 6751–6812, 7758–7859, 8712–8852, 9831–9887, 10383–10498, 11916–12002 and 14472–14526.

6.17 Uses of Novel CD39-Like Polypeptides and Antibodies

Polypeptides of the invention having ATPDase, including NDPase, activity are useful for inhibiting platelet function and can therefore be employed in the prophylaxis or treatment of pathological conditions caused by or involving thrombosis or excessive coagulation or excessive platelet aggregation, such as myocardial infarction, cerebral ischemia, angina, and the like. Polypeptides of the invention can also be used in the maintenance of vascular grafts. Platelet function can be measured by any of a number of standard assays, such as, for example, the platelet aggregation assay described in Example 5.

Such pathological conditions include conditions caused by or involving arterial thrombosis, such as coronary artery thrombosis and resulting myocardial infarction, cerebral artery thrombosis or intracardiac thrombosis (due to, e.g., atrial fibrillation) and resulting stroke, and other peripheral arterial thrombosis and occlusion; conditions associated with venous thrombosis, such as deep venous thrombosis and pulmonary embolism; conditions associated with exposure of the patient's blood to a foreign or injured tissue surface, including diseased heart valves, mechanical heart valves, vascular grafts, and other extracorporeal devices such as intravascular cannulas, vascular access shunts in hemodialysis patients, hemodialysis machines and cardiopulmonary bypass machines; and conditions associated with coagulapathies, such as hypercoagulability and disseminated intravascular coagulopathy. Co-administration of other agents suitable for treating the pathological condition, e.g., other anti-coagulation agents, is also contemplated.

CD39-L4 and CD39-L2 are uniquely specific for ADP and do not substantially hydrolyze ATP. Thus, adverse side effects from hydrolysis of circulating ATP are avoided.

For instance, ATP is known to act as an extracellular signal in many tissues. In the heart, extracellular ATP modulates ionic processes and contractile function (for review see Burnstock, G., Neuropharmacology 36:1127). Recently, it has been shown that extracellular ATP markedly inhibits glucose transport in rat cardiomyocytes (Fisher, Y. et al., *J. Biol. Chem.* 274:755–761. Another source of extracellular ATP is that released from parenchymal cells under hypoxic or ischemic conditions (Skobel E., and Kammermeier, H. Biochim. Biophys. Acta 1362:128–134). ATP is also involved in the modulation of anti-IgE-induced release of histamine from human lung mast cells (Schulman, E. S., et al., Am. J. Respir. Cell Mol. Biol. 20:520–537).

CD39-L4 and CD39-L2 polypeptides of the invention are thus expected to be useful in modulating disease states (including platelet aggregation, inflammation and apoptosis) associated with ADP or other purinergic signaling by reducing the levels of NDPs.

The ability of CD39-L4 and CD39-L2 to hydrolyze NDPs other than ADP has implications outside the circulatory system. For instance, it has been reported that UDP is the most potent agonist for the human $P2Y_6$ receptor. Communi, et al., Bioch Bioph Res Com 222:303–308 (1996). This receptor is expressed in several tissues including infiltrating T cells present in inflammatory bowel disease. Somers, et al., Lab Invest 78:1375–1383 (1998). In this microenvironment, a molecule with the enzymatic properties of CD39-L4 (including CD39-L4, the ACR III mutant thereof, CD39-L66, and CD39-L2) could influence (i.e., enhance or inhibit) T cell responses by modifying the extracellular half-life of UDP. Thus, the invention contemplates use of polypeptides of the invention for prophylaxis or treatment of inflammation related disorders including disorders involving sepsis or systemic inflammatory response syndrome or SIRS (and associated conditions such as fever, tachycardia, tachypnea, cytokine overstimulation, increased vascular permeability, hypotension, coniplement activation, disseminated intravascular coagulation, anemia, thrombocytopenia, leukopenia, pulmonary edema, adult respiratory distress syndrome, intestinal ischemia, renal insufficiency and failure, metabolic acidosis and multiorgan dysfunction syndrome), including SIRS secondary to surgery, traumatic injury, hemorrhage, burns, endotoxin, cytokine overstimulation; thrombosis; atherosclerosis; acute pancreatitis; dermatosis, including psoriasis; cirrhosis, reperfusion injury; asthma; multiple sclerosis; arthritis, including rheumatoid arthritis, reactive arthritis and chronic inflammatory arthritis; vasculitis; glomerulonephritis; lupus; myasthenia gravis; experimental allergic encephalomyelitis (EAE); other atitoimmune disorders; ulcerative colitis; Crohn's disease; inflammatory bowel disease; necrotizing enterocolitis; pancreatic cell damage from diabetes mellitus type 1; hemodialysis; leukapheresis; granulocyte transfusion associated syndrome; rejection reactions after allograft and xenograft transplantation, including graft versus host disease; or other inflammatory disorders.

Nucleotides have been reported to be agonists of apoptosis and ecto-apyrases may also be used to inhibit apoptosis.

Another role for CD39-L4 has been suggested by the report that mouse CD39-L4 maps closely to a locus associated with audiogenic brain seizures in mice. See Chadwick, et al., Genomics 50:357–367 (1998); Seyfried, et al., Genetics 99:117–126 (1981). This locus, known as Asp-1, is thought to be linked or to correspond to a factor that influences $Ca^2$-ATPase activity. Neumann, et al., Behav. Genetics 20:307–323 (1990). Thus, CD39-L4 and CD39-L2 may play a role in neurological disorders, particularly since a CD39-L2 variant has been observed to be expressed in brain.

In addition, elevated levels of nucleotides have been associated with cancer conditions, including endometrial cancer, myeloid leukemia and melanoma. Thus, CD39-L4 and CD39-L2 polypeptides of the invention are expected to be useful in preventing or treating such conditions by reducing circulating or local levels of nucleotide diphosphates.

Additionally, the polypeptides of the invention can be used as molecular weight markers, and as a food supplement. A polypeptide consisting of SEQ ID NO:3, for example, has a molecular mass of approximately 47.52 kD in its unglycosylated form. Protein food supplements are well known and the formulation of suitable food supplements including polypeptides of the invention is within the level of skill in the food preparation art.

The polypeptides of the invention are also useful for making antibody substances that are specifically immunoreactive with CD39-like proteins. Antibodies and portions thereof(e.g., Fab fragments) which bind to the polypeptides of the invention can be used to identify the presence of such polypeptides in a sample. For example, the level of the native protein corresponding to SEQ ID NO:3 in a blood sample can be determined as an indication of vascular condition. Such determinations are carried out using any suitable immunoassay format, and any polypeptide of the invention that is specifically bound by the antibody can be employed as a positive control.

Additionally, the polypeptides of the invention are useful for modulating the ratios of levels of adenosine molecules in vivo to regulate homeostasis. Adenosine diphosphate (ADP) is an agonist of platelet activation and aggregation. It has been demonstrated that the P2Y receptor (and others including P2T and P2Y1 and potentially others) transduces this signal. Adenosine triphosphate (ATP) also binds to this receptor, but acts as an antagonist. Therefore, the ratios of levels of ATP/ADP can significantly influence in vivo platelet activation and aggregation. Agents that specifically decrease levels of ADP not only decrease the amount of agonist available to signal, but also increase the relative antagonistic effects of ATP, because of less competition for the common receptor.

CD39-L2 and/or CD39-L4 may be involved in cancer cell generation, proliferation or metastasis. Detection of decreased levels of CD39-L2 or CD39-L4 polynucleotides or polypeptides may be useful for the diagnosis and/or prognosis of one or more types of cancer. For example, the decreased expression of CD39-L2 or CD39-L4 polynucleotide/polypeptide may indicate a hereditary risk of cancer, a precancerous condition, or an ongoing malignancy. A defect in the CD39-L2 or CD39-L4 gene may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions comprising CD39-L2 and/or CD39-L4 may be effective in adult and pediatric oncology including in endometrial cancer, malignant melanoma and myeloid leukemia.

Studies have shown that increased nucleotide phosphates, such as ATP and ADP, promote cell cycle progression through activation of P2Y2 receptors in endometrial tumor cells (Katzur et al., J. Clin. Endocrinol. Metab. 84: 4085–91, 1999) and less differentiated myeloid leukocytes have enhanced expression of endogenous nucleotides or decreased expression of ecto-nucleosidases (Clifford et al., Am. J. Physiol. 273: C973–87, 1997). In addition, increased ecto-ATPase activity, such as CD-39 activity, causes a decrease in tumor progression due to increased immunological recognition. (Dzhandzhugazyan et al., FEBS Lett. 430: 227–30, 1998). It may be that the ratio of nucleotide diphosphates to nucleotide triphosphates may promote tumor progression by increasing cellular proliferation and reducing immunological recognition of tumor cells. Therapeutic treatments which alter these nucleotide ratios, such as CD39-L2 or CD39-L4, may promote tumor regression.

CD39-L2 or CD39-L4 polypeptides, polynucleotides, or modulators (preferably CD39-L2 or CD39-L4 stimulators of enzymatic activity) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, increasing tumor cell immune recognition, or otherwise improving overall clinical condition, without necessarily eradicating the cancer.

The compositions can also be administered in therapeutically effective amounts as a portion of an anti-cancer cocktail. An anti-cancer cocktail is a mixture of CD39-L2 and/or CD39-L4 polypeptide or modulator with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine Sulfate.

In addition, CD39-L2 and/or CD39-L4 therapeutic compositions may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of CD39-L2 and/or CD39-L4 to reduce the risk of developing cancers.

In vitro models can be used to determine the effective doses of CD39-L2 and/or CD39-L4 as potential cancer treatments. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al., Clin. Exp. Metastasis, 17:423–9 (1999) respectively. Suitable tumor cells lines are available, e.g. from American Type Tissue Culture Collection catalogs.

The polypeptides of the invention are administered by any route that delivers an effective dosage to the desired site of action. The determination of a suitable route of administration and an effective dosage for a particular indication is within the level of skill in the art. For treatment of vascular disease, polypeptides according to the invention are generally administered intravenously. In vivo murine studies with soluble human CD39 have shown that mice injected intravenously with 50 mg recombinant soluble human CD39 in 100 ml sterile saline had biologically active CD39 in their sera for an extended period of time, with an elimination half-life of almost 2 days (Gayle, R. B., et al., J. Clinical Invest. 101:1851–1859 (1998)). Suitable dosage ranges for the polypeptides of the invention can be extrapolated from these dosages or from similar studies in appropriate animal models. Dosages can then be adjusted as necessary by the clinician to provide maximal therapeutic benefit.

6.18 Pharmaceutical Formulations and Routes of Administration

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin.

The pharmaceutical composition may further contain other agents which either enhance the activity of the protein or compliment its activity or use in treatment. For example, CD39-L2 or CD39-L4 may be co-administered with platelet ADP receptor antagonists, e.g. ATP derivatives, ADP derivatives. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

6.18.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

6.18.2. Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a progeny-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers maybe added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoroniethane, trichlorofluoromethane, dichlorotetrafluoroethiane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Attentively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

6.18.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1.Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time preferably between 30–90% and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

6.18.4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1

Isolation of SEQ ID NO:1 from a cDNA Library of Human Fetal Liver-Spleen

A plurality of novel nucleic acids were obtained from a 2HFLS20W cDNA library prepared from human fetal liver-spleen, as described in Bonaldo et al., Genome Res. 6:791–806 (1996), using standard PCR, Sequencing by hybridization sequence signature analysis. and Sanger sequencing techniques. The inserts of the library were amplified with PCR using primers specific for vector sequences flanking the inserts. These samples were spotted onto nylon membranes and interrogated with oligonleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. One of these inserts was identified as a novel sequence not previously obtained from this library and not previously reported in public databases. This sequence is shown in FIG. 1 as SEQ ID NO:1.

EXAMPLE 2

Isolation of SEQ ID NO: 2 and Determination of a Nucleotide Sequence Encoding a 428-Amino Acid Protein with Sequence Homology to CD39

The nucleotide sequence shown in FIG. 1, and labeled SEQ ID NO: 2, encodes the translated amino acid sequence SEQ ID NO: 3, which is shown in FIG. 2. The extended nucleotide sequence was obtained by isolating colonies generated from pools of clones from a human macrophage cDNA library (Invitrogen, Cat. # A550-25). Briefly, the macrophage cDNA library was plated on LB/Amp plates (containing 100 mg/ml ampicillin) at a density of about 40,000 colonies/plate. The colonies were lifted onto nitrocellulose filters and hybridized with a radiolabeled probe generated from the original clone (i.e., SEQ ID NO: 1).

That the identified clones corresponded to SEQ ID NOs: 1 and 2 was confirmed by using gene-specific primers (5'-GCTACCTCACTTCCTTTGAG-3' [SEQ ID NO: 9] and 5'-CTGGCTGGTGAAGTTTTCCTC-3' [SEQ ID NO: 10]) in a PCR-based assay. Then PCR using vector- and gene-specific primers was employed to amplify the 5' portion of the cDNA. Nested primers were used to generate sequence from the amplified product(s). Laser gene™ software was used to edit and "contig" the partial sequences into a full-length sequence. As discussed above, the amino acid sequence has striking homology to CD39, which is involved in modulating platelet reactivity during vascular inflammation. Based in part on the observed sequence similarity to CD39, the polypeptide encoded by SEQ ID NO: 2 was designated CD39-L4.

EXAMPLE 3

A. Expression of SEQ ID NOS. 3 and 5 in COS-7 Cells

COS-7 cells were grown in DMEM (ATCC) and 10% fetal bovine serum (FBS) (Gibco) to 70% confluence. Prior to transfection the media was changed to DMEM and 0.5% FCS. Cells were transfected with cDNAs for SEQ ID NOs. 3 and 5 or with pBGal vector by the FuGENE-6 transfection reagent (Boehringer). In summary, 4 µl of FuGENE-6 was diluted in 100 µl of DMEM and incubated for 5 minutes. Then, this was added to 1 µg of DNA and incubated for 15 minutes before adding it to a 35 mm dish of COS-7 cells. The COS-7 cells were incubated at 37° C. with 5% $CO_2$. After 24 hours, media and cell lysates were collected, centrifuged and dialyzed against assay buffer (15 mM Tris pH 7.6, 134 mM NaCl, 5 mM glucose, 3 mM $CaCl_2$ and $MgCl_2$. More robust expression can be achieved using the protocol described in Example 6 below.

B. Expression Study Using SEQ ID NO: 2

The expression of SEQ ID NO. 2 in various tissues was analyzed using a semi-quantitative polymerase chain reaction-based technique. Human cDNA libraries were used as sources of expressed genes from tissues of interest (adult brain, adult heart, adult kidney, adult lymph node, adult liver, adult lung, adult ovary, adult placenta, adult spleen, adult testis, bone marrow, fetal kidney, fetal liver, fetal liver-spleen, fetal skin, fetal brain, fetal leukocyte and macrophage). Gene-specific primers (5'-GCTACCTCACTTCCTTTGAG-3' [SEQ ID NO: 9] and 5'-GCAGGTCTCCAAGGAAGTACG-3' [SEQ ID NO: 11]) were used to amplify portions of the SEQ ID NO: 2 sequence from the samples. Amplified products were separated on an agarose gel, transferred and chemically linked to a nylon filter. The filter was then hybridized with a radioactively labeled ($\alpha^{33}$P-dCTP) double-stranded probe generated from the full-length SEQ ID NO: 2 sequence using a Klenow polymerase, random-prime method. The filters were washed (high stringency) and used to expose a phosphorimaging screen for several hours. Bands indicated the presence of cDNA including SEQ ID NO: 2 sequences in a specific library, and thus mRNA expression in the corresponding cell type or tissue.

Of the 18 human tissues tested, macrophage was the only sample that provided a signal, indicating that expression of SEQ ID NO: 2 is tightly regulated. In contrast, the CD39 molecule has been found in tissues such as placenta, lung, skeletal muscle, kidney and heart.

EXAMPLE 4

Chromosomal Localization of the Gene Corresponding to SEQ ID NOs:1 and 2

Chromosome mapping technologies allow investigators to link genes to specific regions of chromosomes. Assignment to chromosome 14 was performed with the Coriell cell repository monochromosomal panel #2 (NIGMS cell repository). This human rodent somatic cell hybrid panel consists of DNA isolated from 24 hybrid cell cultures retaining 1 human chromosome each. The panel was screened with gene-specific primers (5'-GCTACCTCACTTCCTTTGAG-3' [SEQ ID NO: 9] and 5'-CTGGCTGGTGAAGTTTTCCTC-3' [SEQ ID NO: 10]) that generated a sequence tag site (STS). The Genebridge 4 radiation hybrid panel was also screened (Research Genetics), and the results of the PCR screening were submitted to the Whitehead/MIT Radiation Hybrid mapping email server at http://www-genome.wi.mit.edu.

EXAMPLE 5

Platelet Aggregation Assay

Blood is anticoagulated with 0.1 volume 3.2% sodium citrate. Platelet-rich plasma (PRP) is prepared with an initial whole blood centrifugation (200×g, 15 min., 25° C.) and a second centrifugation of the PRP (90×g, 10 min.) to eliminate residual erythrocytes and leukocytes. The stock suspension of PRP is maintained at room temperature under 5% $CO_2$-air. The platelet aggregation assay uses a two-sample, four-channel Whole Blood Lumi-Aggregometor, model 560 (Chronolog Corp., Havertown, Pa.). PRP containing 1.22× $10^8$ platelets is preincubated with the sample to be tested for inhibition of aggregation for 10 min. at 37° C. in a siliconized glass ctivette containing a stirring bar, followed by stimulation with either ADP (5 mm), collagen (5 mg/ml), or thrombin (0.1 unit/ml). Platelet aggregation is recorded for at least 10 min. Data are expressed as the percentage of light transmission with platelet-poor plasma equal to 100%.

EXAMPLE 6

Expression and Characterization of CD39-L4 as a Soluble Apyrase

The mammalian ectoapyrase CD39 is an integral membrane protein with two transmembrane domains (one at each end of the protein) (Maliszewski, C. R. et al., J. Immunol. 153:3574–3583). The hydrophobicity profiles for the deduced amino acid sequence of other family members, such as CD39L1 and CD39L3, are very similar to CD39 (Chadwick, B. P. and Frischauf A. M., Genomics 50:357–367), suggesting that these proteins also have two membrane spanning domains. However, CD39-L4 does not appear to have a second transmembrane domain at its C-terminus, suggesting that the N-terminus hydrophobic region could code for a secretory signal. To test this hypothesis, CD39-L4 was subcloned into the mammalian expression vector pCDNA3.1 and a 6-Histidine tag was inserted into the coding sequence.

The CD39-L4 cDNA sequence was initially isolated from a macrophage cDNA library (Invitrogen). The sense primer (5'-TTAAAGCTTGGGAAAAGAATGGCCACTTC-3', SEQ ID NO. 20) with a HindIII site and the antisense primer (5'-AGACTCGAGGTGGCTCAATGGGAGATGCC-3', SEQ ID NO. 21) with a XhoI site were used to subclone the coding sequences into the mammalian expression vector pCDNA3.1 (Invitrogen). The nucleotide sequence of the insert is set forth in SEQ ID NO. 4. In order to immunologically detect the protein, the coding region was further modified so that it would include a Gly-Ser-6His epitope tag immediately following $Arg^{24}$. Briefly, two partially overlapping complementary oligonucleotides (5'-GCGCTGTCTCCCACAGAGGATCGCAT-CACCATCACCATCACAACCAGCAG ACTTGGTT-3' (SEQ ID. NO. 22) and 5'-AACCAAGTCTGCTGGTTGTGATGGTGATGGTG ATGCGATCCTCTGTGGGA GACAGCGC-3' (SEQ ID NO. 23)) were used on the CD39-L4 pCDNA3.1 template. The primers were extended in opposite directions around the plasmid using a 12 cycle PCR program (95° C., 1 minute; 60° C., 1 minute; 72° C., 15 minutes) (Stratagene). The reaction was treated with DpnI to digest the methylated parental DNA and then transformed into E. coli. Colonies were screened for the insert.

A. Expression in COS Cells and Cellular Localization of CD39-L4

To ascertain whether CD39-L4–6His is secreted, the coding region of the CD39-L4–6His protein was inserted into the pcDNA3.1 expression vector and transiently transfected into COS-7 cells. COS-7 cells obtained from the American Tissue Type Culture Collection were grown in DMEM supplemented with 10% FBS and 100 units/ml penicillin G and 100 µg/ml streptomycin sulfate at 37° C. in 10% $CO_2$. Transfections were performed at 75% confluency in 10 cm plates with Fugene-6 (Roche) according to the manufacturers instructions. The cells in 7 mls of medium were incubated with 16 µl of Fugene-6 and 8 µg of DNA for 14–18 hours. At the end of the transfection the medium was replaced with DMEM medium containing low serum (1% FBS). The cells were then incubated for 24–48 hours prior to harvesting.

The CD39-L4–6His was concentrated by treating the cell lysates and medium with Nickel-NTA agarose (Qiagen) followed by SDS/PAGE and immunoblot analysis with an antibody against the Arg-Gly-Ser-6His epitope. Cells were washed twice with PBS containing 0.5 µg/ml leupeptin, 0.7 µg/ml pepstatin and 0.2 µg/ml aprotinin. After a brief sonication and centrifugation step to clear the lysate, the samples were then incubated with a Nickel-NTA resin at 4° C. for 2–3 hours. The histidine-tagged protein complexed to the resin was washed three times with PBS before loading onto a 10% SDS/PAGE gel for Western blot analysis. CD39-L4 was detected in both the cell lysate and the medium from cells transfected with the CD39-L4–6His expression vector, but not from control cells. While the predicted molecular weight of CD39-L4–6His is 46 kDa, the immunoreactive protein exhibited a mobility by SDS/PAGE corresponding to a molecular mass of approximately 51 kDa in the media and approximately 48 kDa in the cell lysate. The difference in apparent molecular weight may be due to posttranslational medications of three potential N-glycosylation sites in the CD39-L4 predicted amino acid sequence.

B. Secretion of CD39-L4

Secretion of CD39-L4 was also examined by treatment of the transfected cells with brefeldin A, an inhibitor of translocation of secretory proteins from the endoplasmic reticulum to the Golgi apparatus. Chadwick, et al., Genomics 50:357–367 (1998). Brefeldin A was dissolved in ethanol and added to the transfected cells 48 hours after transfection. Both control and brefeldin A treated cells were washed once with PBS and incubated for 8 hours in medium with none or varying dosages of brefeldin A. Increasing dosages of brefeldin A blocked secretion of CD39-L4–6His and led to massive intracellular accumulation.

In addition, the secreted 6His tagged protein was isolated from media as described above using Nickel-NTA agarose (Qiagen) and subjected to SDS-PAGE under both reducing and nonreducing conditions. Western blot analysis with antibody against the Arg-Gly-Ser-6His epitope showed that under nonreducing onditions the mobility of the protein was twice as slow as the reduced monomeric form. Thus, the secreted CD39-L4 is composed of disulfide-bonded dimers. It is also possible that selected CD39-L4 is composed of other higher oligomeric forms generated by noncovalent interaction of dimeric forms.

C. CD39-L4 Expression in a Stable Human 293 Cell Line

CD39-L4 was also expressed in human embryonic carcinoma 293 cells obtained from the American Type Culture Collection as follows. The 293 cells were grown in DMEM/F12 media supplemented with 10% FBS and 100 units/ml penicillin G and 100 µg/ml streptomycin sulfate at 37° C. in 10% $CO_2$. Transfections were performed at 60% confluency in a 10-cm plate with Fugene-6 (Roche) according to the instructions of the manufacturer. Briefly, the cells in 8 ml of medium were incubated with 16 µl of Fugene-6 and 4 µg of CD39L4-$His_6$ pcDNA3.1. After 20 hours the cells were transferred to T-150 flask and the medium was replaced with 293 media containing 800 µg/ml Geneticin (G418, Life Technologies Inc.). The cells were fed every two days with selection medium for 20 days.

D. Purification and Molecular Mass of CD39-L4

Low serum media (1% FBS) from a 293 stable transfected cell line or transiently transfected COS-7 cells was collected and centrifuged to clear any cell debris. Protease inhibitors (0.5 ug/ml leupeptin, 0.7 ug/ml pepstatin and 0.2 ug/ml aprotinin) were added to the media before purification through a Nickel-NTA column (Qiagen). The column was washed with 10-column volumes of PBS buffer and the protein eluted with 0.1 M sodium acetate, pH4.5 and 0.3 M NaCl. The eluted protein was collected as fractions and neutralized with TrisHCl, pH9 added to a final concentration of 70 mM. The fractions with most ADP activity were pooled and concentrated further with Microcon concentrators (Millipore).

This purified CD39L4 protein was subjected to ultracentrifugation in a 5–15% sucrose density gradient and the sedimentation of CD39L4 protein was compared with that of marker proteins of known native molecular weights to determine its molecular weight. The centrifugation studies using a sucrose gradient were done in a Backman L8-M (Fullerton, Calif.) ultracentrifuge equipped with a SW 41 rotor. Samples were centrifuged at 39,000 rpm for 15 h at 4° C. without using the brake. The protein was layered on top of a 5–15% (w/v) sucrose density gradient (10 ml) in 10 mM Tris pH 7.5, 150 mM NaCl and 5 mM $CaCl_2$. Individual fractions were then collected from the bottom of the tube and processed for activity assays. Western blot, coomassie staining and refractive index measurements. The mass of CD39L4 was estimated by comparison of its mobility with those of standard proteins.

Most of the CD39L4 activity was observed in the 7.25% region of the sucrose gradient located between the 55 kDa and 29 kDa markers. The peak of CD39L4 immunoreactivity also coincided with the peak of activity yielding an estimated molecular mass of approximately 50 kDa. The peaks of activity and immunoreactivity while in close agreement were not fully symmetrical because there was a small amount of protein sedimenting at a higher sucrose concentration of between 8–9.5%. A Western blot of these fractions showed that they were enriched for dimers although not fully devoid of monomers. Matching the ADPase activities of fraction #17 (9.4% sucrose) and fraction #27 (7.0% sucrose) first, and then comparing the relative amounts of protein by immmunoblotting revealed that the amount of monomeric CD39L4 equaled each other in the two fractions.

Comparable amounts of ADPase activity from monomer and dimer enriched fractions from the sucrose density gradients demonstrated that the dimer does not possess any significant level of enzymatic activity. It is possible that the monomer is the active form of the protein and that the dimer either represents an inactive form or is a by-product of the oxidation of the odd-numbered cysteine residues found in CD39L4. CD39L4 appears to be unique in that its monomeric form has higher enzymatic activity than its dimeric form.

E. CD39-L4 Expression in Insect Cells

CD39-L4 was expressed in insect cells as follows. The cDNA was cloned into the insect expression vector pIZ/V5-His (Invitrogen). Briefly, the CD39-L4–6His cDNA in the pcDNA 3.1 vector described above in Example 6 was cut with HindIII and XhoI and the cDNA insert was inserted in pIZ/V5-His cleaved by HindIII/XhoI. The resulting vector was transiently transfected into insect High Five cells (Invitrogen). High Five cells were grown in serum-free High Five media (Invitrogen) at 27 ° C. Transfections were performed at 50–60% confluency in a 6-cm plate with Insectin-Plus liposomes (Invitrogen) according to Invitrogen's protocol. The cells were incubated with 20 μl of Insectin-Plus liposomes and 1 ml of High Five serum-free medium for 15 minutes. The cells were then incubated with 10 μg of DNA for four hours at room temperature. At the end of the transfection, 2 mls of fresh media were added and the cells were incubated for another 48 hours before transferring to 96-well plates containing 400 μg/ml Zeocin (Invitrogen). After three weeks of selection the insect cell media was assayed for the secreted protein by Western blot of a slot blot. The highest overproducing clone was rescreened by immunoblotting analysis of media separated on a 10% SDS-polyacrylamide gel.

CD39-L4 was isolated from the insect media by treating with Nickel-NTA agarose (Qiagen) and tested for ADPase activity by measuring inorganic phosphate release as described in Example 9 below. The activity of the recombinant insect CD39-L4 was comparable to that of the mammalian CD39-L4 expressed from COS-7 cells as described in Example 6. However, the insect CD39-L4 appears to be monomeric and under nonreducing conditions migrates with the monomeric form of mammalian CD39-L4.

The affinity purified mammalian derived protein (see section D) or media samples from High Five cells expressing CD39-L4 were separated by SDS-polyacrylamide gel (10%) electrophoresis under reducing (143 mM beta-mercaptoethanol) or non-reducing conditions. The proteins were transferred onto the Immobilon-P (Millipore) membrane and incubated with a CD39L4 specific antibody prepared as described in Example 18A below (1:2000) and with a horseradish peroxidase-conjugated anti-mouse antibody (Pierce). The bands were visualized using a chemiluminescent reagent (ECL, Amershan Pharmacia).

Although the predicted molecular mass is 46 kDa, the mammalian protein (see section D) was expressed as a major species with a mobility of around 51 kDa. This shift in mobility is most likely due to glycosylation, as incubation of the protein with peptide N-glycosidase F (PNGase F) results in a mobility shift to around 46 kDa. Interestingly, under non-reducing conditions a second species was also detected with a mobility of around 110 kDa when fully glycosylated and around 100 kDa when deglycosylated. These higher molecular weight species could correspond to dimers held together via a disulfide linkage.

When protein was expressed in High Five insect cells, the recombination protein was detected as a major band of approximately 46 kDa in the culture medium, indicating that CD39L4 is efficiently secreted. The observed molecular mass of recombinant CD39L4 was in very close agreement to that of the deglycosylated mammalian protein. A minor band was also detected at around 100 kDa which could correspond to dimers. The recombinant protein was also treated with PNGase F but no change in mobility was observed, demonstrating that the secreted CD39L4 protein is not glycosylated to the same extent as that of the protein secreted from 293 cells. Reduction of the disulfide bonds resulted in the disappearance of the 100 kDa species. The underglycosylated recombinant protein isolated from insect cells also demonstrated comparable relative activity to the fully glycosylated mammalian protein.

EXAMPLE 7

Assay for ATPase Activity

Apyrase activity was determined by measuring the amount of $[^{33}P]P_i$ released from $[\gamma^{33}P]ATP$. In summary, 50 μl of samples were incubated in the presence of 10 μCi of $[\gamma^{33}P]ATP$ for one hour at 37° C. The $[^{33}P]P_i$ released and the $[\gamma^{33}P]ATP$ were separated by thin layer chromatography (TLC) plates (EM Science). The solvent system consisted of 1 M $KH_2PO_4$. The separated compounds were scanned for radioactivity with a Phosphoimager (Molecular Dynamics, Sunnyvale, Calif.) and quantitated by ImageQuant software. COS-7 cells transfected with SEQ ID NOs. 3 and 25 had at least a four fold increase in activity over cells transfected with the vector alone. Although ATPase activity was present, Example 13 demonstrates that CD39-L4 has significantly more NDPase activity.

EXAMPLE 8

Site-directed Mutagenesis of CD39L4

Site directed mutagenesis was employed to increase the enzymatic activity of CD39L4. Amino acid sequence comparisons between CD39 family members reveal four highly homologous regions in all five human members (Chadwick and Frischauf, Genomics 50:357–367, 1998). These regions, termed apyrase-conserved regions (ACRs), are present not only in the CD39 family members but other apyrases from species as distant as yeast and plants. Examination of similarities and differences in the CD39 ACRs led to the design of three CD39L4 mutants (see FIG. 5). In these mutants, codons encoding CD39 ACR specific residues were used to replace codons from the CD39L4 wild type ACR sequence. Only residues with significantly different structural or chemical properties were replaced. A PCR based approach was used to produce these mutations.

Briefly, the expression vector pcDNA3.1 (Invitrogen) containing the full coding sequence of the CD39L4 gene (with a 6 Histidine tag inserted after Arg 24 in the coding sequence to allow purification of the secreted mature form of the protein) was subjected to a PCR-based site-directed mutagenesis approach using overlapping oligonucleotides [CD39-L4 ACR I mutant (nt 177–148 and 160–204): 5'-GTG AGT GCT CCC TGC ATC TAA CAT AAT TCC-3' (SEQ ID NO: 12) and 5'-GAT GCA GGG AGC ACT CAC ACT AGT ATT CAT GTT TAC ACC TTT GTG-3' (SEQ ID NO: 13); CD39-L4 ACR II mutant (nt 402–359 and 385–415): 5'-GCG TAG TCC TGC TGT TGC CCC TAG GTA CAC TGG GGT CTT TTT CC-3' (SEQ ID NO: 14) and 5'-GCA ACA GCA GGA CTA CGC TTA CTG CCA GAA C-3' (SEQ ID NO: 15); and CD39-L4 ACR III mutant (nt 532–485 and 513–540): 5'-CCC AAG CGA ATA TGC CTT CGT CTT GTC CAG TCA TGA TGC TAA CAC TGC-3' (SEQ ID NO: 16) and 5'-CGA AGG CAT ATT CGC TTG GGT TAC TGT G-3' (SEQ ID NO: 17)]. After amplification of the whole plasmid with Pfu DNA polymerase (Stratagene) (95° C./1 min; 60° C./1 min; 72° C./15 min for 12 cycles), the methylated parental DNA was digested with the restriction enzyme DpnI, leaving only the unmethylated PCR amplified products. The resulting annealed double-stranded nicked products were then transformed into bacteria and the resulting colonies were screened for the desired mutations by sequencing. The subsequent constructs were fully sequenced to verify that the mutations were in fact introduced and that no extraneous mutations were generated.

EXAMPLE 9

ACR III Mutant Increases ADPase Activity

Plasmids containing the mutated and wild type forms of the CD39L4 gene were transfected into COS-7 cells. After two days, protein was purified from the culture medium using a Nickel-NTA resin approach to concentrate the tagged proteins. These proteins were then assayed for ATPase and ADPase activity by measuring the inorganic phosphate released (Wang, T. F., et al., J. Biol. Chem. 273:24814–24821, 1998). The proteins were incubated in apyrase buffer (15 mM Tris pH 7.4, 135 mM NaCl, 2mM EGTA and 10 mM glucose) for 1 hour at 37 ° C. with or without 2 mM $CaCl_2$ or 2 mM $MgCl_2$. Phosphatase reactions were initiated by the addition of ADP or ATP to a final concentration of 1 mM. The reaction of inorganic phosphorus with ammonium molybdate in the presence of sulfuric acid, produces an unreduced phosphomolybdate complex. The absorbance of this complex at 340 nm is directly proportional to the inorganic phosphorus concentration (Daly, J. A., and Ertingshausen G., Clin. Chem. 18:263 (1972) (Sigma Diagnostics)).

As seen in FIG. 7, mutations in ACR I and II eliminate activity, whereas the mutations in ACR III increase activity six-fold over wild type. The increased ADPase activity over wild type is due to a corresponding increase in the amount of protein and not to an increase in the specific activity of the enzyme. Western blots using antibody against the Arg-Gly-Ser-6His epitope of 6His ACRIII compared to 6His wildtype CD39-L4 isolated on Nickel-NTA showed that recombinant expression of ACRIII in COS-7 cells was approximately 6-fold higher than expression of the wildtype protein. Therefore, the mutant protein appears to be synthesized at a higher level than the wild type protein in COS-7 cells. The replacement of three amino acids in the III region (amino acids 167 to 181 in CD39-L4) and the resulting increase in ADPase activity or expression predicts that replacement of additional amino acids within this region by amino acids from the equivalent region of CD39 may also enhance the activity or expression of the protein over wild type CD39L4. The increase in ADPase activity or expression over wild type may also be due to the replacement of only one or two of the three amino acids; this can be confirmed by replacing one or two amino acids at a time. In addition, changing the nucleotide sequence by making silent codon changes at the same position without affecting the amino acid sequence may also result in increased expression or enzyme activity.

The polynucleotide and amino acid sequences of a CD39-L4 variant termed ACRIII and having the amino acid substitutions D168→T, S170→Q and L175→F compared to wild type CD39-L4 (SEQ ID NO: 5) are set forth in SEQ ID NOs: 6 and 7, respectively, and in FIG. 6.

EXAMPLE 10

ACR III Mutant and Wild Type Forms are Specific for ADP and not ATP

Both the CD39L4 wild type and the CD39L4 variant with mutations in the ACRIII region hydrolyze ADP. However, when ATP was tested as a substrate, neither the CD39L4 nor the CD39L4 mutant, ACR III, catalyzed hydrolysis. In contrast, CD39 as a membrane bound molecule (Marcus, et al., The Journal of Clinical Investigation, 99: 1351–1360) or as a genetically engineered soluble form (Gayle, et al., The Journal of Clinical Investigation, 101:1851–1858, 1998) is able to hydrolyze both ATP and ADP substrates efficiently. The specificity that both CD39L4 wild type and the CD39L4 ACR III mutant have for ADP is an advantageous feature that makes these CD39L4-type molecules better antiplatelet therapeutic candidates than CD39, as ADP is the agonist that causes platelet aggregation. Therapeutics that have both ADPase and ATPase activities potentially could create adverse side effects by interfering with levels of ATP in the circulation.

EXAMPLE 11

Organization of the Human CD39-L4 Gene

A human CITB BAC genomic library (Research Genetics) was screened with gene specific primers [246–16 (nt 5522–5543), 5 '-CTTCCTTCACTGGGAATTCAGG-3' (SEQ ID NO: 18) and 246-K4 (nt 4922–4945), 5'-CTGTTTACCGAGATGGTTGGAAGC-3' (SEQ ID NO: 19)] using a PCR based assay.

Briefly, gene specific primers were used to screen pools of BAC DNAs. BAC pools that produced an amplified DNA fragment of the predicted size were pursued until an individual BAC was identified. BAC63–118 was isolated and the CD39-L4 gene sequenced mainly by subcloning PCR amplified regions with gene-specific primers and intron-specific primers, and to a lesser extent by direct sequencing of BAC DNA. The partial sequence is set forth in SEQ ID NO: 8. The CD39-L4 coding sequence was found to be distributed over 14 exons spanning 15 kb of genomic DNA as set out in SEQ ID NO: 42; exons appear at nucleotides 245–461, 1454–1533, 2734–2877, 4364–4439, 4679–4714, 5326–5414, 5723–5802, 6751–6812, 7758–7859, 8712–8852, 9831–9887, 10383–10498, 11916–12002 and 14472–14526. The last two exons are differentially spliced, producing either CD39-L4 or CD39-L66.

EXAMPLE 12

CD39-L4 and CD39-L2 are Stimulated by Divalent Cations

The high degree of conservation in the apyrase conserved regions of CD39-L4 and CD39-L2 suggests similar function to other apyrases. To test this hypothesis, COS-7 cells were transfected with the CD39-L4–6His and CD39-L2myc-His construct as described herein. The medium from transfected cells was incubated with Nickel-NTA resin (Qiagen) in order to capture the 6His tagged protein, the resin was washed with assay buffer (buffer A: 15 mM Tris pH 7.5, 134 mM NaCl and 5 mM glucose) and the protein still tethered to the resin in a suspension was assayed for ADPase activity. Nucleotidase activity was determined by measuring the amount of inorganic phosphate released from nucleotide substrates using the technique of Dlay and Ertingshausen, Clin. Chem. 18:263–265 (1972). In this reaction the complex of inorganic phosphorus with phosphor reagent (ammonium molybdate in the presence of sulfuric acid) produces an unreduced phosphomolybdate compound. The absorbance of this complex at 340 nm is directly proportional to the inorganic phosphorus concentration. The protein still tethered to the resin as a 30% (50% for CD39-L2) suspension in buffer A was assayed by the addition of the nucleotide to a final concentration of 1 mM and incubated at 37° C. for 30 minutes. The reaction was stopped by adding 100 volumes of phosphor reagent. The amount of phosphate released from the reaction was quantified using a calcium/phosphorus combined standard (Sigma). The amount of protein used in the assays was estimated by comparing the intensity of the bands in Western blots with that of a series of standards of known quantity. CD39-L4 protein from transfected cells displayed a 2.3 fold increase in activity over the cells transfected with the vector alone. When $Ca^{2+}$ and $Mg^{2-}$ were added, the activity increased 3.6 fold and 6 fold, respectively. CD39-L2 protein from transfected cells displayed an 8.7 fold increase in activity over the cells transfected with the vector alone. When $Ca^{2+}$ and $Mg^{2-}$ were added, the activity of the CD39-L2 cells increased another 2–3 fold.

EXAMPLE 13

Characterization of CD39-L4 Activity

CD39-L4 protein was assayed for ADPase activity in the presence of different kinds of inhibitors of ADPases. Control ecto-apyrase activity was determined with protein tethered to the Nickel-NTA resin. Both assays were performed as described above except the protein was in buffer A containing 2 mM $CaCl_2$ and 2 mM $MgCl_2$. As shown by Table 1 below, inhibitors of phosphatases ($F^-$) and adenylate kinase (Ap5A) did not inhibit activity. The inhibitors of vacuolar ATPases (NEM), mitochondrial ATPases (N3$^-$) and Na$^+$, K$^+$, ATPase (ouabain) did not significantly inhibit the $Ca^{2+}$ and $Mg^{2+}$ stimulated activity. However, metal chelators (EDTA and EGTA) significantly inhibited activity. These results show that the overwhelming majority of the activity in the assays originates from a protein bound to the resin with characteristics of an E-type apyrase.

TABLE 1

Inhibition of CD39-L4 activity

| INHIBITORS | % OF CONTROL |
|---|---|
| Control | 100 ± 7 |
| Ouabain (1 mM) | 96 ± 6 |
| NEM (10 mM) | 106 ± 5 |
| N3 (1 mM) | 100 ± 12 |
| F (10 mM) | 113 ± 5 |
| Ap5A (10 μM) | 121 ± 9 |
| EGTA (2 mM) | 35 ± 3 |
| EDTA (2 mM) | 52 ± 3 |

As shown in Table 2 below, the nucleotide specificity of CD39-L4 was also assayed as described above. The CD39-L4 activity was determined with protein tethered to the Ni-NTA resin. The protein was in buffer A containing 1 mM EGTA, as well as 2 mM $CaCl_2$ and $MgCl_2$. The assay was started by adding the nucleotides to a final concentration of 1 mM. The values below are expressed relative to ADP. The relative activity of the nucleotide triphosphates varies almost seven-fold with ATP being the poorest substrate. No phosphate release was detected with AMP and ADP was hydrolyzed at a rate approximately twenty-fold higher than ATP. The other nucleotide diphosphates (GDP and UDP) were also very efficiently hydrolyzed by CD39-L4. These results indicate that CD39-L4 defines a new class of E-type apyrase in humans with a specificity for NDPs as enzymatic substrates.

TABLE 2

Substrate specificity of CD39-L4

| NUCLEOTIDE | % OF CONTROL |
|---|---|
| ADP | 100 ± 15 |
| ATP | 5 ± 1 |
| AMP | 0 |
| CTP | 26 ± 2 |
| GTP | 34 ± 1 |
| UTP | 12 ± 4 |
| CDP | 268 ± 11 |
| GDP | 334 ± 38 |
| UDP | 408 ± 14 |

B. Determination of Kinetic Characteristics of CD39L4 ADPase Hydrolysis

The determination of kinetic parameters for ADP hydrolysis was carried out in buffer A in the presence of 15 mM $CaCl_2$, 1 mM ouabain, 10 mM NEM, 10 μM Ap5A and concentrations of ADP varying from 0.75 mM to 18 mM, at 37° C. for 15 min. The reaction was stopped by adding 100 volumes of phosphorus reagent (Sigma). The amount of phosphate released from each reaction was quantitated by comparing the absorbance at 340 nm with that of a Calcium/Phosphorus standard (Sigma).

The rate of product release was found to be linear within the first 20 minutes of reaction, therefore the initial velocity $V_o$ was taken to be the rate of reaction over the first 15 minutes. $V_o$ was determined over a range of ADP concentrations, and each data point represents an average of 3 separate experiments. Curve-fitting of the Michaelis-Menton Equation $\{V_o=(V_{max}[S])/(K_m+[S])\}$ to the data points was performed by DeltaGraph® 4.0 software (SPSS Inc., Chicago, Ill.) resulted in an $R^2$ Value equal to 0.994. The $V_{max}$=1191 pmol/min and $K_m$=12.7 mM were also calculated.

The amount of CD39L4 protein in each reaction was found to be 60 ng and by assuming a molecular weight of 46000 g/mol for CD39L4 protein, the turnover number, $k_{cat}$ of CD39L4 with ADP as a substrate was determined to be 913/min.

The kinetic data for CD39L4 shows a $K_m$ value in the millimolar range for ADP. However, levels of ADP in the circulation appear to be in the low micromolar range. This suggests that CD39L4 would be effective in quenching a sudden rise in the levels of ADP in situations such as platelet activation, wherein the intracellular levels of ADP could be secreted rapidly to levels optimal for CD39-L4 hydrolysis. Dense granules inside platelets have been shown to contain high concentrations of ADP, estimated to be up to 0.5 M. Interestingly, as described in Example 17 below, CD39-L2 also exhibits a similar $K_m$ value indicating a potential overlapping function for these two enzymes.

EXAMPLE 14

Glycosylation is not Essential for CD39-L4 Activity

The cDNA encoding CD39L4 predicts three potential N-glycosylation sites. Post-translational modifications such as N-linked glycosylation are common in secreted and membrane-bound mammalian proteins. These modifications may be important for correct protein folding or enzymatic activity and are not easily reproduced when the proteins are expressed in other organisms such as bacteria. In order to test whether CD39-L4 is glycosylated, COS-7 cells, transfected as described in Example 6, were treated with tunicamycin (Sigma), which blocks the formation of N-glycosidic linkages.

COS-7 cells were grown to 75% confluency and transfected with the CD39-L4–6-His construct. After 24 hours, a traction of the COS-7 cells were treated with Tunicamycin at a concentration of 5 μg/ml. The media was replaced again after 24 hours with fresh tunicamycin and harvested after 48 hours. The CD39-L4–6His protein was concentrated by treating the media with Nickel-NTA agarose (Qiagen). The resin was washed with assay buffer and the protein still tethered to the resin in a suspension was assayed for a shift in electrophoretic mobility as well as its ADPase activity.

Western blot analysis using an antibody against the 6-His epitope revealed that the glycosylated CD39-L4 protein isolated from the control cells had an approximate size of 51 kDa. However, tunicamycin treated cells had a molecular weight of approximately 46 kDa indicating that the protein was deglycosylated.

ADPase activity of the tunicamycin treated cells was assayed as described in Example 12 above. The deglycosylated CD39-L4 protein had ADPase activity comparable to an equal amount of the glycosylated protein isolated from control cells. This demonstrates that glycosylation of the protein is not important for ADPase activity.

As described in Example 6E above, treatment of the recombinant protein with peptide N-glycosidase F also resulted in a shift in electrophoretic mobility, confirming glycosylation of the protein.

As shown here and in Example 6, neither dimer formation nor glycosylation appeared to contribute significantly to the ADPase activity of CD39L4, indicating that expression of an active recombinant CD39-L4 product in E. coli is possible.

EXAMPLE 15

A. Cloning and Expression of CD39-L2

The CD39-L2 coding sequence (SEQ ID NO: 26) was subcloned into pcDNA3.1/myc-His(+)A (Invitrogen) via the EcoRI and XbaI sites. Briefly, a human adult heart cDNA library (Gibco BRL) was subjected to polymerase chain reaction (PCR) using gene-specific primers L2–5'B (5'-CGTATCCCGCGGGTGGAGGCCGGGGTG-3', SEQ ID NO: 28) and L2–3'B (5'-CTTCTGCAAGCCCAGAGCCAGTGTGC-3', SEQ ID NO: 29). The resulting products were diluted 100-fold and subjected to a second round of PCR with primers L2–5'A (5'-GGAGCCCAAAAGACCGGCTGC-3', SEQ ID NO: 30) and L2–3'A (5'-TGAAGTCACGTCCAGGACAGG-3', SEQ ID NO: 31). The product represented a single band by agarose gel and was purified and sequenced to confirm its identity. Primers corresponding to the translational start region and the carboxy terminal region, excluding the stop codon, of the CD39-L2 coding sequence, L2EcoMet (5'-CGGAATTCAACATGAAAAAAGGTAATCCGTTA TGAA-3', SEQ ID NO: 32) and L2Xba3' (5'-TGTCTAGATGAGGCTGGACTCTTCTG-3', SEQ ID NO: 33) were used on the purified DNA to produce a DNA fragment corresponding to the entire coding region of the CD39-L2 gene, flanked by EcoRI and XbaI sites. This PCR product was digested to generate overhang ends that were ligated into the EcoRI and XbaI sites of pcDNA3.1/myc-His(+)A. The resulting plasmid allowed expression of the CD39-L2 coding sequence fused in frame with the myc-6His epitope at the carboxy terminus.

Transfection of COS-7 cells was performed as described below. COS-7 cells obtained from the American Tissue Type Culture Collection were grown in DMEM supplemented with 10% FBS and 100 units/ml penicillin G and 100 μg/ml streptomycin sulfate at 37° C. in 10% $CO_2$. Transfections were performed at 75% confluency in 10 cm plates with Fugene-6 according to the manufacturer's instructions. The cells in 10 ml of medium were incubated with 16 μl of Fugene-6 and 4 μg of DNA for 48 hours. The medium was then replaced by DMEM containing low serum (1% FBS) or serum-free DMEM and incubated for 48 hours before harvesting.

After collecting the conditioned media from the transfected COS cells, cells were washed twice with PBS and then scraped from plates. Upon centrifugation the cells were resuspended in PBS containing 0.5 μg/ml leupeptin, 0.7 μg/mL pepstatin and 0.2 μg/mL aprotinin. After a brief sonication, the cytosolic fraction was separated from the insoluble membrane fraction by centrifugation and protein purified from the cytosolic fraction generally as described above for CD39-L4. For purification of proteins from the conditioned media, the media was centrifuged initially to clear any cell debris, adjusted to contain 6 mM sodium phosphate, pH 7.6, 0.5 μg/mL leupeptin, 0.7 μg/mL pepstatin and 0.2 μg/mL aprotinin, and incubated at 4° C. for 2–3 hours with 100 μL of Ni-NTA resin/10 mL of medium. The Ni-NTA resin was washed twice with Tris wash buffer (50 mM Tris HCl, pH 7.5, 300 mM NaCl and 5 mM imidazole), followed by 3 washes with apyrase assay buffer (15 mM Tris HCl, pH7.5, 134 mM NaCl and 5 mM glucose) and resuspended in a 50% suspension in the same buffer.

B. Tissue-specific Expression of CD39-L2

The expression of CD39-L2 in various tissues was analyzed using both a semi-quantitative polymerase chain reaction and a Northern blot analysis. For the PCR-based analysis, human cDNA libraries (brain, heart, kidney, lung, spleen, testis, fetal brain [SUPERSCRIPT™ cDNA libraries from Gibco BRL]; lymph node, placenta, bone marrow, leukocyte, stimulated leukocyte [MATCHMAKER cDNA libraries from CLONTECH Labs, Palo Alto, Calif.]; and ovary, fetal liver, macrophage [Invitrogen]) were used as sources of expressed genes from tissues of interest. Plasmid DNA (20 ng) from each library was used as template for PCR amplification. CD39-L2 gene-specific primers (5'-CGTATCCCGCGGGTGGAGGCCGGGGTG-3' (SEQ ID NO. 28) and 5'-CTTCTGCAAGTCCCAGAGCCAGTGTGC-3' (SEQ ID NO. 24)) were used to amplify a 1736 nt portion of the CD39-L2 mRNA sequence. Primers specific to human β-actin gene (5'CGGGATCCCTGTGCTACGTCGCCCTGGAC-3' (SEQ ID NO. 38) and 5'-CGGAATTCACTGGCGCAGGCGGTGATCTCCTT-3' (SEQ ID NO. 39)) were used to amplify a 315 nt fragment of the gene to serve as positive control for the cDNA libraries. The PCR conditions were as follows: 96° C. for 2.5 minutes (1 cycle); 96° C. for 45 seconds, 60° C. for 45 seconds, and 72° C. for 2.5 minutes (3 cycles); 94° C. for 30 seconds, 60° C. for 30 seconds and 72° C. for 2.5 minutes (30 cycles); and 72° C. for 6 minutes (1 cycle). Amplified products were separated on a 1.2% agarose gel. Out of 15 libraries tested, only adult heart and fetal brain yielded bands. The bands were sequenced to confirm primer specificity. The heart derived product encodes the functional CD39-L2 sequence that has been demonstrated to possess ADPase activity. The fetal brain-derived product represents a variant with 43 bp of additional sequence added to exon 14, resulting in a frame shift of the last 260 bp of coding sequence (SEQ ID NO: 45).

Other splice variants have also been identified in adult brain, adult bladder, adult rectum and adult mammary gland (SEQ ID NO: 46), adult brain, umbilical cord, adult thymus and adult mammary gland (SEQ ID NO: 47), adult brain (SEQ ID NO: 48), adult brain (SEQ ID NO: 49), adult brain, adult bladder, adult thymus, adult mammary gland, adult kidney, lung tumor, adult adrenal gland and adult thalamus (SEQ ID NO: 50), adult adrenal gland (SEQ ID NO: 51), adult colon and adult thymus (SEQ ID NO: 52), fetal lung (SEQ ID NO: 53), and adult thymus (SEQ ID NO: 54).

For the Northern blot analysis, a human Multiple Tissue Northern (MTN™) blot was purchased from CLONTECH. A 1008 nt portion of CD39-L2 gene, corresponding to the 3'UTR, was amplified by PCR using gene specific primers (5'-CATCCTGAGGAGCCACAGCAC-3' (SEQ ID NO: 40); 5'-AGGTTCAGCTCGTGCCGGGCA-3' (SEQ ID NO: 41)). A 315 nt portion of human β-actin gene was amplified with the same gene-specific primers as described above. The probes used in the hybridization were generated by labeling the PCR products with the Prime-It@II Random Primer Labeling Kit from Stratagene (La Jolla, Calif.) in the presence of [α-$^{33}$P]dCTP. The hybridization was performed using the ExpressHyb™ hybridization solution from CLONTECH according to the instructions of the manufacturer. The heart displayed the highest level of expression among all the tissues sampled, being at least 2-fold higher than that of brain. The other tissues, including placenta, lung, liver, skeletal muscle, kidney and pancreas, showed a negligible amount of expression. The high levels of expression of CD39-L2 in heart implicates this protein as a regulator of platelet aggregation in this organ.

EXAMPLE 16

Cellular Localization and Characterization of CD39-L2

A. Cellular Localization

Western blot analysis was performed on COS cells transfected with the plasmid described in Example 15 above to determine the cellular localization of CD39-L2. To detect myc epitope tagged recombinant proteins, the blot was incubated with a 2000-fold dilution of the anti-c-myc monoclonal antibody (Invitrogen) at room temperature for two hours. The secondary antibody (anti-mouse Ig AP conjugate) was diluted 1000-fold and incubated for 1–2 hours at room temperature. Bound antibody was detected by using Sigma Fast™ 5-bromo-4-chloro-3indolyl phosphate/nitro blue tetrazolium (BCIP/NTP) as the alkaline phosphatase substrate according to instructions of the manufacturer.

The recombinant protein was detected in the media and the membrane fractions of the CD39-L2 transfected cells, but not in the cytosolic fraction or control transfections. The relative band intensities suggest that the majority of the recombinant CD39-L2 protein is secreted into the media and a fraction resides in the membrane. The predicted molecular weight of unprocessed CD39-L2 is 53 kD. However, both the membrane and secreted fractions displayed slower mobility by SDS/PAGE than that predicted by its amino acid content, suggesting post-translational modification.

B. Secretion of CD39-L2

To confirm that recombinant CD39-L2 is secreted, the cellular localization was performed using increasing amounts of brefeldin A, an inhibitor of translocation of secretory proteins from the endoplasmic reticulum to the Golgi apparatus. Briefly, brefeldin A was dissolved in ethanol and added to the transfected cells 48 hours after transfection. Both control and brefeldin A-treated cells were washed once with PBS and incubated for 8 hours in serum-free DMEM with none or varying dosages of brefeldin A. For the treated cells, recombinant CD39-L2 in the media decreased in a brefeldin A dose dependent manner. Correspondingly, recombinant CD39-L2 also accumulated in the cytosol in a dose dependent manner. Therefore, it can be inferred that recombinant CD39-L2 secretion follows the conventional cellular secretory pathway.

Flow cytometric analysis was used to determine if recombinant CD39-L2 is expressed on cell surfaces. COS-7 cells were transfected as described above with either pcDNA3.1/myc-His(+)A or pCD39-L2myc-HIS. After 72 hours of transfection, the cells were washed twice with PBS, and dislodged with 10 mM EDTA in PBS. Cells were pelleted by centrifugation at 300 g for five minutes, washed with PBS and resuspended in binding buffer (PBS containing 3% FBS and 0.02% sodium azide) at a concentration of $1 \times 10^6$ cells per 100 μl. The cells were first stained with 20 μg/ml of monoclonal anti-myc antibody for 30 minutes at 4° C. The cells were then washed with binding buffer and stained with 20 μg/ml of R-phycoerythrin conjugated goat anti-mouse IgG antibody (Molecular Probes, Eugene, Oreg.). After washing with binding buffer, the cells were resuspended in 1 ml of binding buffer and analyzed on the FACScalibur flow cytometer (Becton Dickinson Immunocytometry Systems, San Jose, Calif.).

Expression of cell surface recombinant CD39-L2 was found only on cells transfected with pCD39-L2myc-His, while cells from the control transfection showed no antibody binding.

These results of sections A and B demonstrate that recombinant CD39L2 is present in the membrane fraction and is expressed on the cell surface as shown by flow cytometry. These data suggest that CD39L2 is a cell membrane-bound protein. However, the results also show that recombinant CD39L2 is secreted and soluble. One possible explanation is that the soluble form is derived from the transmembrane form via proteolytic-event, as in the cases of tumor necrosis factor and other membrane-derived soluble proteins. Thus, the active soluble form of CD39L2 may be missing at least about 60 amino acids from the N-terminus of the amino acid sequence set forth in SEQ ID NO: 27.

C. N-Linked Glycosylation of CD39-L2

To determine whether CD39-L2 is N-linked glycosylated, CD39-L2 obtained from COS cell conditioned media was tested with Peptide: N-glycosidase F (New England Biolabs, Beverly, Mass.) according to manufacturer's instructions. Briefly, CD39-L2 was denatured with denaturing buffer (0.5% SDS, 1% β-mercaptoethanol) at 100° C. for ten minutes. The CD39-L2 was then incubated with Peptide: N-glycosidase F in G7 buffer (50 mM sodium phosphate, pH 7.5 @25° C.) supplemented with 1% NP-40 at 37° C. for two hours. Another sample of CD39-L2 was treated identically but without the Peptide: N-glycosidase F. Both samples were subjected to SDS-PAGE and were detected by immunodetection using antibodies against the myc-6His epitope.

The sample treated with glycosidase exhibited faster migration on SDS-PAGE than the untreated sample, indicating a reduction in molecular weight. Therefore, CD39-L2 contains N-linked glycosylation that can be enzymatically removed by a glycosidase. There are two potential N-glycosylation sites (Asn-X-Ser/Thr) in the predicted protein sequence.

EXAMPLE 17

Characterization of CD39-L2 Activity

A. Assay of Nucleotidase Activity

Recombinant CD39L2 expressed from transiently transfected COS cells was tested for its NDPase and NTPase activities. CD39-L2 protein was assayed for ADPase activity in the presence of different kinds of inhibitors of ADPases. Control ecto-apyrase activity was determined with protein tethered to the Nickel-NTA resin. Both assays were performed as described in Example 12 above except the protein was in buffer A containing ImM EGTA and 3mM $CaCl_2$. The assay was started by adding ADP to 1 mM followed by a 30 minute incubation at 37° C.

As shown by the results in Table 3 below, CD39-L2 is not inhibited by inhibitors of vacuolar adenosine triphospatase (ATPases) (NEM), mitochondrial ATPase ($N_3^-$) and $Na^-$, $K^-$ ATPase (oubain). An inhibitor of adenylate kinase (Ap5A) did not inhibit activity, while an inhibitor of phosphatases ($F^-$) partially inhibited activity. Metal chelators (EDTA and EGTA) inhibited CD39-L2 activity thereby demonstrating that CD39-L2 activity is dependent on divalent cations. Assays repeated at higher levels of substrate (e.g., 15 mM ADP with 15 mM $CaCl_2$) produced similar results. In addition, CD39L2 ADPase activity at 15 mM ADP was stimulated upon addition of divalent cations; addition of $Mg^{2+}$ ($MgCl_2$ added to 15 mM) stimulates activity 8-fold and $Ca^{2+}$ ($CaCl_2$ added to 15 mM) stimulates activity 17-fold.

These results indicate that CD39L2 exhibits characteristic features of ecto-apyrases.

TABLE 3

Inhibition of CD39-L2 activity

| INHIBITORS | % OF CONTROL |
|---|---|
| Control | 100 ± 3 |
| Ouabain (1 mM) | 101 ± 9 |
| NEM (10 mM) | 88.4 ± 13 |
| $N_3$ (1 mM) | 90 ± 13 |
| F (10 mM) | 63 ± 9 |

TABLE 3-continued

Inhibition of CD39-L2 activity

| INHIBITORS | % OF CONTROL |
|---|---|
| Ap5A (10 μM) | 87 ± 11 |
| EGTA (2 mM) | 34 ± 10 |
| EDTA (2 mM) | 18.4 ± 9 |

The nucleotide specificity of CD39-L2 was also assayed as described in Example 12. The CD39-L2 activity was determined with protein tethered to the Ni-NTA resin. The protein was in assay buffer A containing 1 mM EGTA, 3 mM $CaCl_2$ and 3 mM $MgCl_2$. The assay was started by adding the nucleotides to a final concentration of 1 mM. The samples were assayed at 37° C. for 30 minutes. Results are shown in Table 4 below, wherein values are expressed relative to ADP.

TABLE 4

Substrate Specificity of CD39-L2

| NUCLEOTIDE | % OF CONTROL |
|---|---|
| ADP | 100 ± 8 |
| ATP | 6 ± 2 |
| AMP | 0.6 ± 1 |
| CTP | 44 ± 4 |
| GTP | 39 ± 1 |
| UTP | 13 ± 1 |
| CDP | 282 ± 18 |
| GDP | 338 ± 52 |
| UDP | 303 ± 5 |

CD39L2 shows a substrate specificity for ADP over ATP and the other triphosphate nucleotides. Assays repeated with 15 mM ADP and 1 5 mM CaCl2 confirmed the substrate specificity of CD39L2 for NDP over NTPs; enzymatic activities with CDP, GDP and UDP as substrates were observed, respectively, to be 73%, 280% and 228% relative to ADP hydrolysis. These results confirm that CD39-L2 along with CD39-L4 define a new class of E-type apyrase in humans with a specificity for NDPs as enzymatic substrates.

The effect of excess free $Ca^{2+}$ ions, which inhibits the activity of CD39 and other ecto-apyrases, on ADPase activity of CD39L2 was also determined. A titration analysis of $Ca^{2+}$ concentration on ADPase activity was performed at various ADP concentrations. The protein was in assay buffer A containing concentrations of $CaCl_2$ varying from 2 mM to 15 mM. The assay was started by adding the required amount of ADP at concentrations varying from 2 mM to 15 mM. Each sample was assayed in triplicate at 37° C. for 20 minutes and values were expressed relative to the reactions containing 15 mM $CaCl_2$ and 15 mM ADP. Results showed that high $Ca^{2-}$ concentration had no inhibitory effect on CD39L2 ADPase activity at low substrate concentration. For high substrate concentrations, a correspondingly high $Ca^{2+}$ concentration was required for full activation.

B. Determination of Kinetic Characteristics of CD39-1,2 ADP Hydrolysis

To determine the kinetic characteristics of ADP hydrolysis by CD39L2, recombinant soluble CD39L2 obtained by low pH elution of CD39L2-bound Ni-NTA resin was prepared. Recombinant CD39L2 was eluted off the Ni-NTA resin with acidic elution buffer (0.1 M sodium acetate, pH4.5, 0.3 M NaCl and 0.2 mg/ml inactivated peroxidase (Sigma) as carrier protein). Tris HCl, pH 9, was then added to a final concentration of 70 mM to neutralize the eluted protein sample. Proteins were concentrated 2-fold while small solute concentrations were reduced by 80% using Microcon concentrators. Reactions were carried out in the presence of the apyrase assay buffer with 15 mM $CaCl_2$, 1 mM ouabain, 10 mM NEM, 10 µM Ap5A and concentrations of ADP varying from 0.75 mM to 18 mM, and incubated for 15 min at 37° C. The amount of phosphate released from the reaction was assayed as described above. The amount of the eluted protein used in the reaction was determined by visualizing with Gelcode® Blue (Pierce) staining following SDS-PAGE, and comparing to a series of bovine serum albumin standards of known concentrations. Because the CD39L2 protein is not purified to homogenicity, the location of the CD39-L2 band was identified by immunodetection on a duplicated lane from the same gel.

Assays were carried out as described above. The rate of product release was found to be linear within the first 20 minutes of reaction, so therefore the initial velocity $V_0$ is taken to be the rate of reaction over the first 15 minutes. $V_0$ was determined over a range of substrate concentrations, and was found to respond in a sigmoidal fashion, indicating positive cooperativity. Each data point represented an average of three separate experiments. Curve-fitting of Hill's Equation $\{V_0=(V_{max}[S]^n)/(K+[S]^n)\}$ to the data points was performed by using the DeltaGraph® 4.0 software (SPSS Inc., Chicago, Ill.) and the resulting $R^2$ value was 0.995. The cooperativity, n, was determined to be 2.48, $V_{max}$=1028 pmol/min and K=364.5. The substrate at half-maximal velocity $[S]_{0.5}=K^{1/n}$=10.6 mM. The amount of partially purified CD39L2 protein used in each reaction was estimated to be 3.5 ng so that the specific activity of $V_{max}$ was calculated to be at least 290 µmol/min/mg.

To date, CD39L2 is the only ecto-apyrase that demonstrates positive cooperativity. In contrast, CD39L4 ADPase activity does not appear to possess cooperativity. The positive cooperativity for ADPase activity displayed by the CD39L2 protein indicates that this protein is forming multimers and is predicted to be most active as a tetramer.

Optimal ADP concentrations for CD39L2 are estimated to be in the millimolar range. However, levels of ADP in the circulation have been estimated to be in the low micromolar rangy. This suggests that CD39 L2 would be effective for preventing or reducing a sudden rise in ADP levels, e.g., due to release of ADP from dense granules inside platelets (which have been shown to contain high concentrations of ADP estimated to be up to 0.5 M) within the heart or coronary circulation during injury or trauma. Relatively high concentrations of ADP in the microenvironment of an injury could be closer to the levels where CD39L2 functions optimally. The estimated specific activity of 290 µmol/min/mg for CD39L2 is significantly higher than that reported for the truncated soluble CD39, which is 11 µmol/min/mg at saturation [Gayle et al., *J. Clin. Invest.*, 101, 1851–59 (1998)]. Taken together, the positive cooperativity and high specific activity of CD39L2 suggests that its can function to hydrolyze large amounts of ADP rapidly. These features are expected to be useful in reducing the incidence and/or recurrence of vascular occlusions caused by excessive platelet aggregation, particularly during traumas or insults.

EXAMPLE 18

Determination of CD39-L4 and CD39-L2 Expression Using In Situ Hybridization and Immunohistochemistry A. In situ Hybridization and Immunohistochemistry of CD39-L4 in Kidney Tissues were hybridized with DIG-labeled riboprobes derived from CD39L4 coding sequence nucleotides. A 298 nt fragment of the CD39L4 cDNA 3'-untranslated region was amplified by PCR with oligonucleotide primers 246D13 and 246D4 (5'-ATCCTGGACTTGAGCCTAGAG-3', SEQ ID NO: 34 and 5'-CTGATATTGATGGGTCTTGGG-3', SEQ ID NO: 35). The fragment was subcloned into the pCR™ II-TOPO plasmid (Invitrogen) and sense and antisense RNA were synthesized. The probe was labeled using the digoxigenin labeling kit supplied by Boehringer-Mannheim as described in the manufacturers protocol. Automated in situ hybridization was performed by QualTek Molecular Labs (Santa Barbara, Calif.) using a modified version of a previously published procedure (Myers, J. A., et al., (1995) *J. Surg. Path.* 1, 191–203). The Ventana Medical Systems, Inc. (Tucson. Ariz.) TechMate™ Automated Staining System was used for this procedure. All tissues were fixed in 10% neutral buffered formalin, paraffin-embedded and cut into 4 µm thick sections. Sections were placed onto Ventana's ChemMate™ Capillary Gap Slides (POP075).

Staining of kidney sections revealed that specific cell types hybridized with the antisense probe but not the sense probe in a highly specific manner. The staining of the glomerulus revealed that the epithelia of the Bowman's capsule, podocyte epithelia and mesangial cells were specifically stained. The expression of the CD39L4 protein in this region could be necessary to prevent platelet aggregation in the Bowman's capsule because platelets become highly concentrated in this particular region as water and ions are filtered from the blood. The bloody region within the kidney showed staining of white blood cells, presumably macrophages. This staining is consistent with previous studies where a macrophage cDNA library showed expression of the CD39L4 cDNA. CD39L4 staining was also found in some tubule epithelial cells in the kidney.

Immunohistochemistry on the same tissue was conducted using polyclonal anti-CD39L4 antibody prepared by immunizing rabbits with peptide 246A (EVAKDSIPRSHWKK, SEQ ID NO: 43, corresponding to amino acids 109 to 122 of SEQ ID NO: 3) conjugated to keyhole limpet hemacyanin (KLH), using conventional methods [see, e.g., Harlow et al., "Antibodies: A Laboratory Manual", Cold Spring Harbor Laboratories, Cold Spring Harbor, N.Y. (1998)]. The antibodies were affinity purified using peptide 246A sequence with an extra Cys residue at the C-terminus to allow coupling to a Sulfo link coupling gel (Pierce).

Results showed that the same cell types that expressed CD39L4 mRNA also expressed CD39L4 protein.

B. In Situ Hybridization and Immunohistochemistry of CD39-L2 in Heart

Tissues were hybridized with DIG-labeled riboprobes derived from CD39L2 coding sequence nucleotides 944–1134. Riboprobcs were prepared using the DIG RNA Labeling Kit (Roche Molecular Biochemicals) as described by the instructions of the manufacturer. The 186 nt fragment of the CD39L2 cDNA was amplified by PCR with oligonucleotide primers L2RNA3 and L2RNA2 (5'-GGATGGAAAGGAGTTGGTCAG-3', SEQ ID NO: 36 and 5'-GTCCACATGCTTCACTTCCTC-3' SEQ LD NO: 37). The fragment was subcloned into the pCR™ II-TOPO plasmid (Invitrogen) and sense and antisense RNA were synthesized and labeled as described above. Automated in situ hybridization was performed as described above.

Staining of heart sections revealed that specific cell types hybridized with the antisense probe but not the sense probe in a highly specific manner. The cardiac muscle cells as well as capillary endothelial cells and white blood cells within a blood vessel showed specific staining. This staining is consistent with previous studies where a heart cDNA library showed robust expression of the CD39L2 cDNA.

Immunohistochemistry on the same tissues is conducted using anti-CD39L2 antibody prepared by immunizing rabbits with peptide 102B (TRPPRETPTLTHET, SEQ ID NO: 44, corresponding to amino acids 121 to 134 in SEQ ID NO: 27) conjugated to KLH, using conventional methods [see, e.g., Harlow et al., "Antibodies: A Laboratory Manual", Cold Spring Harbor Laboratories, Cold Spring Harbor, N.Y. (1998)]. Results are expected to confirm that the same cell types that express mRNA also expressed CD39L2 protein.

This in situ hybridization data is consistent with a physiological role for CD39-L4 and CD39-L2 in regulating platelet aggregation and hemostasis. Further in situ hybridization may be carried out to confirm this activity.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims. All references cited within the body of the instant specification are hereby incorporated by reference in their entirety.

What is claimed is:

1. An isolated CD39L2 polynucleotide variant comprising a nucleotide sequence selected from the group consisting of: (a) SEQ ID NO: 45, (b) SEQ ID NO: 46, (c) SEQ ID NO: 47, (d) SEQ ID NO: 48, (e) SEQ ID NO: 49, (f) SEQ ID NO: 50, (g) SEQ ID NO: 51, (h) SEQ ID NO: 53, (i) SEQ ID NO: 54, and (j) protein coding portions of (a) through (i).

2. An isolated CD39L2 polynucleotide variant comprising a nucleotide sequence of SEQ ID NO: 47 or a protein coding portion thereof.

3. The polynucleotide of any one of claims 1 through 2 which is a DNA.

4. The DNA of claim 3 which is a wholly or partially chemically synthesized DNA molecule.

5. An expression vector comprising the DNA of claim 3.

6. A host cell comprising the DNA of claim 3.

7. A method for producing a CD39-like polypeptide comprising the steps of:

(a) growing a culture of host cells according to claim 6 under conditions permitting expression of a CD39-like polypeptide; and (b) isolating the CD39-like polypeptide from the host cell or its growth medium.

8. The method of claim 7 wherein the host cell is *E. coli*.

9. A host cell genetically engineered to express the DNA of claim 3.

10. A method for producing a CD39-like polypeptide comprising the steps of:

(a) growing a culture of host cells according to claim 9 under conditions permitting expression of a CD39-like polypeptide; and (b) isolatig the CD39-like polypeptide from the host cell or its growth medium.

11. The method of claim 10 wherein the host cell is *E. coli*.

* * * * *